United States Patent
Kask et al.

(10) Patent No.: US 11,182,913 B2
(45) Date of Patent: Nov. 23, 2021

(54) SYSTEMS AND METHODS FOR AUTOMATED DISTORTION CORRECTION AND/OR CO-REGISTRATION OF THREE-DIMENSIONAL IMAGES USING ARTIFICIAL LANDMARKS ALONG BONES

(71) Applicants: PerkinElmer Cellular Technologies Germany GmbH, Tallinn (EE); PerkinElmer Health Sciences, Inc., Waltham, MA (US)

(72) Inventors: Peet Kask, Harjumaa (EE); Jeffrey Meganck, Grafton, MA (US)

(73) Assignees: PerkinElmer Cellular Technologies Germany GmbH, Tallinn (EE); PerkinElmer Health Sciences, Inc., Waltham, MA (US)

( * ) Notice: Subject to any disclaimer, the term of this patent is extended or adjusted under 35 U.S.C. 154(b) by 60 days.

(21) Appl. No.: 16/615,618

(22) PCT Filed: Jun. 15, 2018

(86) PCT No.: PCT/US2018/037708
§ 371 (c)(1),
(2) Date: Nov. 21, 2019

(87) PCT Pub. No.: WO2018/232210
PCT Pub. Date: Dec. 20, 2018

(65) Prior Publication Data
US 2020/0098117 A1    Mar. 26, 2020

Related U.S. Application Data

(60) Provisional application No. 62/520,926, filed on Jun. 16, 2017.

(51) Int. Cl.
G06K 9/32    (2006.01)
G06T 7/32    (2017.01)
G06T 7/00    (2017.01)

(52) U.S. Cl.
CPC .............. G06T 7/32 (2017.01); G06K 9/3241 (2013.01); G06T 7/0012 (2013.01); *G06T 2207/30012* (2013.01)

(58) Field of Classification Search
CPC .................... G06T 7/32; G06T 7/0012; G06T 2207/30012; G06K 9/3241; G16H 50/50; G16H 30/40
See application file for complete search history.

(56) References Cited

U.S. PATENT DOCUMENTS

| | | | |
|---|---|---|---|
| 2007/0081712 A1 | 4/2007 | Huang et al. | |
| 2013/0004060 A1* | 1/2013 | Bell | H04N 13/257 382/154 |

(Continued)

FOREIGN PATENT DOCUMENTS

| | | |
|---|---|---|
| JP | 2010221015 A | 10/2010 |
| JP | 2011206148 A | 10/2011 |

(Continued)

OTHER PUBLICATIONS

Nov. 11, 2020—(JP) Office Action—App No. 2019-568075.

(Continued)

*Primary Examiner* — Siamak Harandi
(74) *Attorney, Agent, or Firm* — Banner & Witcoff, Ltd.

(57) ABSTRACT

Presented herein are systems and methods for registering one or more images of one or more subjects based on the automated generation of artificial landmarks. An artificial landmark is a point within an image that is associated with a specific physical location of the imaged region. The artificial landmarks are generated in an automated and robust fashion along the bones of a subject's skeleton that are represented in the image (e.g. graphically). The automatically generated artificial landmarks are used to correct distortion in a single image or to correct distortion in and/or co-register multiple images of a series of images (e.g.

(Continued)

recorded at different time points). The artificial landmark generation approach described herein thereby facilitates analysis of images used, for example, for monitoring the progression of diseases such as pulmonary diseases.

26 Claims, 19 Drawing Sheets

(56) References Cited

U.S. PATENT DOCUMENTS

| | | | |
|---|---|---|---|
| 2015/0023575 A1 | 1/2015 | Valadez et al. | |
| 2016/0302747 A1* | 10/2016 | Averbuch | A61B 6/5205 |
| 2017/0091919 A1 | 3/2017 | Karino | |
| 2018/0338740 A1* | 11/2018 | Behrooz | G06T 7/11 |

FOREIGN PATENT DOCUMENTS

| | | |
|---|---|---|
| JP | 201536015 A | 2/2015 |
| JP | 201763936 A | 4/2017 |

OTHER PUBLICATIONS

Oct. 10, 2018 (WO) International Search Report & Written Opinion PCT/US2018/037708.

Aug. 24, 2021 (KR)—Office Action Application No. 10-2020-7001130.

* cited by examiner

102

104

106

108

SYSTEMS AND METHODS FOR AUTOMATED DISTORTION CORRECTION AND/OR CO-REGISTRATION OF THREE-DIMENSIONAL IMAGES USING ARTIFICIAL LANDMARKS ALONG BONES

CROSS REFERENCE SECTION

This application is a National Stage Application under 35 U.S.C. 371 of PCT application number PCT/US2018/037708 designating the United States and filed Jun. 15, 2018; which claims priority to U.S. Provisional Application Ser. No. 62/520,926, filed Jun. 16, 2017, and entitled "SYSTEMS AND METHODS FOR AUTOMATED DISTORTION CORRECTION AND/OR CO-REGISTRATION OF THREE-DIMENSIONAL IMAGES USING ARTIFICIAL LANDMARKS ALONG BONES", each of which are hereby incorporated by reference in their entireties.

FIELD OF THE INVENTION

This invention relates generally to methods and systems of image analysis. More particularly, in certain embodiments, the invention relates to automated distortion correction and/or registration/co-registration of one or more subject images (e.g. one or more images comprising portions of an axial skeleton of the subject), e.g., captured with a computed tomography (CT) scanner.

BACKGROUND OF THE INVENTION

In vivo imaging of small mammals is performed by a large community of investigators in various fields, e.g., oncology, infectious disease, and drug discovery. There is a wide array of technologies directed to in vivo imaging of mammals—for example, bioluminescence, fluorescence, tomography, and multimodal imaging technologies.

In vivo imaging often involves the use of markers such as fluorescent probes, radionuclides and the like, for non-invasive spatiotemporal visualization of structures and/or biological phenomena inside a live animal. For example, fluorescence molecular tomography (FMT) involves in vivo imaging of mammals for quantitative analysis of administered and/or endogenous probes. In vivo micro Computer Tomography (microCT) imaging, is an x-ray-based technology that scans and produces images of tissues, organs, and non-organic structures with high resolution. MicroCT has evolved quickly, requiring low dose scanning and fast imaging protocols to facilitate multimodal applications and enable longitudinal experimental models. Multimodal imaging involves the fusion of images obtained in different ways, for example, by combining FMT, positron emission tomography (PET), magnetic resonance imaging (MRI), CT, microCT, and/or single photon emission computed tomography (SPECT) imaging data.

Analysis of images, such as microCT images, often involves automated image processing (performed, e.g. by various image analysis software) in order to, for example, identify regions of interest within images (e.g. regions corresponding to particular bones, tissue types, organs). Other image processing may also be used in order to facilitate identification of abnormal features (e.g. tissue morphology, masses such as tumors) within a single image of a subject, and/or identification of changes by comparing multiple images of a subject recorded at different times. In certain cases, comparison of images of different subjects is also useful for identification of abnormal features, and may be facilitated through the use of image processing.

Image analysis methods that facilitate comparison of multiple images recorded at different time points is particularly relevant for monitoring disease progression in a subject (e.g. a small mammal, such as a mouse, rat, guinea pig, or rabbit). For example, changes in tissue morphology, including tumor growth, edema, and fibrosis, can be deduced via analysis of multiple images collected over a period of time. Monitoring disease progression in this manner is relevant for diagnosing subject status, gauging treatment effectiveness, and investigating general aspects of different diseases. Monitoring diseases via image analysis thus can provide new insights relevant for diagnosing conditions, applying appropriate therapies, and developing new treatment procedures.

This is especially true for progressive diseases, such as pulmonary diseases. Pulmonary diseases affect the lungs, and include diseases such as asthma, infections such as influenza and pneumonia, as well as lung cancer. Monitoring the progression of pulmonary diseases involves recording changes in characteristics of the lungs (e.g. tumor growth, edema, fibrosis, a downward expansion of lungs in respect to a subject's ribcage) over time. Imaging techniques, such as computed tomography (e.g. microCT) are used to record images of a region of a subject comprising the subject's lungs at different times. Comparing such images taken at different time points allows changes in the subject's lungs to be observed over time.

Comparing different images taken at different times, however, is quite challenging. In particular, variations in the pose and position of the subject from one image to a next produces variations between images recorded at different time points. For example, graphical representations of tissue (e.g. lung tissue, connective tissue, bones) within different images of a subject may be distorted, positioned, and/or rotated differently from image to image, depending on the pose and position of the subject during recording of a given image. For example, FIG. 1 shows a series of graphical representations of axial skeleton bones of a mouse. These are projections of a 3D mask, where intensity of each pixel is the average intensity of mask voxels along the third dimension. Each projection corresponds to a different three-dimensional representation of a region of the mouse as its position is adjusted and an image is recorded at different times. As is evident in FIG. 1, both the distortion and position of the imaged skeleton differ from image to image, as a result of variations in both the pose and location of the subject between the images. Such variations must be removed in order to allow for meaningful analysis and comparison of a series of multiple images recorded over a period of time.

Thus, there is a need for systems and methods that provide for registration of, including correction of distortions and orientation variations between, multiple images of a subject or images of different subjects. Systems and methods that address this need would facilitate analysis of multiple images of a subject that are recorded at different time points, as well as comparisons between images of different subjects. Such analysis is relevant for many applications, for example, monitoring disease progression (e.g. of relevance for pulmonary diseases).

SUMMARY OF THE INVENTION

Presented herein are systems and methods for registering one or more images of one or more subjects based on the automated generation of artificial landmarks. An artificial landmark is a point within an image that is associated with a specific physical location of the imaged region. The artificial landmarks are generated in an automated and robust fashion along the bones of a subject's skeleton that are represented in the image (e.g. graphically). The automatically generated artificial landmarks are used to correct distortion in a single image or to correct distortion in and/or co-register multiple images of a series of images (e.g. recorded at different time points). The artificial landmark generation approach described herein thereby facilitates analysis of images used, for example, for monitoring the progression of diseases such as pulmonary diseases.

For example, transformations derived from the artificially-generated bone landmarks can be used to correct distortion and/or co-register regions of images representing soft tissue (e.g., lungs, heart, etc.). As used herein, "image registration" refers to distortion correction of one or more images and/or co-registration of multiple images. The graphical representation of soft tissue being registered may be in the same image(s) for which the bone registration is performed, or the soft tissue may be in different images that are obtained at the same time as the images used for bone registration (e.g., via a multi-modality imaging system), or, if otherwise, with the subject in the same pose as in the corresponding bone registration images.

The use of landmarks along bones of a subject for registration (e.g. distortion correction and/or co-registration) is advantageous for monitoring progressive diseases since the configuration of a subject's skeletal bones remains substantially constant over time, while the morphology of soft tissue (e.g. lungs, heart, etc.) may change in response to the disease.

In certain embodiments, the systems and methods for registration (e.g. distortion correction and/or co-registration) described herein are applied to facilitate analysis of images representing a region of a subject comprising the subject's lungs. Such images comprise graphical representations of axial skeleton bones of the subject, such as rib bones, a backbone, and a breastbone. In certain embodiments, artificial landmarks are automatically generated along each of a plurality of rib bones represented within the image. In certain embodiments, artificial landmarks are additionally automatically generated along a breastbone represented within the image.

In certain embodiments, artificial landmarks along rib bones and/or a breastbone represented in a single image are used to correct distortions present in the image that result from (e.g. reflect) the particular pose in which the subject was situated while the image was recorded. In particular, artificial landmarks within the image can be used to determine a transformation [e.g. a linear transformation (e.g. a rigid transformation (e.g. a translation, e.g. a rotation), an affine transformation, e.g. any combination of one or more rigid transformations and/or affine transformations); e.g. a nonlinear transformation (e.g. a regularized or smoothed extrapolation of distortion field, e.g. a thin-plate spline, e.g. a transformation comprising an extrapolation operation and/or a smoothing operation); e.g. a combination of one or more linear transformations and one or more nonlinear transformations] that, when applied to the image, produces a symmetrical representation of the region of the subject. Such symmetrical, standardized images can readily be analyzed, interpreted, and/or compared with other images (e.g. previously recorded images, e.g. previously recorded images that were corrected for distortion similarly) in a direct fashion, without having to account for variations in pose of the subject.

In certain embodiments, artificial landmarks are used to co-register multiple images of a series of images (e.g. recorded at different time points) of a region of a subject. In particular, in certain embodiments, by virtue of their association with specific physical locations of the imaged region, artificial landmarks of different images can be used to determine a transformation that co-registers the images (e.g. aligns the plurality of images to each other). In certain embodiments, a baseline image of a set of images is selected, to which the other images are aligned (e.g. for n images, each n−1 images may be transformed to co-register them with a selected, baseline image of the n images)). In certain embodiments, the baseline image to which each image of a set of images is aligned is not selected from the set of images, and is instead, for example, a pre-defined standard baseline image.

In certain embodiments, artificial landmarks are used to both correct distortion and co-register multiple images of a series of images of a region of the subject. In particular, for each image of a series of images, artificial landmarks of the image are used to determine a transformation that (i) corrects distortion in the image (e.g. resulting from pose variations of the subject) and (ii) aligns the image with the other images of the series. Accordingly, for each image, application of the determined transformation yields a symmetrized image that is co-registered with the other images of the series of images.

In particular, in certain embodiments, image registration (e.g. correcting distortion in one or more images, and/or co-registering multiple images) is accomplished by determining, for each image of one or more images, a transformation that, when applied to the image, substantially optimizes the alignment of the set of artificial landmarks within the image with a set of target landmarks.

Depending on the positions of the target landmarks, the determined transformation that aligns the artificial landmarks in the image with the target landmarks may correct distortions in the image (e.g. yield a symmetrized version of the image) and/or co-register the image with one or more different images.

For example, in certain embodiments, symmetric target landmarks are used for image registration. In order to register a given image, a transformation is determined using artificial landmarks in the image and the symmetric set of target landmarks. The determined transformation can be applied to the image to generate a symmetrized version of the image, thereby correcting distortions. In certain embodiments, a single set of target landmarks is used for registration of multiple images, thereby providing for co-registration of the images. This registration may be conducted for multiple images of a single subject (e.g., collected at different time points) or of multiple subjects. If the single set of target landmarks used for registration of multiple images is symmetric, then both distortion correction and co-registration are accomplished.

In certain embodiments, target landmarks used for registration of a particular image are derived from artificial landmarks within the particular image. For example, correcting distortion in a single image comprises determining a symmetric set of target landmarks from the artificial landmarks in the image, and determining a transformation that optimizes the alignment of the set of artificial landmarks within the image with a set of target landmarks. The determined transformation is applied to the image, thereby producing a symmetric image.

In certain embodiments, target landmarks used for registering a second image are obtained from artificial landmarks of a first image. For example, in order to co-register the second image with the first image, the artificial landmarks of the first image may be used as target landmarks for registration of the second image. Accordingly, determining a transformation that aligns artificial landmarks in the second image with the target landmarks (which are the artificial landmarks of the first image) and applying the transformation to the second image co-registers the second image with the first image.

In certain embodiments, target landmarks are determined from the first image, in order to, as described above, provide for distortion correction (e.g. symmetrization) of the first image. The set of target landmarks can be used for distortion correction and registration of the first image, as well as for distortion correction and registration of one or more other images.

In certain embodiments, the approaches described herein are used for distortion correction and/or co-registration of multiple images of a single subject. In certain embodiments, the approaches described herein are used for distortion correction and/or co-registration of images of different subjects.

An advantage of the artificial landmark generation approach described herein is its robustness to artifacts, such as artifacts resulting from errors in automated identification (e.g. via segmentation) of representations of particular bones within the images, as well as variations in image quality. In particular, in certain embodiments, artificial landmarks are determined from artificial objects (e.g. each artificial object is determined as a center of mass of a corresponding artificial object) generated along bones by morphological and logical image processing operations that are automatically applied to the images (e.g. generation of distance interval masks, e.g. logical AND operations). Accordingly, in contrast to naturally occurring objects, such as specific bones, joints, and the like, artificial objects correspond to fractions of real bones, generated in silico, within an image via a series of specific morphological and logical imaging processing operations.

A surprising result is that generation of artificial objects as described herein is more robust and tolerant of variations in image quality than identification of natural objects. Identification of specific bones, joints, and the like within images via automated segmentation is prone to segmentation errors in certain images, such as lower quality images. Correction of segmentation errors may be accomplished interactively, with the help of a user, but this is very tedious, in particular if there are tens of segmentation errors on each image among several images in a time series.

In certain embodiments, generation of artificial objects via the methods and systems described herein obviates the need for extensive image segmentation. For example, artificial objects may be generated along rib bones within an image via the approach described herein without having to separately identify individual rib bones, which is more challenging and error prone. Accordingly, artificial objects (and, in turn, artificial landmarks generated from artificial objects) are generated in a fully automated fashion, without user interaction. The process of generating artificial objects, and, from them, artificial landmarks for use in image registration, is robust to image artifacts, errors in automated identification of particular bones, and can be used with lower quality images than approaches that require accurate identification of natural objects.

Additionally, unlike natural objects such as specific joints and full bones, the number and density of artificial objects, and, accordingly, landmarks derived from them, can be freely selected. The ability to control the number and density of artificial objects in an image is advantageous for determining transformations for image registration.

In certain embodiments, in order to ensure accurate registration of images, the systems and methods described herein include steps for ensuring that generated artificial landmarks (and/or artificial objects) are correctly identified (e.g., the correspondence between a given artificial landmark (or artificial object) and a particular physical location is correctly identified (e.g., via assignment of index values)). For example, in certain cases, accurate identification of artificial landmarks (and/or artificial objects) ensures that there are no unwanted artifacts among generated seed artificial objects and, similarly, that there are no unwanted artifacts among subsequent artificial objects generated from a seed artificial object. Additionally, correct identification of artificial landmarks and/or artificial objects ensures that pairs opposite rib bone partner landmarks are properly identified when determining a set of symmetric target landmarks for distortion correction. Lastly, correct identification of artificial landmarks and/or artificial objects ensures that artificial landmarks are correctly matched to partner target landmarks for determining image registration transforms.

Accordingly, in certain embodiments, artificial landmarks (and/or artificial objects) are identified (e.g., via assignment of various index values) during the generation process, and the correctness of the identification may be checked at subsequent steps when artificial landmarks are used for image registration. For example, correctness of identification may be checked when determining pairs of opposite rib bone artificial landmarks for generation of target landmarks, as well as when matching artificial landmarks in an image to target landmarks for image registration. In certain embodiments, if identification errors are found, artificial landmarks (and/or artificial objects) that are misidentified are removed from the set of artificial objects (and/or artificial landmarks) in an image, and not used for image registration.

In certain embodiments, the accuracy and robustness with which artificial landmarks are generated from artificial objects is further improved via outlier filtering steps that are applied to remove artificial objects (and/or artificial landmarks determined from such artificial objects) that do not conform to specific criteria. For example, artificial objects may be filtered based on volume in order to remove very small artificial objects that result from e.g. noise and small artifacts in an image. In certain embodiments, criteria used for outlier filtering are based on physical intuition regarding the region of the subject that is imaged, such as the fact that a subject's ribcage is substantially symmetric. Such outlier filtering approaches allow artificial landmarks to be accurately generated with minimal user interaction (e.g. without any user interaction) during the generation process.

Accordingly, by providing an approach for registration (e.g. distortion correction and/or co-registration) of 3-D images of a subject or subjects based on automated generation of artificial landmarks, the systems and methods described herein facilitate the analysis of disease progression in a subject via comparison of tomographic images of the subject. The approach described herein is relevant to images featuring bones of a subject's axial skeleton, including the ribcage, backbone, and breastbone. By providing a robust and automated approach for distortion correction and image co-registration, the systems and methods described herein improve capabilities for monitoring disease progression, particularly relevant for pulmonary diseases.

In one aspect, the invention is directed to a method for registration of one or more 3-D images of a subject, the method comprising: (a) receiving, by a processor of a computing device, a 3-D image of the subject (e.g. a tomographic image, e.g., an image obtained via CT, micro-CT, SPECT, x-ray, MR, ultrasound, and/or a combination of any of these), wherein the 3-D image comprises a graphical representation of rib bones and a backbone; (b) identifying in the graphical representation [e.g., graphically isolating, e.g. automatically (e.g. via segmentation); e.g. via a user interaction], by the processor, (i) the backbone and (ii) ribcage bones comprising the rib bones [{e.g., by determination of a bone mask followed by separation of identified bone tissue into a first part corresponding to an identified backbone and a second part corresponding to identified rib bones} {e.g., by determination of a bone mask followed by separation of identified bone tissue into a first part corresponding to an identified backbone and a second part corresponding to identified ribcage bones (e.g. comprising rib bones together with a breastbone), optionally followed by separation of the identified ribcage bones into an identified breastbone and a part corresponding to the remaining bones (i.e. the rib bones)}]; (c) automatically generating, by the processor, a plurality of seed rib bone artificial objects, each seed rib bone artificial object being within a first distance interval from the backbone in the graphical representation (e.g. (i) for each point of the seed rib bone artificial object, a shortest distance from the point to a surface of the identified backbone is within the first distance interval; e.g. (ii) for each point of the seed rib bone artificial object, a shortest distance from the point to a centerline of the identified backbone is within the first distance interval) and corresponding to a region of a rib bone in the graphical representation (e.g., wherein each seed rib bone artificial object is assigned a left-right index and a rib number index); (d) for each automatically generated seed rib bone artificial object, automatically generating, by the processor, a plurality of associated subsequent rib bone artificial objects, thereby creating a set of artificial objects (e.g. the set comprising the seed and subsequent rib bone artificial objects) within image; (e) automatically performing, by the processor, registration of one or more images of the subject using the set of artificial objects within the image (e.g., using a set of artificial landmarks, each landmark determined based on its corresponding artificial object within the image, e.g. wherein each artificial landmark of the set of artificial landmarks is calculated as a center of mass of each artificial object of the set of artificial objects).

In certain embodiments, identifying the back bone and rib bones comprises determining a set of one or more bone masks to identify specific bones in the graphical representation. For example, determining the set of bone masks may be conducted in multiple steps—e.g., a first step to identify all of the bones in the graphical representation, a second step to identify the backbone, and a third step to identify (undifferentiated) ribcage bones comprising the rib bones. In certain embodiments, the identified ribcage bones include rib bones together with a breastbone. In certain embodiments, a fourth step is performed that separates the identified ribcage bones into (i) an identified breastbone and (ii) remaining bones corresponding to identified rib bones. In certain embodiments, it is not necessary to separately identify the breastbone and rib bones, and the identified ribcage bones correspond to an undifferentiated collection of rib bones together with the breast bone. In certain embodiments, the breast bone and rib bones are separately identified, and operations described herein as being performed on identified ribcage bones and/or a mask corresponding to identified ribcage bones are performed on identified rib bones and/or a mask corresponding to identified rib bones. In certain embodiments, it is not necessary to separately identify individual rib bones (though this may be performed in other embodiments), but rather, an undifferentiated collection of rib bones is identified.

In certain embodiments, the step of automatically generating the plurality of seed rib bone artificial objects comprises: determining a backbone distance map comprising intensity (e.g. numeric) values at each of a plurality of points in three dimensions, each of the intensity values of the backbone distance map corresponding to a distance from the given point in 3-D space to the identified backbone in the graphical representation (e.g. (i) a shortest distance from the given point to a point of the identified backbone; e.g. (ii) a shortest distance from the given point to a centerline of the identified backbone); generating, by the processor, a backbone distance interval mask from the backbone distance map, the backbone distance interval mask corresponding to regions of the image that are within the first distance interval from the identified backbone (e.g. the distance interval mask is a binary mask, wherein points having a distance to the identified backbone within a distance interval (e.g. the first distance interval) are assigned a first value (e.g. a numeric 1, e.g. a Boolean true), and other points are assigned a second value (e.g. a numeric 0, e.g. a Boolean false)); and applying, by the processor, an AND operation (e.g. a point-wise AND operation) between the backbone distance interval mask and a mask corresponding to the identified ribcage bones (e.g., the identified rib bones; e.g. a ribcage bones mask, e.g., a rib bones mask), thereby identifying a plurality of regions of the identified ribcage bones that are within the first distance interval from the identified backbone.

In certain embodiments, step (c) comprises, for each of the plurality of seed rib bone artificial objects, associating with the seed rib bone artificial object (i) a left-right index (e.g. based on an x-coordinate determined from one or more points of the seed rib bone artificial object) and (ii) a rib number index (e.g. based on a z-coordinate determined from one or more points of the seed rib bone artificial object).

In certain embodiments, associating the seed rib bone artificial object with a left-right index comprises, as a preliminary step of applying a preliminary rotation and translation transformation; and, subsequently, determining the left-right index (e.g. based on an x-coordinate determined from one or more points of the seed rib bone artificial object). In certain embodiments, the preliminary rotation and translation transformation is determined using principal axes of the identified backbone and/or principal axes of an identified breastbone in the graphical representation.

In certain embodiments, for each automatically generated seed rib bone artificial object, the plurality of associated subsequent rib bone artificial objects comprises an equidistant chain of rib bone artificial objects.

In certain embodiments, the 3-D image comprises a graphical representation of rib bones, a backbone, and a breastbone, and each rib bone artificial object is at least a predefined first threshold distance from an identified breastbone in the graphical representation (e.g., for each point of each rib bone artificial object, a shortest distance from the point to the identified breastbone is at least the first threshold distance, e.g., for each point of each rib bone artificial object, a shortest distance from the point to a centerline of the identified breastbone is at least the first threshold distance).

In certain embodiments, the method comprises automatically identifying, by the processor, one or more dangerous regions of the image corresponding to regions in which a distance between a first and second rib bone in the graphical representation is below a predefined second threshold distance (e.g., automatically identifying the one or more dangerous regions of the image by applying one or more morphological operations (e.g. including a morphological closing operation) and one or more logical operations to a mask corresponding to the identified ribcage bones), wherein the method comprises ensuring that each generated rib bone artificial object is sufficiently far from any identified dangerous region within the image (e.g., is at least a predefined third threshold distance from the nearest identified dangerous region, e.g., for each point of each rib bone artificial object, a shortest distance from the point to the identified dangerous region is at least the third threshold distance).

In certain embodiments, automatically generating, by the processor, the plurality of subsequent rib bone artificial objects associated with a respective seed rib bone artificial object comprises generating a chain of rib bone artificial objects along a rib bone by beginning with the respective seed rib bone artificial object and, in a stepwise fashion, generating new subsequent rib bone artificial objects, each newly generated rib bone artificial object proceeding outwards (e.g. a predefined distance from the previously generated rib bone artificial object), away from the identified backbone, along the rib bone.

In certain embodiments, the 3-D image comprises a graphical representation of a plurality of rib bones, a backbone, and a breastbone, and generating the chain of artificial rib bone associated with the respective seed rib bone artificial object comprises, for at least one newly generated rib bone artificial object of the chain of rib bone artificial objects: determining whether the newly generated rib bone artificial object is within a predetermined first threshold distance from an identified breastbone in the graphical representation; and responsive to determining that the newly generated rib bone artificial object is within the predetermined first threshold distance from the identified breastbone, terminating generation of subsequent artificial objects associated with the respective seed rib bone artificial object.

In certain embodiments, the method comprises identifying, by the processor, one or more dangerous regions of the image corresponding to regions in which a distance between a first and second rib bone in the graphical representation is below a predefined second threshold distance, and wherein generating the chain of rib bone artificial objects associated with the respective seed rib bone artificial object comprises, for at least one newly generated rib bone artificial object of the chain of rib bone artificial objects: determining whether the newly generated rib bone artificial object is within a predetermined third threshold distance from an identified dangerous region of the image; and responsive to determining that the newly generated rib bone artificial object is within the third predetermined threshold distance from the identified dangerous region of the image, terminating generation of subsequent rib bone artificial objects associated with the respective seed rib bone artificial object.

In certain embodiments, automatically identifying the one or more dangerous regions comprises applying one or more morphological closing operations to a mask corresponding to identified ribcage bones.

In certain embodiments, the 3-D image comprises a graphical representation of at least a portion of a breastbone of the subject, the portion comprising a lower (e.g. tail-sided) end of the breastbone, and wherein the method comprises automatically generating, by the processor, a series of artificial objects along the breastbone by: (f) identifying in the graphical representation [e.g. graphically isolating, e.g., automatically (e.g., via segmentation), e.g. via a user interaction], by the processor, the breastbone [{e.g., by determination of a bone mask followed by separation of identified bones into the backbone, a breastbone, and remaining bones (i.e., the rib bones)} {e.g., by determination of a bone mask followed by separation of identified bone tissue into a first part corresponding to an identified backbone and a second part corresponding to identified ribcage bones (e.g. comprising rib bones together with a breastbone), followed by separation of the identified ribcage bones into an identified breastbone and a part corresponding to the remaining bones (i.e., the rib bones)}] and the lower end of the breastbone (e.g. by determining a minimal z-coordinate of a breastbone mask corresponding to the identified breastbone); (g) automatically generating, by the processor, a seed breastbone artificial object, the seed breastbone artificial object corresponding to a region of the identified breastbone that is within a second distance interval from the lower end of the breastbone (e.g. (i) for each point of the seed breastbone artificial object, a shortest distance from the point to a surface of the identified lower end of the breastbone is within the second distance interval; e.g. e.g. (ii) for each point of the seed breastbone artificial object, a distance (e.g. a Euclidean distance, e.g. a distance along a particular coordinate (e.g. a z-coordinate)) from the point to a point corresponding to the identified lower end of the breastbone is within the second distance interval); and (h) beginning with the seed breastbone artificial object, automatically generating, by the processor, a plurality of associated breastbone artificial objects along the identified breastbone, the plurality of breastbone artificial objects included within the set of artificial objects within the image (e.g. thereby creating a set of artificial objects further comprising the generated breastbone artificial objects).

In certain embodiments, automatically generating, by the processor, the seed breastbone artificial object comprises: determining a breastbone lower end distance map comprising intensity (e.g. numeric) values at each of a plurality of points in three dimensions, each of the intensity values of the backbone distance map corresponding to a distance from a given point in 3-D space to the identified lower end of the breastbone in the graphical representation [e.g. (i) a shortest distance from the given point to a surface of the identified lower end of the breastbone; e.g. (ii) a distance (e.g. a Euclidean distance, e.g. a distance along a particular coordinate (e.g. a z-coordinate)] from the given point to a point corresponding the identified lower end of the breastbone); generating, by the processor, a breastbone lower end distance interval mask from the breastbone lower end distance map, the breastbone lower end distance interval mask corresponding to regions of the image that are within the second distance interval from the lower end of the breastbone (e.g. the breastbone lower end distance interval mask is a binary mask, wherein points having a distance to the lower end of the breastbone within a predefined distance interval (e.g. the second distance interval) are assigned a first value (e.g. a numeric 1, e.g. a Boolean true), and other points are assigned a second value (e.g. a numeric 0, e.g. a Boolean false)); and applying, by the processor, an AND operation (e.g. a pointwise AND operation) between the breastbone lower end distance interval mask and a mask corresponding to the identified breastbone, thereby identifying a region of the identified breastbone that is within the second distance interval from the lower end of the breastbone.

In certain embodiments, the plurality of breastbone artificial comprises an equidistant chain of breastbone artificial objects along the breastbone.

In certain embodiments, automatically generating the plurality of breastbone artificial objects comprises generating a chain of breastbone artificial object by beginning with the seed breastbone artificial object and, in a stepwise fashion, generating new subsequent breastbone artificial objects, each newly generated breastbone artificial object proceeding upwards (e.g. a predefined distance from the previously generated breastbone artificial object), away from the identified lower end of the breastbone.

In certain embodiments, the portion of the breastbone in the graphical representation comprises an upper end of the breastbone, the method comprises identifying in the graphical representation, by the processor, the upper end of the breastbone, and generating the chain of breastbone artificial objects comprises, for at least one newly generated breastbone artificial object: determining whether the newly generated breastbone artificial object reaches or is within a predetermined threshold distance from the identified upper end of the breastbone; and responsive to determining that the newly generated breastbone artificial object reaches or is within the predetermined threshold distance from the identified upper end of the breastbone, terminating generation of subsequent breastbone artificial objects.

In certain embodiments, each automatically generated artificial object of the set of artificial objects within the image (e.g. each rib bone artificial object and/or each breastbone artificial object) is confirmed to have at least a predefined threshold volume.

In certain embodiments, automatically generating the plurality of seed rib bone artificial object comprises: generating, by the processor, a set of prospective seed rib bone artificial objects corresponding to plurality of regions of the rib bones in the graphical representation that are within a distance interval from the backbone in the graphical representation; applying, by the processor, a volume filter to the set of prospective seed rib bone artificial objects, wherein application of the volume filter eliminates, from the set, those artificial objects determined, by the processor, to represent a volume below a predefined threshold volume; and following application of the volume filter, selecting, by the processor, each seed rib bone artificial object from the set of prospective seed rib bone artificial objects.

In certain embodiments, the rib bones in the graphical representation include a plurality of [e.g., corresponding to a number of rib bones on a given side of the subject (e.g., a known number of rib bones)] pairs of opposite rib bones (e.g. each pair of opposite rib bones comprising a right rib bone and a corresponding left rib bone), each rib bone artificial object of a portion of the plurality of rib bone artificial objects belongs to one of a plurality of pairs of rib bone artificial objects, each pair comprising a first rib bone artificial object associated (e.g. based on an associated left-right index of rib bone artificial object) with a first rib bone (e.g. a right rib bone) of a pair of opposite rib bones and a second rib bone artificial object associated (e.g. based on an associated left-right index of rib bone artificial object) with a second rib bone (e.g. a left rib bone) of the pair of opposite rib bones, and for each pair of rib bone artificial objects, (i) a difference between a volume represented by the first object of the pair and a volume represented by the second object of the pair is below a predefined threshold volume difference, and/or (ii) a difference between a height [e.g., a thickness of the object in a z-direction; e.g., distance of the object along the backbone (e.g., determined as an average z-coordinate of the object)] of the first object of the pair and a height of the second object of the pair is below a predefined threshold height difference.

In certain embodiments, the of rib bones in the graphical representation include one or more pairs of opposite rib bones (e.g., each pair of opposite rib bones comprising a right rib bone and a corresponding left rib bone), and automatically generating the plurality of seed rib bone artificial object comprises: generating, by the processor, a set of prospective seed rib bone artificial objects corresponding to plurality of regions of the rib bones in the graphical representation that are within the first distance interval from the backbone; automatically identifying, by the processor, one or more pairs of prospective seed rib bone artificial objects, each pair comprising a first seed rib bone artificial object of a first rib bone of the pair of rib bones and corresponding second seed rib bone artificial object of the opposite rib bone (e.g. based on z-coordinates of each seed rib bone artificial object; e.g. based on an associated rib number index of each seed rib bone artificial object; e.g. based on an associated left-right index of each seed rib bone artificial object); applying, by the processor, a pair comparison filter to the set of prospective seed rib bone artificial objects, wherein application of the pair comparison filter eliminates, from the set, pairs of artificial objects for which (i) a difference between a volume represented by the first object of the pair and a volume represented by the second object of the pair is above a predefined threshold volume difference, and/or (ii) a difference between in a height [e.g. a thickness of the object in a z-direction; e.g. distance of the object along the backbone (e.g. determined as an average z-coordinate of the object)] of the first object of the pair and a height [e.g. a thickness of the object in a z-direction; e.g. distance of the object along the backbone (e.g. determined as an average z-coordinate of the object)] of the second object of the pair is above a predefined threshold height difference; and following application of the pair comparison filter, selecting, by the processor, each seed rib bone artificial object from the set of prospective seed rib bone artificial objects.

In certain embodiments, the method comprises verifying whether the distance (e.g. a Euclidean distance; e.g. a distance along a particular coordinate (e.g. a z coordinate)) between consecutive seed rib bone artificial objects (e.g. pairs of seed rib bone artificial objects, the first and second seed rib bone artificial objects of the pair having consecutive rib number indices; e.g. pairs of seed rib bone artificial objects, the first and second seed rib bone artificial objects of the pair corresponding to nearest neighbors in terms of associates z-coordinates) is consistent (e.g. substantially the same from pair to pair, e.g., within a given tolerance).

In certain embodiments, the method comprises receiving, by the processor, a first image of the subject and a second image of the subject; identifying, by the processor, a plurality of cross-image pairs of artificial objects, each cross-image pair of artificial objects comprising a first artificial object of a first set of artificial objects of the first image and a corresponding second artificial object of a second set of artificial objects of the second image; for each cross-image pair of artificial objects, determining, by the processor, a difference between a volume of the first artificial object and a volume of the second artificial object; and eliminating, by the processor, from the respective set of artificial objects of each respective image, artificial objects of cross-image pairs for which the determined volume difference is above a predefined threshold difference.

In certain embodiments, the method comprises: determining, by the processor, based on the set of artificial objects within the image, an image registration transformation [e.g., a linear transformation (e.g., a rigid transformation (e.g., a translation; e.g., a rotation); e.g., an affine transformation; e.g., any combination of one or more rigid transformations and/or affine transformations); e.g., a nonlinear transformation (e.g., a regularized or smoothed extrapolation of distortion field; e.g., a thin-plate spline; e.g., a transformation comprising an extrapolation operation and/or a smoothing operation); e.g., a combination of one or more linear transformations and one or more nonlinear transformations]; and applying, by the processor, the image registration transformation to a region of the 3-D image, thereby registering the 3-D image (e.g., correcting distortion in the image and/or co-registering the 3-D image with one or more different 3-D images of the subject).

In certain embodiments, the image registration transformation yields symmetrization of the 3-D image, thereby correcting distortions in the image.

In certain embodiments, the received image corresponds to a first image, and the image registration transformation aligns the first image with a second image of the subject, thereby co-registering the first image with the second image.

In certain embodiments determining the image registration transform comprises: determining, by the processor, from the set of artificial objects within the image, a set of artificial landmarks within the image, each artificial landmark corresponding to a point determined from a corresponding artificial object; and determining, by the processor, the image registration transformation [e.g., a linear transformation (e.g., a rigid transformation (e.g., a translation; e.g., a rotation); e.g., an affine transformation; e.g., any combination of one or more rigid transformations and/or affine transformations); e.g., a nonlinear transformation (e.g., a regularized or smoothed extrapolation of distortion field; e.g., a thin-plate spline; e.g., a transformation comprising an extrapolation operation and/or a smoothing operation); e.g., a combination of one or more linear transformations and one or more nonlinear transformations] using the set of artificial landmarks within the image and a set of target landmarks, wherein the image registration transform is determined to, when applied to points corresponding to the artificial landmarks within the image, substantially optimize alignment of the set of artificial landmarks with the set of target landmarks.

In certain embodiments, the set of target landmarks is symmetric [e.g., the set of target landmarks comprises a plurality of right side target landmarks associated with one or more right ribs of the subject and for each right side target landmark, a matching left side target landmark associated with a matching left rib, wherein for each right side target landmark, the position of the right side target landmark maps to the position of the matching left side target landmark under a mirror operation applied to the image (e.g., a mirroring about a y-z plane), and for each left side target landmark, the position of the left side target landmark maps to the position of the matching right side target landmark under a mirror operation applied to the image (e.g., a mirroring about a y-z plane); e.g., the set of target landmarks comprises a plurality of breastbone target landmarks, wherein a position of each breastbone target landmark is substantially invariant under a mirror operation applied to the image (e.g., a mirroring about a y-z plane)].

In certain embodiments, the method comprises determining, by the processor, the set of target landmarks using the set of artificial landmarks within the image.

In certain embodiments, the set of target landmarks is a set of predetermined target landmarks (e.g., determined from one or more 3-D images of the subject different from the received image; e.g., determined from a plurality of 3-D images comprising one or more 3-D images of different subjects).

In certain embodiments, the received 3-D image comprises one or more regions corresponding to graphical representations of soft tissue (e.g., lungs, heart, etc.), and the method further comprises applying by the processor, the image registration transformation to the one or more regions of the image corresponding to graphical representations of soft tissue (e.g., lungs, heart, etc.), thereby registering the soft tissue regions (e.g., correcting distortion in the soft tissue regions and/or co-registering the soft tissue regions with one or more different 3-D images of the subject).

In certain embodiments, the received 3-D image of the subject comprising a graphical representation of a plurality of rib bones and a backbone corresponds to a first image recorded via a first modality (e.g., microCT), and, the method comprises: receiving, by the processor, a second image recorded via a second modality (e.g., different from the first modality; e.g., PET; e.g., an optical imaging modality (e.g., FMT)); determining, by the processor, based on the set of artificial objects within the image, a first image registration transformation; and determining, by the processor, based on the first image registration transformation, a second image registration transformation; and applying, by the processor, the second image registration transformation to a region of the second image.

In certain embodiments, the second image is recorded at substantially the same time as the first image, with the subject in a substantially similar pose and/or position (e.g., the subject is in a fixed pose and/or position during recording of the first and second image; e.g., the first and second images are recorded using a multimodal imaging system).

In certain embodiments, the second image registration transformation is the same as the first image registration transformation.

In certain embodiments, coordinates of a plurality of points of the first image are related to coordinates of a plurality of points of the second image via a known functional relationship (e.g., based on a known spatial relationship between the first and second imaging modalities).

In another aspect, the invention is directed to a method for registration of one or more 3-D images of a subject, the method comprising: (a) receiving, by a processor of a computing device, a 3-D image of the subject (e.g., a tomographic image, e.g., an image obtained via CT, micro-CT, SPECT, x-ray, MR, ultrasound, and/or a combination of any of these), wherein the 3-D image comprises a graphical representation of one or more bones of interest (e.g., axial skeleton bones of the subject; e.g., a plurality of rib bones and/or a backbone; e.g., a breastbone); (b) identifying in the graphical representation [e.g., graphically isolating; e.g., automatically (e.g., via segmentation); e.g., via a user interaction], by the processor, one or more bones of interest (e.g., a plurality of rib bones; e.g., a breastbone) and a reference object (e.g., a backbone; e.g., a lower end of a breastbone); (c) automatically generating, by the processor, one or more seed artificial objects, each seed artificial object being within a first distance interval from the reference object (e.g., (i) for each point of the seed artificial object, a shortest distance from the point to a surface of the reference object is within the first distance interval; e.g., (ii) for each point of the seed artificial object, a shortest distance from the point to a centerline of the reference object is within the first distance interval) and corresponding to a region of a bone of interest in the graphical representation; (d) for each automatically generated seed artificial object, automatically generating, by the processor, a plurality of associated subsequent artificial objects, thereby creating a set of artificial objects (e.g., the set comprising the seed and subsequent rib bone artificial objects) within the image; (e) automatically performing, by the processor, registration of one or more images of the subject using the set of artificial objects within the image (e.g., using a set of artificial landmarks, each landmark determined based on its corresponding artificial objects within the image, e.g. wherein each artificial landmark of the set of artificial landmarks is calculated as a center of mass of each artificial object of the set of artificial objects).

In certain embodiments, the step of automatically generating the one or more seed artificial objects comprises: determining a distance map comprising intensity (e.g., numeric) values at each of a plurality of points in three dimensions, each of the intensity values of the distance map corresponding to a distance from a given point in 3-D space to the reference object (e.g., (i) a shortest distance from the given point to a surface of the identified reference object; e.g., (ii) a shortest distance from the given point to a centerline of the identified reference object); generating, by the processor, a distance interval mask from the distance map (e.g., the distance interval mask is a binary mask, wherein points having a distance to the reference object within a distance interval (e.g., the first distance interval) are assigned a first value (e.g., a numeric 1; e.g., a Boolean true), and other points are assigned a second value (e.g., a numeric 0; e.g. a Boolean false)); and applying, by the processor, an AND operation (e.g., a point-wise AND operation) between the distance interval mask and a mask corresponding to the identified one or more bones of interest, thereby identifying a plurality of regions of the identified bones of interest that are within the first distance interval from the reference object.

In certain embodiments, for each automatically generated seed artificial object, the plurality of associated subsequent artificial objects comprises an equidistant chain of artificial objects.

In certain embodiments, each artificial object is a predefined threshold distance from (e.g., distance from the surface of; e.g., distance from a centerline of) an identified additional bone (e.g., a breastbone) within the graphical representation.

In certain embodiments, the method comprises identifying, by the processor, one or more dangerous regions of the image corresponding to regions in which a distance between a first and second bone of interest in the graphical representation is below a predefined threshold distance (e.g., automatically identifying the one or more dangerous regions of the image by applying one or more morphological operations (e.g., including a morphological closing operation) and one or more logical operations to a mask corresponding to the identified bones of interest), and wherein the method comprises ensuring that each automatically generated artificial object is sufficiently far from any identified dangerous region within the image (e.g., is at least a predefined third threshold distance from the nearest identified dangerous region, e.g., for each point of each artificial object, a shortest distance from the point to the identified dangerous region is at least the third threshold distance).

In certain embodiments, automatically generating, by the processor, the plurality of subsequent artificial objects associated with a respective seed artificial object comprises generating a chain of artificial objects along a bone of interest by beginning with the seed artificial object and, in a stepwise fashion, generating new subsequent artificial objects, each newly generated artificial object proceeding outwards (e.g., a predefined distance from the previously generated rib bone artificial object), away from the identified reference object, along the bone of interest.

In certain embodiments, generating the chain of artificial objects associated with the respective seed artificial object comprises, for at least one newly generated artificial object of the chain of artificial objects: determining whether the newly generated artificial object is within a predetermined threshold distance from an identified additional bone (e.g., a breastbone) in the graphical representation; and responsive to determining that the newly generated artificial object is within the predetermined threshold distance from the identified additional bone (e.g., the breastbone) of the image, terminating generation of subsequent artificial objects associated with the respective seed artificial object.

In certain embodiments, the method comprises identifying, by the processor, one or more dangerous regions of the image corresponding to regions in which a distance between a first and second bone of interest in the graphical representation is below a predefined threshold distance, and generating the chain of artificial objects associated with the respective seed artificial object comprises, for at least one newly generated artificial object of the chain of artificial objects: determining whether the newly generated artificial object is within a predetermined threshold distance from an identified dangerous region of the image; and responsive to determining that the newly generated artificial object is within the predetermined threshold distance from the identified dangerous region of the image, terminating generation of subsequent artificial objects associated with the respective seed artificial object.

In certain embodiments, each artificial object of the set of artificial objects within the image (e.g. each rib bone artificial object and/or each breastbone artificial object) is confirmed to have at least a predefined threshold volume.

In certain embodiments, automatically generating the one or more seed artificial objects comprises: generating, by the processor, a set of prospective seed artificial objects corresponding to plurality of regions of the one or more bones of interest that are within the first distance interval from the reference object; applying, by the processor, a volume filter to the set of prospective seed artificial objects, wherein application of the volume filter eliminates, from the set, those artificial objects determined, by the processor, to represent a volume below a predefined threshold volume; and following application of the volume filter, selecting, by the processor, the seed artificial object from the set of prospective seed artificial objects.

In certain embodiments, the method comprises: receiving, by the processor, a first image of the subject and a second image of the subject; identifying, by the processor, a plurality of cross-image pairs of artificial objects, each cross-image pair of artificial objects comprising a first artificial object of a first set of artificial objects of the first image and a corresponding second artificial object of a second set of artificial objects of the second image; for each cross-image pair of artificial objects, determining, by the processor, a difference between a volume of the first artificial object and a volume of the second artificial object; and eliminating, by the processor, from the respective set of artificial objects of each respective image, artificial objects of cross-image pairs for which the determined volume difference is above a predefined threshold difference.

In certain embodiments, the method comprises: determining, by the processor, based on the set of artificial objects within the image, an image registration transformation [e.g. a linear transformation (e.g. a rigid transformation (e.g. a translation, e.g. a rotation), an affine transformation, e.g. any combination of one or more rigid transformations and/or affine transformations); e.g. a nonlinear transformation (a regularized or smoothed extrapolation of distortion field, e.g. a thin-plate spline, e.g. a transformation comprising an extrapolation operation and/or a smoothing operation); e.g. a combination of one or more linear transformations and one or more nonlinear transformations]; and applying, by the processor, the image registration transformation to a region of the 3-D image, thereby registering the 3-D image (e.g. correcting distortion in the image and/or co-registering the 3-D image with one or more different 3-D images of the subject).

In certain embodiments, the image registration transformation yields symmetrization of the 3-D image, thereby correcting distortions in the image.

In certain embodiments, the received image corresponds to a first image, and the image registration transformation aligns the first image with a second image of the subject, thereby co-registering the first image with the second image.

In certain embodiments, determining the image registration transformation comprises: determining, by the processor, from the set of artificial objects within the image, a set of artificial landmarks within the image, each landmark corresponding to a point determined from a corresponding artificial object; and determining, by the processor, the image registration transformation [e.g. a linear transformation (e.g. a rigid transformation (e.g. a translation, e.g. a rotation), an affine transformation, e.g. any combination of one or more rigid transformations and/or affine transformations); e.g. a nonlinear transformation (a regularized or smoothed extrapolation of distortion field, e.g. a thin-plate spline, e.g. a transformation comprising an extrapolation operation and/or a smoothing operation); e.g. a combination of one or more linear transformations and one or more nonlinear transformations] using the set of artificial landmarks within the image and a set of target landmarks, wherein the image registration transformation is determined to, when applied to points corresponding to the artificial landmarks within the image, substantially optimize alignment of the set of artificial landmarks with the set of target landmarks.

In certain embodiments, the set of target landmarks is symmetric [e.g. the set of target landmarks comprises a plurality of right side target landmarks associated with one or more bones of interest on a right side of the subject and for each right side target landmark, a matching left side target landmark associated with a matching bone of interest on a left side of the subject, wherein for each right side target landmark, the position of the right side target landmark maps to the position of the matching left side target landmark under a mirror operation applied to the image (e.g. a mirroring about a y-z plane), and for each left side target landmark, the position of the left side target landmark maps to the position of the matching right side target landmark under a mirror operation applied to the image (e.g. a mirroring about a y-z plane)].

In certain embodiments, the method comprises determining, by the processor, the set of target landmarks using the set of artificial landmarks within the image.

In certain embodiments, the set of target landmarks is a set of predetermined target landmarks (e.g. determined from one or more 3-D images of the subject different from the received image; e.g. determined from a plurality of 3-D images comprising one or more 3-D images of different subjects).

In certain embodiments, the received 3-D image comprises one or more regions corresponding to graphical representations of soft tissue (e.g. lungs, heart, etc.), and the method further comprises applying by the processor, the image registration transformation to the one or more regions of the image corresponding to graphical representations of soft tissue (e.g. lungs, heart, etc.), thereby registering the soft tissue regions (e.g. correcting distortion in the soft tissue regions and/or co-registering the soft tissue regions with one or more different 3-D images of the subject).

In certain embodiments, the received 3-D image of the subject corresponds to a first image recorded via a first modality (e.g. microCT), and, the method comprises: receiving, by the processor, a second image recorded via a second modality (e.g. different from the first modality; e.g. PET; e.g. an optical imaging modality (e.g. FMT)); determining, by the processor, based on the set of artificial objects within the image, a first image registration transformation; and determining, by the processor, based on the first image registration transformation, a second image registration transformation; and applying, by the processor, the second image registration transformation to a region of the second image.

In certain embodiments, the second image is recorded at substantially the same time as the first image, with the subject in a substantially similar pose and/or position (e.g. the subject is in a fixed pose and/or position during recording of the first and second image; e.g. the first and second images are recorded using a multimodal imaging system).

In certain embodiments, the second image registration transformation is the same as the first image registration transformation.

In certain embodiments, coordinates of a plurality of points of the first image are related to coordinates of a plurality of points of the second image via a known functional relationship (e.g. based on a known spatial relationship between the first and second imaging modalities).

In certain embodiments, the 3-D image comprises a graphical representation of a plurality of rib bones and a backbone, the identified one or more bones of interest comprise a plurality of rib bones, and the identified reference object is a backbone of the subject.

In certain embodiments, the plurality of rib bones includes one or more pairs of opposite rib bones (e.g. each pair of opposite rib bones comprising a right rib bone and a corresponding left rib bone), each rib bone artificial object of a portion of the plurality of rib bone artificial objects belongs to one of a plurality of pairs of rib bone artificial objects, each pair comprising a first rib bone artificial object associated with a first rib bone (e.g. a right rib bone) of a pair of opposite rib bones and a second rib bone artificial object associated with a second rib bone (e.g. a left rib bone) of the pair of opposite rib bones, and for each pair of rib bone artificial objects, (i) a difference between a volume represented by the first object of the pair and a volume represented by the second object of the pair is below a predefined threshold volume difference, and/or (ii) a difference between in a height [e.g. a thickness of the object in a z-direction; e.g. distance of the object along the backbone (e.g. determined as an average z-coordinate of the object)] of the first object of the pair and a height [e.g. a thickness of the object in a z-direction; e.g. distance of the object along the backbone (e.g. determined as an average z-coordinate of the object)] of the second object of the pair is below a predefined threshold height difference.

In certain embodiments, the plurality of rib bones in the graphical representation includes one or more pairs of opposite rib bones (e.g. each pair of opposite rib bones comprising a right rib bone and a corresponding left rib bone), and automatically generating the plurality of seed rib bone artificial objects comprises: identifying, by the processor, a set of prospective seed rib bone artificial objects corresponding to plurality of regions of the identified rib bones that are within a distance interval from the backbone; automatically identifying, by the processor, one or more pairs of prospective seed rib bone artificial objects, each pair comprising a first seed rib bone artificial object of a first rib bone of the pair of rib bones and corresponding second seed rib bone artificial object of the opposite rib bone; applying, by the processor, a pair comparison filter to the set of prospective seed rib bone artificial objects, wherein application of the pair comparison filter eliminates, from the set, pairs of artificial objects for which (i) a difference between a volume represented by the first object of the pair and a volume represented by the second object of the pair is above a predefined threshold volume difference, and/or (ii) a difference between in a height [e.g. a thickness of the object in a z-direction; e.g. distance of the object along the backbone (e.g. determined as an average z-coordinate of the object)] of the first object of the pair and a height [e.g. a thickness of the object in a z-direction; e.g. distance of the object along the backbone (e.g. determined as an average z-coordinate of the object)] of the second object of the pair is above a predefined threshold height difference; and following application of the pair comparison filter, selecting, by the processor, each seed rib bone artificial object from the set of prospective seed rib bone artificial objects.

In certain embodiments, the 3-D image comprises a graphical representation of a breastbone of the subject and a lower end of the breastbone.

In certain embodiments, the one or more bones of interest comprise(s) the breastbone in the graphical representation and the reference object comprises a lower end of the breastbone.

In another aspect, the invention is directed to a system for registration of one or more 3-D images of a subject, the system comprising: a processor; and a memory having instructions stored thereon, wherein the instructions, when executed by the processor, cause the processor to: (a) receive a 3-D image of the subject (e.g., a tomographic image; e.g., an image obtained via CT, micro-CT, SPECT, x-ray, MR, ultrasound, and/or a combination of any of these), wherein the 3-D image comprises a graphical representation of rib bones and a backbone; (b) identify in the graphical representation [e.g., graphically isolating, e.g. automatically (e.g. via segmentation); e.g. via a user interaction] (i) the backbone and (ii) ribcage bones comprising the rib bones [e.g., by determination of a bone mask followed by separation of identified bone tissue into a first part corresponding to an identified backbone and a second part corresponding to identified rib bones [{e.g., by determination of a bone mask followed by separation of identified bone tissue into a first part corresponding to an identified backbone and a second part corresponding to identified rib bones (e.g., and, optionally, a third part corresponding to an identified breastbone)} {e.g., by determination of a bone mask followed by separation of identified bone tissue into a first part corresponding to an identified backbone and a second part corresponding to identified ribcage bones (e.g., comprising rib bones together with a breastbone), optionally followed by separation of the identified ribcage bones into an identified breastbone and a part corresponding to the remaining bones (i.e., the rib bones)}]; (c) automatically generate a plurality of seed rib bone artificial objects, each seed rib bone artificial object being within a first distance interval from the backbone in the graphical representation (e.g., (i) for each point of the seed rib bone artificial object, a shortest distance from the point to a surface of the identified backbone is within the first distance interval; e.g., (ii) for each point of the seed rib bone artificial object, a shortest distance from the point to a centerline of the identified backbone is within the first distance interval) and corresponding to a region of a rib bone in the graphical representation (e.g., wherein each seed rib bone artificial object is assigned a left-right index and a rib number index); (d) for each automatically generated seed rib bone artificial object, automatically generate a plurality of associated subsequent rib bone artificial objects, thereby creating a set of artificial objects (e.g., the set comprising the seed and subsequent rib bone artificial objects) within image; (e) automatically perform registration of one or more images of the subject using the set of artificial objects within the image (e.g., using a set of artificial landmarks, each landmark determined based on its corresponding artificial object within the image; e.g., wherein each artificial landmark of the set of artificial landmarks is calculated as a center of mass of each artificial object of the set of artificial objects).

In certain embodiments, identifying the back bone and rib bones comprises determining a set of one or more bone masks to identify specific bones in the graphical representation. For example, determining the set of bone masks may be conducted in multiple steps—e.g., a first step to identify all of the bones in the graphical representation, a second step to identify the backbone, and a third step to identify (undifferentiated) ribcage bones comprising the rib bones. In certain embodiments, the identified ribcage bones include rib bones together with a breastbone. In certain embodiments, a fourth step is performed that separates the identified ribcage bones into (i) an identified breastbone and (ii) remaining bones corresponding to identified rib bones. In certain embodiments, it is not necessary to separately identify the breastbone and rib bones, and the identified ribcage bones correspond to an undifferentiated collection of rib bones together with the breast bone. In certain embodiments, the breast bone and rib bones are separately identified, and operations described herein as being performed on identified ribcage bones and/or a mask corresponding to identified ribcage bones are performed on identified rib bones and/or a mask corresponding to identified rib bones. In certain embodiments, it is not necessary to separately identify individual rib bones (though this may be performed in other embodiments), but rather, an undifferentiated collection of rib bones is identified.

In certain embodiments, the instructions cause the processor to automatically generate the plurality of seed rib bone artificial objects by: determining a backbone distance map comprising intensity (e.g. numeric, e.g. non-negative numeric) values at each of a plurality of points in three dimensions, each of the intensity values of the backbone distance map corresponding to a distance from the given point in 3-D space to the identified backbone in the graphical representation (e.g., (i) a shortest distance from the given point to the identified backbone; e.g., (ii) a shortest distance from the given point to a centerline of the identified backbone); generating a backbone distance interval mask from the backbone distance map, the backbone distance interval mask corresponding to regions of the image that are within the first distance interval from the identified backbone [e.g., the distance interval mask is a binary mask, wherein points having a distance to the identified backbone within a distance interval (e.g., the first distance interval) are assigned a first value (e.g., a numeric 1; e.g. a Boolean true), and other points are assigned a second value (e.g., a numeric 0; e.g., a Boolean false)]; and applying an AND operation (e.g., a point-wise AND operation) between the backbone distance interval mask and a mask corresponding to the identified ribcage bones (e.g., the identified rib bones), thereby identifying a plurality of regions of the identified ribcage bones that are within the first distance interval from the identified backbone.

In certain embodiments, at step (c), the instructions cause the processor to, for each of the plurality of seed rib bone artificial objects, associate with the seed rib bone artificial object (i) a left-right index (e.g., based on an x-coordinate determined from one or more points of the seed rib bone artificial object) and (ii) a rib number index (e.g., based on a z-coordinate determined from one or more points of the seed rib bone artificial object).

In certain embodiments, associating the seed rib bone artificial object with a left-right index comprises, as a preliminary step of applying a preliminary rotation and translation transformation; and, subsequently, determining the left-right index (e.g. based on an x-coordinate determined from one or more points of the seed rib bone artificial object). In certain embodiments, the preliminary rotation and translation transformation is determined using principal axes of the identified backbone and/or principal axes of an identified breastbone in the graphical representation.

In certain embodiments, for each automatically generated seed rib bone artificial object, the plurality of associated subsequent rib bone artificial objects comprises an equidistant chain of rib bone artificial objects.

In certain embodiments, the 3-D image comprises a graphical representation of rib bones, a backbone, and a breastbone, and each rib bone artificial object is at least a predefined first threshold distance from an identified breastbone in the graphical representation (e.g., for each point of each rib bone artificial object, a shortest distance from the point to the identified breastbone is at least the first threshold distance; e.g., for each point of each rib bone artificial object, a shortest distance from the point to a centerline of the identified breastbone is at least the first threshold distance).

In certain embodiments, the instructions cause the processor to: automatically identify one or more dangerous regions of the image corresponding to regions in which a distance between a first and second rib bone in the graphical representation is below a predefined second threshold distance [e.g., automatically identifying the one or more dangerous regions of the image by applying one or more morphological operations (e.g. including a morphological closing operation) and one or more logical operations to a mask corresponding to the identified ribcage bones]; and generate each rib bone artificial object such that it is sufficiently far from any identified dangerous region within the image (e.g., is at least a predefined third threshold distance from the nearest identified dangerous region; e.g., for each point of each rib bone artificial object, a shortest distance from the point to the identified dangerous region is at least the third threshold distance).

In certain embodiments, the instructions cause the processor to automatically generate the plurality of subsequent rib bone artificial objects associated with a respective seed rib bone artificial object by generating a chain of rib bone artificial objects along a rib bone by beginning with the respective seed rib bone artificial object and, in a stepwise fashion, generating new subsequent rib bone artificial objects, each newly generated rib bone artificial object proceeding outwards (e.g., a predefined distance from the previously generated rib bone artificial object), away from the identified backbone, along the rib bone.

In certain embodiments, the 3-D image comprises a graphical representation of rib bones, a backbone, and a breastbone, and the instructions cause the processor to generate the chain of artificial rib bone objects associated with the respective seed rib bone artificial object by, for at least one newly generated rib bone artificial object of the chain of rib bone artificial objects: determining whether the newly generated rib bone artificial object is within a predetermined first threshold distance from an identified breastbone in the graphical representation; and responsive to determining that the newly generated rib bone artificial object is within the predetermined first threshold distance from the identified breastbone, terminating generation of subsequent artificial objects associated with the respective seed rib bone artificial object.

In certain embodiments, the instructions cause the processor to: identify one or more dangerous regions of the image corresponding to regions in which a distance between a first and second rib bone in the graphical representation is below a predefined second threshold distance; and generate the chain of rib bone artificial objects associated with the respective seed rib bone artificial object, by, for at least one newly generated rib bone artificial object of the chain of rib bone artificial objects: determining whether the newly generated rib bone artificial object is within a predetermined third threshold distance from an identified dangerous region of the image; and responsive to determining that the newly generated rib bone artificial object is within the third predetermined threshold distance from the identified dangerous region of the image, terminating generation of subsequent rib bone artificial objects associated with the respective seed rib bone artificial object.

In certain embodiments, the instructions cause the processor to automatically identify the one or more dangerous regions by applying one or more morphological closing operations to a mask corresponding to identified ribcage bones.

In certain embodiments, the 3-D image comprises a graphical representation of at least a portion of a breastbone of the subject, the portion comprising a lower (e.g. tail-sided) end of the breastbone, and wherein the instructions cause the processor to automatically generate a series of artificial objects along the breastbone by: (f) identifying in the graphical representation [e.g., graphically isolating, e.g., automatically (e.g. via segmentation), e.g., via a user interaction[the breastbone [{e.g., by determination of a bone mask followed by separation of identified bone tissue into the backbone, a breastbone, and remaining bones (i.e., the rib bones)} {e.g., by determination of a bone mask followed by separation of identified bone tissue into a first part corresponding to an identified backbone and a second part corresponding to identified ribcage bones (e.g., comprising rib bones together with a breastbone), followed by separation of the identified ribcage bones into an identified breastbone and a part corresponding to the remaining bones (i.e., the rib bones)}] and the lower end of the breastbone (e.g., by determining a minimal z-coordinate of a breastbone mask corresponding to the identified breastbone); (g) automatically generating a seed breastbone artificial object, the seed breastbone artificial object corresponding to a region of the identified breastbone that is within a second distance interval from the lower end of the breastbone [e.g., (i) for each point of the seed breastbone artificial object, a shortest distance from the point to a surface of the identified lower end of the breastbone is within the second distance interval; e.g., (ii) for each point of the seed breastbone artificial object, a distance (e.g., a Euclidean distance; e.g., a distance along a particular coordinate (e.g., a z-coordinate)) from the point to a point corresponding to the identified lower end of the breastbone is within the second distance interval]; and (h) beginning with the seed breastbone artificial object, automatically generating a plurality of associated breastbone artificial objects along the identified breastbone, the plurality of breastbone artificial objects included within the set of artificial objects within the image (e.g., thereby creating a set of artificial objects further comprising the generated breastbone artificial objects).

In certain embodiments, the instructions cause the processor to automatically generate the seed breastbone artificial object by: determining a breastbone lower end distance map comprising intensity (e.g., numeric) values at each of a plurality of points in three dimensions, each of the intensity values of the backbone distance map corresponding to a distance from a given point in 3-D space to the identified lower end of the breastbone in the graphical representation [e.g., (i) a shortest distance from the given point to a surface of the identified lower end of the breastbone; e.g., (ii) a distance (e.g., a Euclidean distance, e.g., a distance along a particular coordinate (e.g., a z-coordinate)) from the given point to a point corresponding the identified lower end of the breastbone]; generating a breastbone lower end distance interval mask from the breastbone lower end distance map, the breastbone lower end distance interval mask corresponding to regions of the image that are within the second distance interval from the lower end of the breastbone [e.g., the breastbone lower end distance interval mask is a binary mask, wherein points having a distance to the lower end of the breastbone within a predefined distance interval (e.g., the second distance interval) are assigned a first value (e.g., a numeric 1; e.g., a Boolean true), and other points are assigned a second value (e.g., a numeric 0; e.g. a Boolean false)]; and applying, an AND operation (e.g., a point-wise AND operation) between the breastbone lower end distance interval mask and a mask corresponding to the identified breastbone, thereby identifying a region of the identified breastbone that is within the second distance interval from the lower end of the breastbone.

In certain embodiments, the plurality of breastbone artificial comprises an equidistant chain of breastbone artificial objects along the breastbone.

In certain embodiments, the instructions cause the processor to automatically generate the plurality of breastbone artificial objects by generating a chain of breastbone artificial object by beginning with the seed breastbone artificial object and, in a stepwise fashion, generating new subsequent breastbone artificial objects, each newly generated breastbone artificial object proceeding upwards (e.g., a predefined distance from the previously generated breastbone artificial object), away from the identified lower end of the breastbone.

In certain embodiments, the portion of the breastbone in the graphical representation comprises an upper end of the breastbone, and the instructions cause the processor to: identify in the graphical representation, by the processor, the upper end of the breastbone; and generate the chain of breastbone artificial objects by, for at least one newly generated breastbone artificial object: determining whether the newly generated breastbone artificial object reaches or is within a predetermined threshold distance from the identified upper end of the breastbone; and responsive to determining that the newly generated breastbone artificial object reaches or is within the predetermined threshold distance from the identified upper end of the breastbone, terminating generation of subsequent breastbone artificial objects.

In certain embodiments, each automatically generated artificial object of the set of artificial objects within the image (e.g., each rib bone artificial object and/or each breastbone artificial object) is confirmed to have at least a predefined threshold volume.

In certain embodiments, the instructions cause the processor to automatically generate the plurality of seed rib bone artificial objects by: generating a set of prospective seed rib bone artificial objects corresponding to plurality of regions of the rib bones in the graphical representation that are within a distance interval from the backbone in the graphical representation; applying a volume filter to the set of prospective seed rib bone artificial objects, wherein application of the volume filter eliminates, from the set, those artificial objects determined, by the processor, to represent a volume below a predefined threshold volume; and following application of the volume filter, selecting each seed rib bone artificial object from the set of prospective seed rib bone artificial objects.

In certain embodiments, the rib bones in the graphical representation include a plurality [e.g., corresponding to a number of rib bones on a given side of the subject (e.g., a known number of rib bones)] of pairs of opposite rib bones (e.g., each pair of opposite rib bones comprising a right rib bone and a corresponding left rib bone), each rib bone artificial object of a portion of the plurality of rib bone artificial objects belongs to one of a plurality of pairs of rib bone artificial objects, each pair comprising a first rib bone artificial object associated (e.g., based on an associated left-right index of rib bone artificial object) with a first rib bone (e.g., a right rib bone) of a pair of opposite rib bones and a second rib bone artificial object associated (e.g. based on an associated left-right index of rib bone artificial object) with a second rib bone (e.g., a left rib bone) of the pair of opposite rib bones, and for each pair of rib bone artificial objects, (i) a difference between a volume represented by the first object of the pair and a volume represented by the second object of the pair is below a predefined threshold volume difference, and/or (ii) a difference between a height [e.g., a thickness of the object in a z-direction; e.g. distance of the object along the backbone (e.g., determined as an average z-coordinate of the object)] of the first object of the pair and a height [e.g., a thickness of the object in a z-direction; e.g., distance of the object along the backbone (e.g., determined as an average z-coordinate of the object)] of the second object of the pair is below a predefined threshold height difference.

In certain embodiments, the rib bones in the graphical representation include a plurality of pairs of opposite rib bones (e.g., each pair of opposite rib bones comprising a right rib bone and a corresponding left rib bone), and the instructions cause the processor to automatically generate the plurality of seed rib bone artificial object by: generating a set of prospective seed rib bone artificial objects corresponding to plurality of regions of the rib bones in the graphical representation that are within the first distance interval from the backbone; automatically identifying one or more pairs of prospective seed rib bone artificial objects, each pair comprising a first seed rib bone artificial object of a first rib bone of the pair of rib bones and corresponding second seed rib bone artificial object of the opposite rib bone (e.g., based on z-coordinates of each seed rib bone artificial object; e.g., based on an associated rib number index of each seed rib bone artificial object; e.g., based on an associated left-right index of each seed rib bone artificial object); applying a pair comparison filter to the set of prospective seed rib bone artificial objects, wherein application of the pair comparison filter eliminates, from the set, pairs of artificial objects for which (i) a difference between a volume represented by the first object of the pair and a volume represented by the second object of the pair is above a predefined threshold volume difference, and/or (ii) a difference between in a height of the first object of the pair and a height of the second object of the pair is above a predefined threshold height difference; and following application of the pair comparison filter, selecting each seed rib bone artificial object from the set of prospective seed rib bone artificial objects.

In certain embodiments, the instructions cause the processor to verify whether the distance [e.g., a Euclidean distance; e.g., a distance along a particular coordinate (e.g., a z-coordinate)] between consecutive seed rib bone artificial objects (e.g., pairs of seed rib bone artificial objects, the first and second seed rib bone artificial objects of the pair having consecutive rib number indices; e.g., pairs of seed rib bone artificial objects, the first and second seed rib bone artificial objects of the pair corresponding to nearest neighbors in terms of associates z-coordinates) is consistent (e.g., substantially the same from pair to pair; e.g., within a given tolerance).

In certain embodiments, the instructions cause the processor to: receive a first image of the subject and a second image of the subject; identify a plurality of cross-image pairs of artificial objects, each cross-image pair of artificial objects comprising a first artificial object of a first set of artificial objects of the first image and a corresponding second artificial object of a second set of artificial objects of the second image; for each cross-image pair of artificial objects, determine a difference between a volume of the first artificial object and a volume of the second artificial object; and eliminate, from the respective set of artificial objects of each respective image, artificial objects of cross-image pairs for which the determined volume difference is above a predefined threshold difference.

In certain embodiments, the instructions cause the processor to: determine, based on the set of artificial objects within the image, an image registration transformation [e.g., a linear transformation (e.g., a rigid transformation (e.g., a translation; e.g., a rotation); e.g., an affine transformation; e.g., any combination of one or more rigid transformations and/or affine transformations); e.g., a nonlinear transform (e.g., a regularized or smoothed extrapolation of distortion field; e.g., a thin-plate spline transform; e.g., a transformation comprising an extrapolation operation and/or a smoothing operation); e.g., a combination of one or more linear transformations and one or more nonlinear transformations]; and apply the image registration transformation to a region of the 3-D image, thereby registering the 3-D image (e.g., correcting distortion in the image and/or co-registering the 3-D image with one or more different 3-D images of the subject).

In certain embodiments, the image registration transformation yields symmetrization of the 3-D image, thereby correcting distortions in the image.

In embodiments, the received image corresponds to a first image, and the image registration transformation aligns the first image with a second image of the subject, thereby co-registering the first image with the second image.

In certain embodiments, the instructions cause the processor to determine the image registration transformation by: determining, from the set of artificial objects within the image, a set of artificial landmarks within the image, each artificial landmark corresponding to a point determined from a corresponding artificial object; and determining the image registration transformation [e.g. a linear transformation (e.g. a rigid transformation (e.g. a translation, e.g. a rotation), an affine transformation, e.g. any combination of one or more rigid transformations and/or affine transformations); e.g. a nonlinear transformation (e.g. a regularized or smoothed extrapolation of distortion field, e.g. a thin-plate spline, e.g. a transformation comprising an extrapolation operation and/or a smoothing operation); e.g. a combination of one or more linear transformations and one or more nonlinear transformations] using the set of artificial landmarks within the image and a set of target landmarks, wherein the image registration transformation is determined to, when applied to points corresponding to the artificial landmarks within the image, substantially optimize alignment of the set of artificial landmarks with the set of target landmarks.

In certain embodiments, the set of target landmarks is symmetric, [e.g., the set of target landmarks comprises a plurality of right side target landmarks associated with one or more right ribs of the subject and for each right side target landmark, a matching left side target landmark associated with a matching left rib, wherein for each right side target landmark, the position of the right side target landmark maps to the position of the matching left side target landmark under a mirror operation applied to the image (e.g., a mirroring about a y-z plane), and for each left side target landmark, the position of the left side target landmark maps to the position of the matching right side target landmark under a mirror operation applied to the image (e.g., a mirroring about a y-z plane); e.g., the set of target landmarks comprises a plurality of breastbone target landmarks, wherein a position of each breastbone target landmark is substantially invariant under a mirror operation applied to the image (e.g., a mirroring about a y-z plane)].

In certain embodiments, the instructions cause the processor to determine the set of target landmarks using the set of artificial landmarks within the image.

In certain embodiments, the set of target landmarks is a set of predetermined target landmarks (e.g., determined from one or more 3-D images of the subject different from the received image; e.g., determined from a plurality of 3-D images comprising one or more 3-D images of different subjects).

In certain embodiments, the received 3-D image comprises one or more regions corresponding to graphical representations of soft tissue (e.g., lungs, heart, etc.), and the instructions cause the processor to apply the image registration transformation to the one or more regions of the image corresponding to graphical representations of soft tissue (e.g., lungs, heart, etc.), thereby registering the soft tissue regions (e.g., correcting distortion in the soft tissue regions and/or co-registering the soft tissue regions with one or more different 3-D images of the subject).

In certain embodiments, the received 3-D image of the subject comprising a graphical representation of rib bones and a backbone corresponds to a first image recorded via a first modality (e.g., microCT), and the instructions cause the processor to: receive a second image recorded via a second modality (e.g., different from the first modality; e.g., PET; e.g., an optical imaging modality (e.g., FMT)); determine, based on the set of artificial objects within the image, a first image registration transformation; and determine, based on the first image registration transformation, a second image registration transform; and apply, the second image registration transformation to a region of the second image.

In certain embodiments, the second image is recorded at substantially the same time as the first image, with the subject in a substantially similar pose and/or position (e.g., the subject is in a fixed pose and/or position during recording of the first and second image; e.g., the first and second images are recorded using a multimodal imaging system).

In certain embodiments, the second image registration transformation is the same as the first image registration transformation.

In certain embodiments, coordinates of a plurality of points of the first image are related to coordinates of a plurality of points of the second image via a known functional relationship (e.g., based on a known spatial relationship between the first and second imaging modalities).

In another aspect, the invention is directed to a system for registration of one or more 3-D images of a subject, the system comprising: a processor; and a memory with instructions stored thereon, wherein the instructions, when executed by the processor, cause the processor to: (a) receive a 3-D image of the subject (e.g., a tomographic image; e.g., an image obtained via CT, micro-CT, SPECT, x-ray, MR, ultrasound, and/or a combination of any of these), wherein the 3-D image comprises a graphical representation of one or more bones of interest (e.g., axial skeleton bones of the subject; e.g., rib bones and/or a backbone, e.g. a breastbone); (b) identify in the graphical representation [e.g., graphically isolating; e.g. automatically (e.g. via segmentation); e.g. via a user interaction] one or more bones of interest (e.g., ribcage bones (e.g. rib bones together with a breastbone); e.g., rib bones; e.g., a breastbone) and a reference object (e.g., a backbone; e.g., a lower end of a breastbone); (c) automatically generate one or more seed artificial objects, each seed artificial object being within a first distance interval from the reference object (e.g., (i) for each point of the seed artificial object, a shortest distance from the point to a surface of the reference object is within the first distance interval; e.g., (ii) for each point of the seed artificial object, a shortest distance from the point to a centerline of the reference object is within the first distance interval) and corresponding to a region of a bone of interest in the graphical representation; (d) for each automatically generated seed artificial object, automatically generate a plurality of associated subsequent artificial objects, thereby creating a set of artificial objects (e.g., the set comprising the seed and subsequent rib bone artificial objects) within the image; (e) automatically perform registration of one or more images of the subject using the set of artificial objects within the image [e.g., using a set of artificial landmarks, each landmark determined based on its corresponding artificial objects within the image (e.g., wherein each artificial landmark of the set of artificial landmarks is calculated as a center of mass of each artificial object of the set of artificial objects)].

In certain embodiments, the instructions cause the processor to automatically generating the one or more seed artificial objects by: determining a distance map comprising intensity (e.g., numeric; e.g., non-negative numeric) values at each of a plurality of points in three dimensions, each of the intensity values of the distance map corresponding to a distance from a given point in 3-D space to the reference object (e.g., (i) a shortest distance from the given point to a surface of the identified reference object; e.g., (ii) a shortest distance from the given point to a centerline of the identified reference object); generating a distance interval mask from the distance map [e.g., the distance interval mask is a binary mask, wherein points having a distance to the reference object within a distance interval (e.g., the first distance interval) are assigned a first value (e.g., a numeric 1; e.g., a Boolean true), and other points are assigned a second value (e.g., a numeric 0; e.g., a Boolean false)]; and applying an AND operation (e.g., a point-wise AND operation) between the distance interval mask and a mask corresponding to the identified one or more bones of interest, thereby identifying a plurality of regions of the identified bones of interest that are within the first distance interval from the reference object.

In certain embodiments, for each automatically generated seed artificial object, the plurality of associated subsequent artificial objects comprises an equidistant chain of artificial objects.

In certain embodiments, each artificial object is a predefined threshold distance from (e.g., distance from the surface of; e.g., distance from a centerline of) an identified additional bone (e.g., a breastbone) within the graphical representation.

In certain embodiments, the instructions cause the processor to: identify one or more dangerous regions of the image corresponding to regions in which a distance between a first and second bone of interest in the graphical representation is below a predefined threshold distance (e.g., automatically identifying the one or more dangerous regions of the image by applying one or more morphological operations (e.g., including a morphological closing operation) and one or more logical operations to a mask corresponding to the identified bones of interest); and automatically generate each artificial object such that it is sufficiently far from any identified dangerous region within the image (e.g., is at least a predefined third threshold distance from the nearest identified dangerous region; e.g., for each point of each artificial object, a shortest distance from the point to the identified dangerous region is at least the third threshold distance).

In certain embodiments, the instructions cause the processor to automatically generate the plurality of subsequent artificial objects associated with a respective seed artificial object by generating a chain of artificial objects along a bone of interest by beginning with the seed artificial object and, in a stepwise fashion, generating new subsequent artificial objects, each newly generated artificial object proceeding outwards (e.g., a predefined distance from the previously generated rib bone artificial object), away from the identified reference object, along the bone of interest.

In certain embodiments, the instructions cause the processor to generate the chain of artificial objects associated with the respective seed artificial object by, for at least one newly generated artificial object of the chain of artificial objects: determining whether the newly generated artificial object is within a predetermined threshold distance from an identified additional bone (e.g., a breastbone) in the graphical representation; and responsive to determining that the newly generated artificial object is within the predetermined threshold distance from the identified additional bone (e.g., the breastbone) of the image, terminating generation of subsequent artificial objects associated with the respective seed artificial object.

In certain embodiments, the instructions cause the processor to: identify one or more dangerous regions of the image corresponding to regions in which a distance between a first and second bone of interest in the graphical representation is below a predefined threshold distance, and generate the chain of artificial objects associated with the respective seed artificial object by, for at least one newly generated artificial object of the chain of artificial objects: determining whether the newly generated artificial object is within a predetermined threshold distance from an identified dangerous region of the image; and responsive to determining that the newly generated artificial object is within the predetermined threshold distance from the identified dangerous region of the image, terminating generation of subsequent artificial objects associated with the respective seed artificial object.

In certain embodiments, each artificial object of the set of artificial objects within the image (e.g., each rib bone artificial object and/or each breastbone artificial object) is confirmed to have at least a predefined threshold volume.

In certain embodiments, the instructions cause the processor to automatically generate the one or more seed artificial objects by: generating a set of prospective seed artificial objects corresponding to plurality of regions of the one or more bones of interest that are within the first distance interval from the reference object; applying a volume filter to the set of prospective seed artificial objects, wherein application of the volume filter eliminates, from the set, those artificial objects determined to represent a volume below a predefined threshold volume; and following application of the volume filter, selecting the seed artificial objects from the set of prospective seed artificial objects.

In certain embodiments, the instructions cause the processor: to receive a first image of the subject and a second image of the subject; identify a plurality of cross-image pairs of artificial objects, each cross-image pair of artificial objects comprising a first artificial object of a first set of artificial objects of the first image and a corresponding second artificial object of a second set of artificial objects of the second image; for each cross-image pair of artificial objects, determine a difference between a volume of the first artificial object and a volume of the second artificial object; and eliminate, from the respective set of artificial objects of each respective image, artificial objects of cross-image pairs for which the determined volume difference is above a predefined threshold difference.

In certain embodiments, the instructions cause the processor to: determine, based on the set of artificial objects within the image, an image registration transformation [e.g., a linear transformation (e.g., a rigid transformation (e.g., a translation; e.g., a rotation); e.g., an affine transformation; e.g. any combination of one or more rigid transformations and/or affine transformations); e.g., a nonlinear transformation (e.g., a regularized or smoothed extrapolation of distortion field; e.g., a thin-plate spline; e.g., a transformation comprising an extrapolation operation and/or a smoothing operation); e.g., a combination of one or more linear transformations and one or more nonlinear transformations]; and apply the image registration transformation to a region of the 3-D image, thereby registering the 3-D image (e.g., correcting distortion in the image and/or co-registering the 3-D image with one or more different 3-D images of the subject).

In certain embodiments, the image registration transformation yields symmetrization of the 3-D image, thereby correcting distortions in the image.

In certain embodiments, the received image corresponds to a first image, and the image registration transformation aligns the first image with a second image of the subject, thereby co-registering the first image with the second image.

In certain embodiments, the instructions cause the processor to determine the image registration transformation by: determining, from the set of artificial objects within the image, a set of artificial landmarks within the image, each landmark corresponding to a point determined from a corresponding artificial object; and determining the image registration transformation [e.g., a linear transformation (e.g., a rigid transformation (e.g., a translation; e.g., a rotation); e.g., an affine transformation; e.g., any combination of one or more rigid transformations and/or affine transformations); e.g., a nonlinear transformation (e.g., a regularized or smoothed extrapolation of distortion field; e.g., a thin-plate spline; e.g., a transformation comprising an extrapolation operation and/or a smoothing operation); e.g., a combination of one or more linear transformations and one or more nonlinear transformations] using the set of artificial landmarks within the image and a set of target landmarks, wherein the image registration transformation is determined to, when applied to points corresponding to the artificial landmarks within the image, substantially optimize alignment of the set of artificial landmarks with the set of target landmarks.

In certain embodiments, the set of target landmarks is symmetric [e.g., the set of target landmarks comprises a plurality of right side target landmarks associated with one or more bones of interest on a right side of the subject and for each right side target landmark, a matching left side target landmark associated with a matching bone of interest on a left side of the subject, wherein for each right side target landmark, the position of the right side target landmark maps to the position of the matching left side target landmark under a mirror operation applied to the image (e.g., a mirroring about a y-z plane), and for each left side target landmark, the position of the left side target landmark maps to the position of the matching right side target landmark under a mirror operation applied to the image (e.g., a mirroring about a y-z plane)].

In certain embodiments, the instructions cause the processor to determine the set of target landmarks using the set of artificial landmarks within the image.

In certain embodiments, the set of target landmarks is a set of predetermined target landmarks (e.g., determined from one or more 3-D images of the subject different from the received image; e.g., determined from a plurality of 3-D images comprising one or more 3-D images of different subjects).

In certain embodiments, the received 3-D image comprises one or more regions corresponding to graphical representations of soft tissue (e.g., lungs, heart, etc.), and the instructions cause the processor to apply the image registration transformation to the one or more regions of the image corresponding to graphical representations of soft tissue (e.g., lungs, heart, etc.), thereby registering the soft tissue regions (e.g., correcting distortion in the soft tissue regions and/or co-registering the soft tissue regions with one or more different 3-D images of the subject).

In certain embodiments, the received 3-D image of the subject corresponds to a first image recorded via a first modality (e.g. microCT), and, wherein the instructions cause the processor to: receive a second image recorded via a second modality (e.g., different from the first modality; e.g., PET; e.g., an optical imaging modality (e.g., FMT)); determine, based on the set of artificial objects within the image, a first image registration transformation; and determine, based on the first image registration transform, a second image registration transformation; and applying the second image registration transformation to a region of the second image.

In certain embodiments, the second image is recorded at substantially the same time as the first image, with the subject in a substantially similar pose and/or position (e.g., the subject is in a fixed pose and/or position during recording of the first and second image; e.g., the first and second images are recorded using a multimodal imaging system).

In certain embodiments, the second image registration transformation is the same as the first image registration transformation.

In certain embodiments, coordinates of a plurality of points of the first image are related to coordinates of a plurality of points of the second image via a known functional relationship (e.g., based on a known spatial relationship between the first and second imaging modalities).

In certain embodiments, the 3-D image comprises a graphical representation of rib bones and a backbone, the identified one or more bones of interest comprise rib bones, and the identified reference object is a backbone of the subject.

In certain embodiments, the graphical representation of rib bones includes a plurality of pairs of opposite rib bones (e.g., each pair of opposite rib bones comprising a right rib bone and a corresponding left rib bone), each rib bone artificial object of a portion of the plurality of rib bone artificial objects belongs to one of a plurality of pairs of rib bone artificial objects, each pair comprising a first rib bone artificial object associated with a first rib bone (e.g., a right rib bone) of a pair of opposite rib bones and a second rib bone artificial object associated with a second rib bone (e.g., a left rib bone) of the pair of opposite rib bones, and for each pair of rib bone artificial objects, (i) a difference between a volume represented by the first object of the pair and a volume represented by the second object of the pair is below a predefined threshold volume difference, and/or (ii) a difference between in a height of the first object of the pair and a height of the second object of the pair is below a predefined threshold height difference.

In certain embodiments, the rib bones in the graphical representation includes one or more pairs of opposite rib bones (e.g., each pair of opposite rib bones comprising a right rib bone and a corresponding left rib bone), and wherein the instruction cause the processor to automatically generate the plurality of seed rib bone artificial objects by: identifying a set of prospective seed rib bone artificial objects corresponding to plurality of regions of the rib bones that are within a distance interval from the backbone; automatically identifying one or more pairs of prospective seed rib bone artificial objects, each pair comprising a first seed rib bone artificial object of a first rib bone of the pair of rib bones and corresponding second seed rib bone artificial object of the opposite rib bone; applying a pair comparison filter to the set of prospective seed rib bone artificial objects, wherein application of the pair comparison filter eliminates, from the set, pairs of artificial objects for which (i) a difference between a volume represented by the first object of the pair and a volume represented by the second object of the pair is above a predefined threshold volume difference, and/or (ii) a difference between in a height of the first object of the pair and a height of the second object of the pair is above a predefined threshold height difference; and following application of the pair comparison filter, selecting each seed rib bone artificial object from the set of prospective seed rib bone artificial objects.

In certain embodiments, the 3-D image comprises a graphical representation of a breastbone of the subject and a lower end of the breastbone.

In certain embodiments, the one or more bones of interest comprise(s) the breastbone in the graphical representation and the reference object comprises a lower end of the breastbone.

BRIEF DESCRIPTION OF THE FIGURES

The foregoing and other objects, aspects, features, and advantages of the present disclosure will become more apparent and better understood by referring to the following description taken in conjunction with the accompanying drawings, in which.

Figure 1:
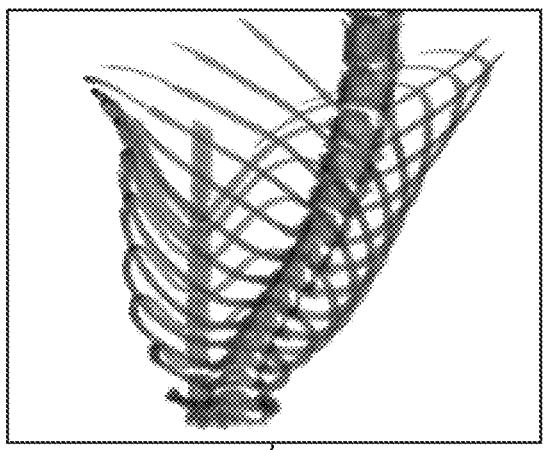
FIG. 1 is a series of images comprising graphical representations of ribcage bones of a mouse, each image showing a projection of graphical representations of ribcage bones identified within a different 3-D image of the mouse recorded at a different time point, according to an illustrative embodiment.
Figure 1:
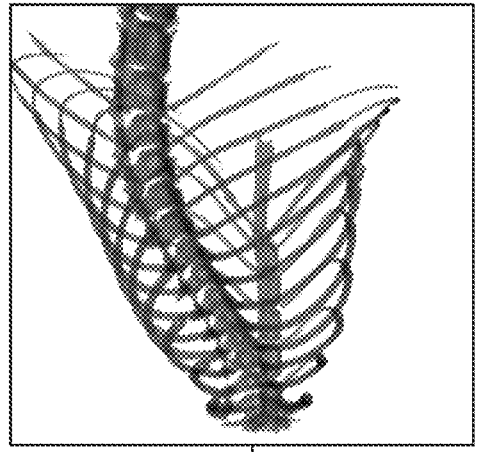
Figure 1:
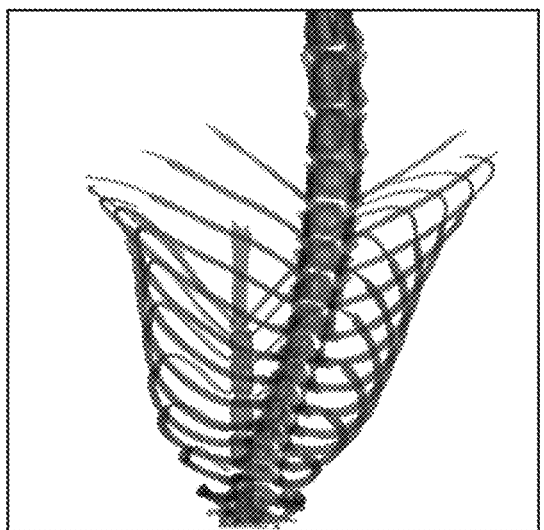
Figure 1:
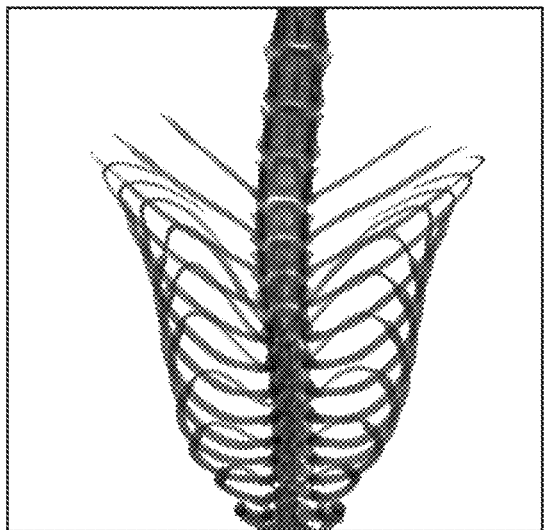

The features and advantages of the present disclosure will become more apparent from the detailed description set forth below when taken in conjunction with the drawings, in which like reference characters identify corresponding elements throughout. In the drawings, like reference numbers generally indicate identical, functionally similar, and/or structurally similar elements.

Definitions

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context and except where such number would exceed 100% of a possible value.

Image: As used herein, an "image"—for example, a 3-D image of mammal—includes any visual representation, such as a photo, a video frame, streaming video, as well as any electronic, digital or mathematical analogue of a photo, video frame, or streaming video. Any apparatus described herein, in certain embodiments, includes a display for displaying an image or any other result produced by the processor. Any method described herein, in certain embodiments, includes a step of displaying an image or any other result produced via the method.

3-D, three-dimensional: As used herein, "3-D" or "three-dimensional" with reference to an "image" means conveying information about three dimensions. A 3-D image may be rendered as a dataset in three dimensions and/or may be displayed as a set of two-dimensional representations, or as a three-dimensional representation. In certain embodiments, a 3-D image is represented as voxel (e.g., volumetric pixel) data. As used herein, the phrase "point of an image" refers to a voxel of the image.

Various medical imaging devices and other 3-D imaging devices (e.g., a computed tomography scanner (CT scanner), a microCT scanner, etc.) output 3-D images comprising voxels or otherwise have their output converted to 3-D images comprising voxels for analysis. In certain embodiments, a voxel corresponds to a unique coordinate in a 3-D image (e.g., a 3-D array). In certain embodiments, each voxel exists in either a filled or an unfilled state (e.g., binary ON or OFF).

Region of an image: As used herein the term "region" as used in "region of an image" refers to a collection of points within the image. A region of an image may be identified as a region that is within specific distance interval from a reference object of the image. In certain embodiments, the reference object is a specific, single point within the image and the identified region is a collection of points wherein, for each point of the region, a distance from the given point to the reference point is within the specific distance interval. In certain embodiments, the reference object is a one-dimensional (1-D) line and the identified region is a collection of points wherein, for each point of the region, a shortest distance from the given point to a point of the 1-D reference line is within the specific distance interval. In certain embodiments, the reference object is a two-dimensional (2-D) surface and the identified region is a collection of points wherein, for each point of the region, a shortest distance from the given point to a point of the 2-D surface is within the specific distance interval. In certain embodiments, the reference object is a three-dimensional region of the image and the identified region is a collection of points wherein, for each point of the region, a shortest distance from the given point to a surface of the reference object is within the specific distance interval. In certain embodiments, the reference object is a three-dimensional region of the image and the identified region is a collection of points wherein, for each point of the region, a shortest distance from the given point to a center line of the reference object is within the specific distance interval.

Mask: As used herein, a "mask" is a graphical pattern that identifies a 2-D or 3-D region and is used to control the elimination or retention of portions of an image or other graphical pattern. In certain embodiments, a mask is represented as a binary 2-D or 3-D image, wherein each pixel of a 2-D image or each voxel of a 3-D image is assigned one of two values of a binary set of values (e.g. each pixel or voxel may be assigned a 1 or a 0, e.g. each pixel or voxel may be assigned a Boolean "true" or "false" value).

Registration: As used herein, the terms "registration," and "registering," as in registration of one or more images or registering one or more images refers to transforming an image or images in order to produce a corresponding image or corresponding images having a standardized view. In certain embodiments registration of an image comprises correcting distortions in the image in order to produce a symmetrized version of the image. In certain embodiments, registration of an image includes co-registering the image with one or more other images.

Provide: As used herein, the term "provide", as in "providing data", refers to a process for passing data in between different software applications, modules, systems, and/or databases. In certain embodiments, providing data comprises the execution of instructions by a process to transfer data in between software applications, or in between different modules of the same software application. In certain embodiments a software application may provide data to another application in the form of a file. In certain embodiments an application may provide data to another application on the same processor. In certain embodiments standard protocols may be used to provide data to applications on different resources. In certain embodiments a module in a software application may provide data to another module by passing arguments to that module.

DETAILED DESCRIPTION

It is contemplated that systems, architectures, devices, methods, and processes of the claimed invention encompass variations and adaptations developed using information from the embodiments described herein. Adaptation and/or modification of the systems, architectures, devices, methods, and processes described herein may be performed, as contemplated by this description.

Throughout the description, where articles, devices, systems, and architectures are described as having, including, or comprising specific components, or where processes and methods are described as having, including, or comprising specific steps, it is contemplated that, additionally, there are articles, devices, systems, and architectures of the present invention that consist essentially of, or consist of, the recited components, and that there are processes and methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

The mention herein of any publication, for example, in the Background section, is not an admission that the publication serves as prior art with respect to any of the claims presented herein. The Background section is presented for purposes of clarity and is not meant as a description of prior art with respect to any claim.

Documents are incorporated herein by reference as noted. Where there is any discrepancy in the meaning of a particular term, the meaning provided in the Definition section above is controlling.

Headers are provided for the convenience of the reader—the presence and/or placement of a header is not intended to limit the scope of the subject matter described herein.

Described herein are systems and methods for distortion correction and/or co-registration of 3-D images via automated generation of artificial landmarks along bones pictured within the 3-D images.

In certain embodiments, the approach described herein facilitates comparison of 3-D images of a region of a subject that are recorded at different points in time. Comparing multiple 3-D images, wherein each image is recorded at a different point in time is relevant for monitoring the progression of diseases such as pulmonary diseases. In certain embodiments, monitoring disease progression includes measuring tumor growth, fibrosis, edema and combinations thereof over time, based on data recording in 3-D images. In certain embodiments, changes in the morphology of lung tissue and surrounding connective tissues occur as a physiological response to the progression of a pulmonary disease, and, accordingly, are monitored over time. For example, in addition to changes in tumor volume, a researcher or clinician may wish to monitor a downward expansion of a subject's lungs in relation to the rib bones of the subject—such changes in lung morphology can be indicative of compensation for a reduction of volume and/or functioning of regions of the subject's lungs.

Analyzing 3-D images in this manner, by comparing different images recorded at different time points is challenging because for each image, the subject (e.g. a mouse, e.g. a human subject) is often in a different pose and position. Accordingly, apart from meaningful variations that are indicative of e.g. changes in tissue morphology (e.g. lung tissue) of a subject, images recorded at different time points also comprise variations with respect to each other corresponding to distortions and position differences resulting from pose and position differences of the subject during recording of each image.

FIG. 1 shows a series of four projections 102, 104, 106, 108 showing graphical representations of axial skeleton bones of a mouse. Each projection is a projection of a 3D mask that identifies axial skeleton bones in a 3-D image. In each projection, the intensity of each pixel is the average intensity of mask voxels along the third dimension. Each projection corresponds to a different 3-D image of a region of the mouse, each image, recorded at a different time point. Each of the four images to which the displayed projections correspond was recorded approximately one week after the previous image (e.g. projection 102 corresponds to a first image; projection 104 corresponds to a second 3-D image recorded approximately one week after the first image; projection 106 corresponds to a third image recorded approximately one week after the second image; projection 108 corresponds to a fourth image recorded approximately one week after the third image). The differences in the shape and orientation of the bones of the mouse shown in each projection illustrate the rather arbitrary pose and/or position that the mouse was in during recording of each image.

Figure 2:
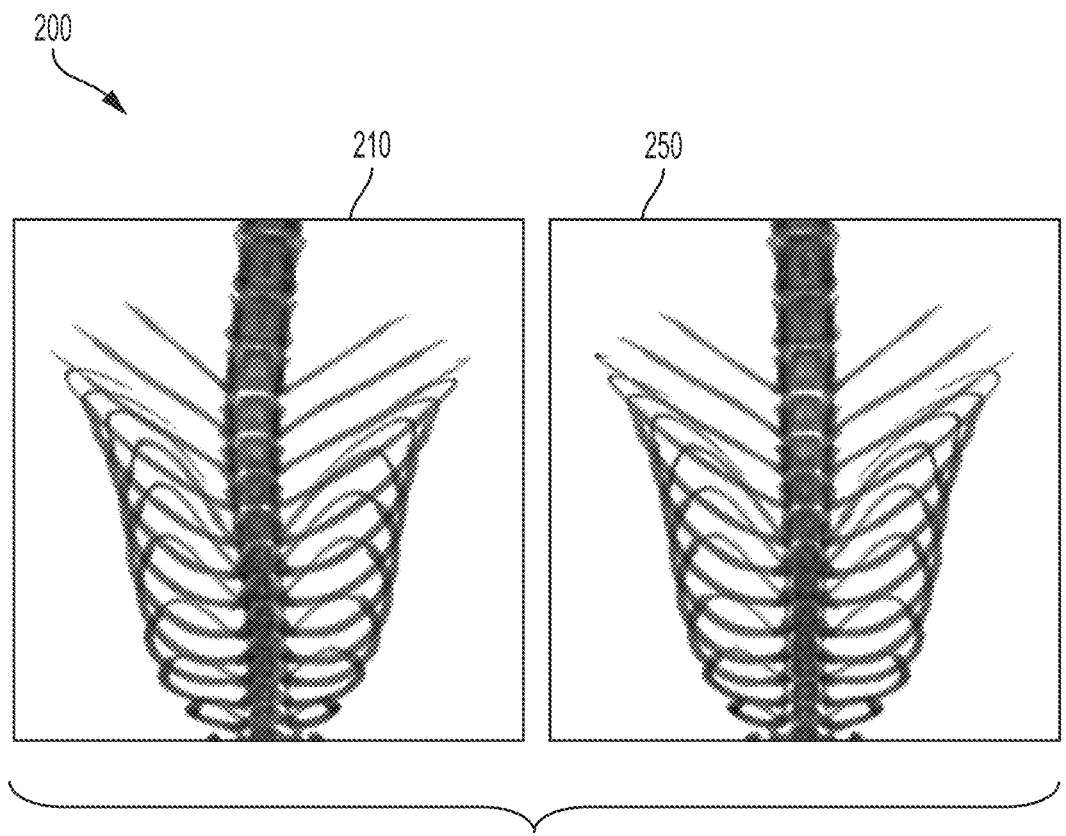
FIG. 2 is a set of two images comprising graphical representations of ribcage bones of a mouse, showing results of distortion correction, according to an illustrative embodiment.

Turning to FIG. 2, in certain embodiments distortion correction is applied to one or more images of a subject, thereby correcting for differences in the pose of the subject at the time a given image was recorded. FIG. 2 shows a set 200 of two projections of masks identifying axial skeleton bones in a 3-D image of a region of a mouse comprising the mouse's ribcage (e.g. a plurality of rib bones) as well as the backbone. The left projection 210 shows the ribcage bones of the mouse, prior to distortion correction, and the right projection 250 shows the ribcage bones of the mouse of the same 3-D image, after distortion correction. The portion of the skeleton of the mouse shown in projection 210 has an asymmetrical shape that reflects the particular pose of the mouse when the 3-D image was recorded. The distortion correction operation, when applied to the 3-D image, transforms the image such that the skeleton of the mouse has a symmetrical shape, yielding the corrected 3-D image to which projection 250 corresponds. In particular, each coordinate of the distortion corrected image (to which projection 250 corresponds) is related to a corresponding coordinate of the original image (to which projection 210 corresponds) via a transformation (e.g. a distortion field correction) described in the following. Accordingly, distortion correction of a given image comprises determining an appropriate transformation that, when applied to the image, produces a symmetrized version.

Figure 3:
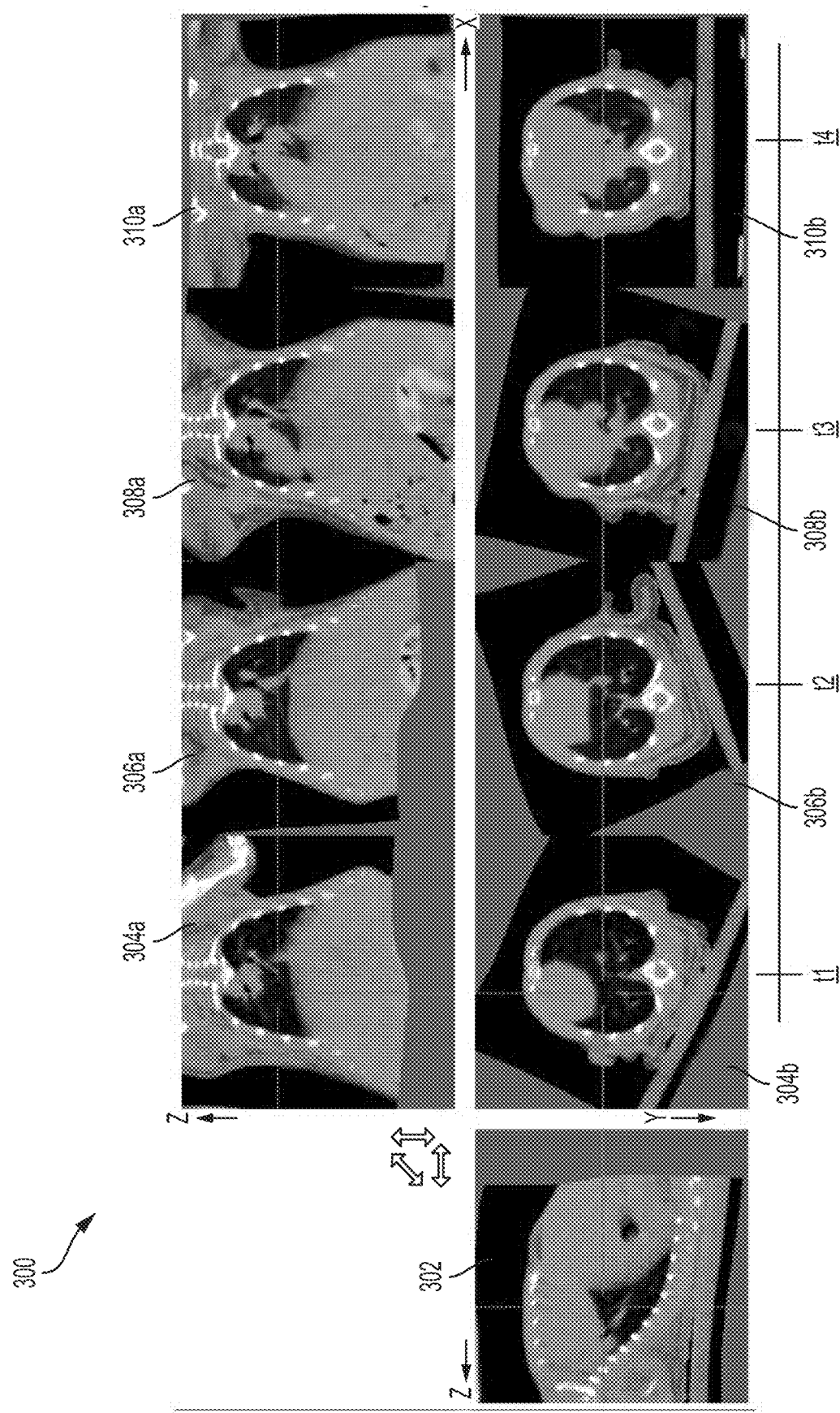
FIG. 3 is a series of images recorded at different times, wherein distortion correction and co-registration has been applied to the recorded images, according to an illustrative embodiment.

Turning to FIG. 3, in certain embodiments, co-registration is applied to a series of images (e.g. each image having been recorded at a different time point). Co-registration aligns multiple images such that the same physical location is represented by a single set of coordinates in each image. That is, for example, a given point P corresponding to a particular physical location in a subject's lungs is represented by a single set of coordinates $(x_0, y_0, z_0)$ in each image, as opposed to, e.g. being represented by a first set of coordinates $(x_1, y_1, z_1)$ in a first image and a second set of coordinates $(x_2, y_2, z_2)$ in a second image.

Coordinate values such as x-, y-, and z-coordinates are used throughout, but it should be understood that the specific coordinates (e.g. "x,y,z") used herein have no special significance in and of themselves, but are rather used for convenience in referring to particular directions and particular locations in an image, and do not impose any particular requirement of a coordinate system or approach for measuring distances in an image for use in the systems and methods described herein. For example, it is not necessary that a Cartesian coordinate system be used, and other coordinate systems, such as spherical or cylindrical systems, may be used to describe locations of particular points in an image.

In certain embodiments, the coordinate axes are defined based on the axes of image acquisition equipment used to record a given 3-D image. In certain embodiments, x-, y-, and z-coordinate axes are selected based on their alignment with particular directions with respect to the body of the subject.

For example, in certain embodiments, the x-coordinate axis is selected as the coordinate axis that is most closely aligned with a direction substantially across the body of a subject, from the left side of the subject to the right side of the subject, or vice versa (e.g. in the opposite direction). Accordingly, in certain embodiments, an x-direction corresponds to a direction proceeding substantially across the body of a subject, from the left side of the subject to the right side of the subject, or vice versa (e.g. in the opposite direction).

In certain embodiments, the y-coordinate axis is selected as the coordinate axis that is most closely aligned with a direction substantially from the front side (e.g. chest) to the backside (e.g. spine) of a subject, or vice versa (e.g. in the opposite direction). Accordingly, in certain embodiments, a y-direction corresponds to a direction proceeding from the front side (e.g. chest) to the backside (e.g. spine) of a subject, or vice versa (e.g. in the opposite direction).

In certain embodiments, the z-coordinate axis is selected as the coordinate axis that is most closely aligned with a direction substantially from the head to tail of a subject, or vice versa (e.g. in the opposite direction). Accordingly, in certain embodiments, a z-direction corresponds to a direction proceeding substantially from the head to tail of a subject, or vice versa (e.g. in the opposite direction).

In certain embodiments, a preliminary transformation (e.g. a preliminary rotation and translation transformation determined using principal axes of the identified backbone and/or principal axes of an identified breastbone in the graphical representation) step is carried out in order to align coordinate axes with particular directions along the subject, such as those described above. In certain embodiments, transformations determined using the artificial landmarks described herein align coordinate axes with particular directions along the subject, such as those described above.

FIG. 3 shows cross-sections 300 of a series of 3-D images collected at different time points, wherein distortion correction and co-registration has been applied to the different 3-D images recorded at different time points. Four cross-sections in an xz plane (e.g. slices in the xz plane) 304a, 306a, 308a, and 310a are shown along with cross-sections in an xy plane 304b, 306b, 308b, and 310b. A cross-section in the zy plane 302 is also shown for reference. Cross-sections 304a and 304b correspond to xz and xy planes, respectively, of an image recorded at a first time point, $t_1$. Cross-sections 306a and 306b correspond to xz and xy planes, respectively, of an image recorded at a second time point, $t_2$. Cross-sections 308a and 308b correspond to xz and xy planes, respectively, of an image recorded at a third time point, $t_3$. Cross-sections 310a and 310b correspond to xz and xy planes, respectively, of an image recorded at a fourth time point, $t_4$. Distortion correction and co-registration of images, as shown in FIG. 3 facilitates visualization of disease progression (e.g. tumor growth, fibrosis, edema) over time.

A. Registration of Images Via Artificial Landmarks

Figure 4:
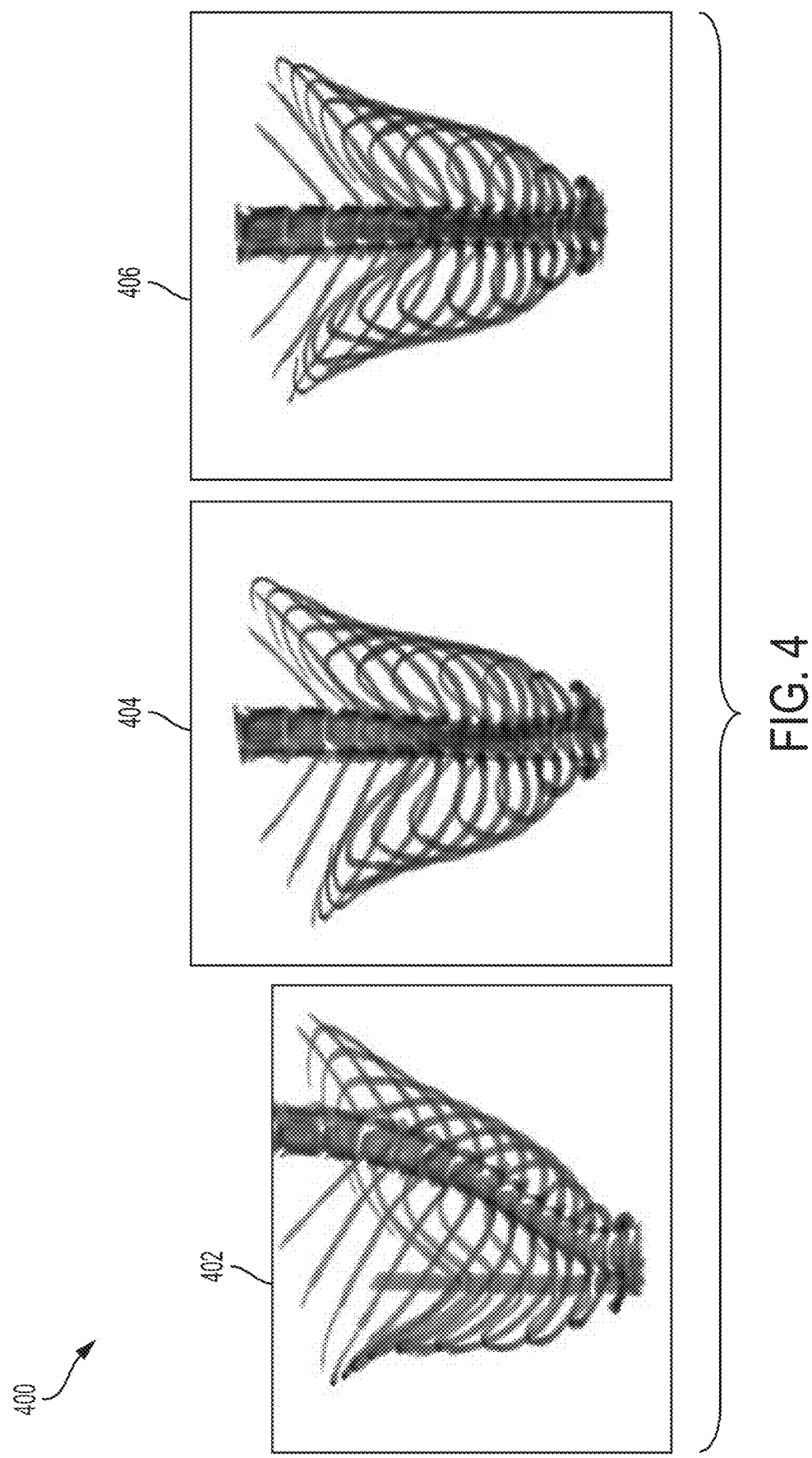
FIG. 4 is a set of images that shows the result of application of a linear transformation corresponding to a rotation and the result of application of a non-linear transformation corresponding to a distortion field correction, according to an illustrative embodiment.

Turning to FIG. 4, in certain embodiments, co-registration along with distortion correction is accomplished by applying a transformation comprising one or more linear and/or nonlinear operations to one or more images of a series of images. In certain embodiments, the transformation corresponds to a linear transformation comprising a translation and rotation. The linear transformation maintains the shape of objects as measured within the images, but corrects against arbitrary location and rotation of the images with respect to each other. In certain embodiments, other linear transformations may include a rigid transformation (e.g. a translation, e.g. a rotation), an affine transformation, and any combination thereof.

In certain embodiments, the transformation corresponds to a non-linear transformation, such as a regularized or smoothed extrapolation of distortion field, a thin-plate spline, or any transformation comprising an extrapolation operation and/or a smoothing operation. In certain embodiments the non-linear transformation comprises a distortion field correction. In certain embodiments, the non-linear transformation corrects against distortion (e.g. due to pose differences between the images). In certain embodiments, the non-linear transformation also provides fine co-registration of the series of images.

In certain embodiments, a linear transformation can also be used for distortion correction. In certain embodiments registration of an image comprises determining and applying a linear transformation as a preliminary step, which facilitates determination of a non-linear transformation.

FIG. 4 is a set of projections 400 showing representations of ribcage bones of a mouse identified in a 3-D image of the mouse. The set of projections 400 illustrates the application of, first, a linear transformation comprising a rotation and, second, a non-linear transformation corresponding to a distortion field, according to an illustrative embodiment. In FIG. 4, a first projection 402 shows ribcage bones of the mouse identified from a 3-D image as initially recorded. A second projection 404 shows the results of application of a linear transformation comprising a rotation to the 3-D image. Accordingly, the ribcage of the subject as shown in the second projection 404 is rotated with respect to the first projection 402. Finally, the result of application of a non-linear transformation for distortion correction is shown in a third projection 406.

Accordingly, in certain embodiments, in order to register an image to correct distortions within the image and/or co-register the image with another image, one or more transformations corresponding to linear and/or non-linear operations are determined and applied to the image. The systems and methods described herein provide for the determination of artificial landmarks from graphical representations of bones within an image.

In embodiments described herein, registration (e.g. comprising distortion correction and/or co-registration) of images is accomplished using artificially generated landmarks within the images. In general, landmarks (also referred to as markers, tags, or control points) correspond to specific points within an image that are identified as corresponding to a particular physical location of the subject that is imaged. The correspondence between landmarks and particular physical locations can be leveraged in order to determine appropriate transformations for distortion correction of a single image as well as distortion correction and/or co-registration of multiple images.

The artificial landmark-based registration approach described herein contrasts with previous approaches that accomplish co-registration by performing a cross-correlation that maximizes mutual information between two images (see, e.g., Maes et al., "Multimodality image registration by maximization of mutual information," *IEEE Transactions on Medical Imaging* 1997, 16 (2): 187-198). Such cross-correlation based approaches do not use landmarks of any kind, and work best if changes in the content of images are absent or marginal.

In contrast to "natural" landmarks, which correspond to naturally occurring, known distinguishable objects such as specific individual rib bones, specific joints, vertebrae and the like, artificial landmarks are determined from artificial objects (e.g. a given artificial landmark may be determined as a center of mass of a corresponding artificial object). Artificial objects correspond to fractions of real bones, that are generated in silico, via a series of morphological and logical operations applied to graphical representations of bones within images, as will be described in the following. Notably, while identification of natural objects within an image is sensitive to errors in image processing methods used to identify specific individual bones (e.g. segmentation), generation of artificial objects is robust to image segmentation errors and variations in image quality. Moreover, because artificial objects are generated via a series of morphological and logical operations, the density of such objects can be freely varied, which is advantageous to determining image registration transformations. Accordingly, artificial landmarks determined from artificial objects facilitate image registration.

In certain embodiments, artificial landmarks are used to determine a transformation used for image registration via a two-stage process.

In certain embodiments, a first stage comprises obtaining (e.g., determining or receiving) a set of target landmarks to be used along with the artificial landmarks in the image in order to determine the image registration transformation. Each target landmark is associated with a matching artificial landmark of the image, and comprises a set of target coordinates that represent a desired location of the matching artificial landmark. The set of target landmarks satisfies certain criteria, such that alignment of the artificial landmarks with the target coordinates yields a desired behavior of the artificial landmarks. For example, as described in the following, the set target landmarks may be symmetric (e.g. substantially invariant under a mirror operation), such that following alignment of the artificial landmarks with the target landmarks, the artificial landmarks are themselves symmetric.

In certain embodiments, in a second stage, an image registration transformation is determined using the target landmarks and the artificial landmarks in the given image. In particular, the image registration transformation is a transformation that, when applied to coordinates of the artificial landmarks in the given image, aligns the artificial landmarks with the target landmarks. In certain embodiments, in order to determine the image registration transformation, it is not necessary to obtain a target landmark for each and every artificial landmark within an image, and an image registration transformation can be determined using a subset of the artificial landmarks of the image and matching target landmarks.

Once determined, the image registration transform can be applied to other points of the image (e.g. not just points corresponding to the artificial landmarks), thereby registering the image. Depending on the target landmarks used to determine the image registration transformation, the image registration transformation may correct distortion in (e.g. symmetrize) the given image, and/or co-register the given image with one or more other images.

For example, an image registration transformation determined using a set of target landmarks that is symmetric, when applied to points of a given image will produce a symmetrized version of the given image, thereby correcting distortions in the image.

In certain embodiments, a single set of target landmarks is used to register multiple images. Registering multiple images to the same set of target landmarks co-registers the images. If the set of target landmarks is symmetric, then registration of each image using the target landmarks corrects distortions in each image (e.g. thereby producing symmetrized versions of each image) as well as co-registers the images.

A.i Obtaining Target Landmarks

Target landmarks can be obtained via multiple approaches. For example, in certain embodiments, a pre-existing set of target landmarks is obtained (e.g. accessed or retrieved from memory by a processor), and used for registration of one or more images.

In certain embodiments, a set of target landmarks is obtained using artificial landmarks within a given image. For example, a set of symmetric target landmarks, which can be used to correct distortion in one or more images, can be determined using artificial landmarks within a given image. In order to determine a set of symmetric target landmarks, a mirror operation (e.g. about a predetermined specific plane (e.g. a (e.g. a yz-plane)) is applied to the set of artificial landmarks within the given image, and locations of artificial landmarks before and after the mirror operation are compared (e.g. locations of the original artificial landmarks are compared with locations of the mirrored artificial landmarks). Comparing locations of the original artificial landmarks with locations of the mirrored artificial landmarks is used to determine, for each artificial landmark of at least a portion of the artificial landmarks, a set of target coordinates (e.g. a target landmark), such that the set of target landmarks (comprising the target landmarks determined for each artificial landmark) is symmetric.

Figure 5:
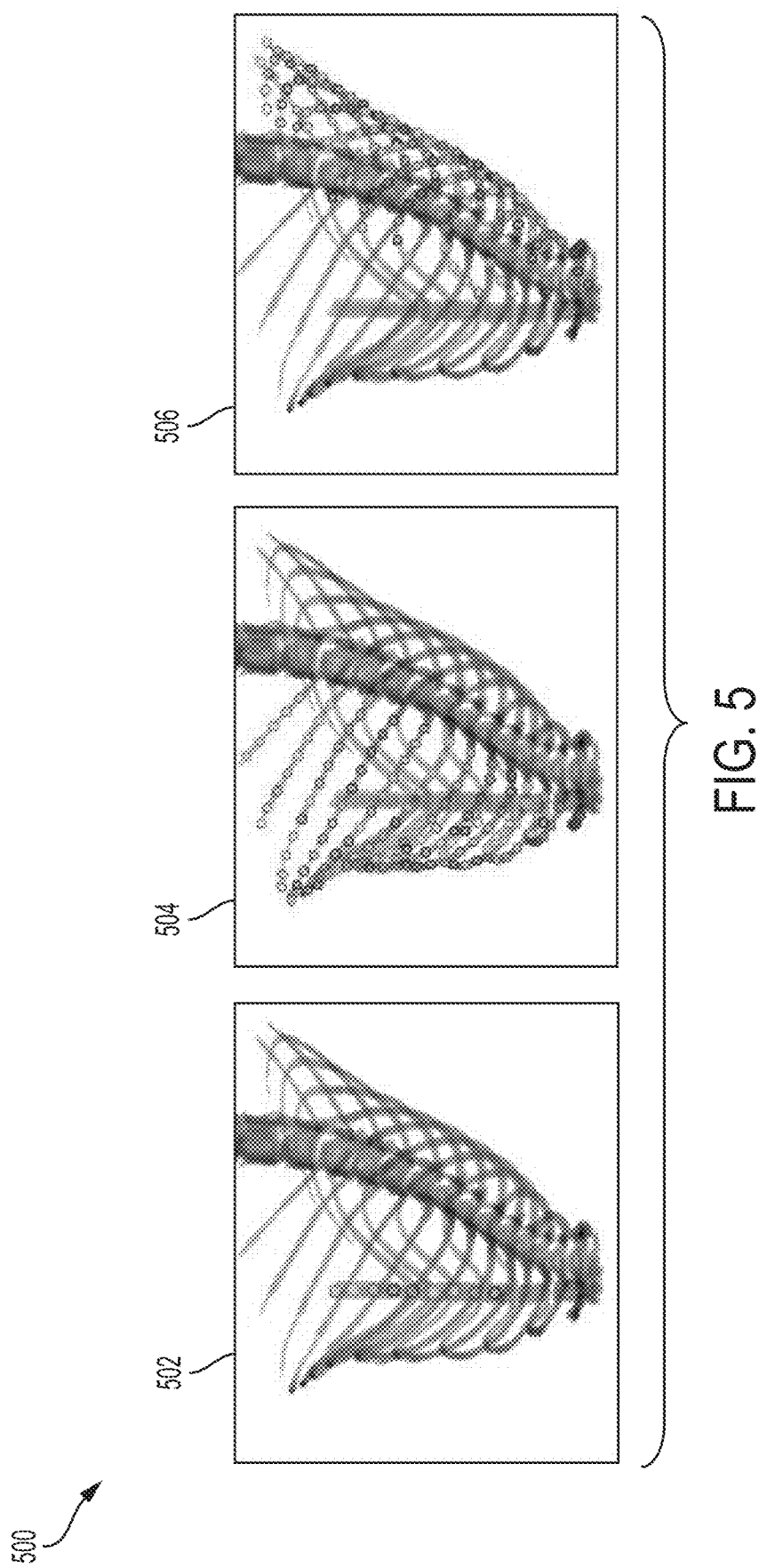
FIG. 5 is a set of images showing a series of automatically generated artificial landmarks along the breastbone, left rib bones, and right rib bones that are represented in the images, according to an illustrative embodiment.

For example, FIG. 5 shows a series of 2-D projections 500 of an image of a ribcage region of a mouse identifying different artificial landmarks generated along a breastbone (as shown in image 502), left ribs (as shown in image 504), and right ribs of a subject (e.g. a mouse) (as shown in image 506). In certain embodiments, locations of artificial landmarks along left rib bones and right rib bones are compared with mirrored locations of landmarks along left rib bones and right rib bones. A desired behavior in a distortion corrected (e.g. symmetrized) image is that for each artificial landmark on each rib bone, a location of the artificial landmark is approximately the same as a mirrored location of a matching opposite rib bone partner landmark on a matching opposite rib bone.

In particular, in the embodiments shown in FIG. 5, a chain of artificial landmarks is generated along each rib bone of the subject. Each rib bone artificial landmark thus corresponds to a particular physical location that is on a specific number rib bone (e.g. a first, second, third, etc. rib bone), on a specific side (e.g. a right side or a left side) of the subject, and is a specific distance along the specific rib bone (e.g.

proceeding outwards along the rib bone, away from the backbone of the subject). Accordingly, a given rib bone artificial landmark can be identified by a number and side of the specific rib bone on which it is generated, and an indication of its distance along the specific rib bone (e.g. a value corresponding to the distance; e.g. an index value that identifies its position in the chain along a the rib bone). For a given rib bone artificial landmark, the opposite rib bone partner to which it is matched is an artificial landmark determined to be approximately a same distance along a same number rib bone, but on the opposite side of the subject. Additional information, such as index values, can be associated (e.g. assigned) to artificial landmarks when they are generated, and used to facilitate the process of matching an artificial landmark to an opposite rib bone partner.

By matching rib bone artificial landmarks to opposite rib bone partner landmarks, a plurality of pairs of opposite rib bone artificial landmarks are identified, each pair comprising a rib bone artificial landmark and its opposite rib bone partner landmark. The identified pairs of opposite rib bone artificial landmarks can be used to determine coordinates of symmetrical target landmarks. For example, in certain embodiments, for each artificial landmark, coordinates of its target landmark are determined as the arithmetic average of the coordinates of the artificial landmark and mirrored coordinates of its opposite rib bone partner landmark. In particular, for a given artificial landmark having coordinates $(x_1, y_1, z_1)$ and a matching opposite rib bone partner landmark having mirrored coordinates $(x_2, y_2, z_2)$, the arithmetic average of the coordinates is determined as $((x_1+x_2)/2, (y_1+y_2)/2, (z_1+z_2)/2)$. Determining, for each artificial landmark, coordinates of target landmarks in this manner generates a set of symmetric target landmarks that can be used for distortion correction. In certain embodiments, prior to calculation of the arithmetic averages as described above, a rotation and translation transformation is applied as a preliminary step. In certain embodiments, the preliminary rotation and translation transformation is determined using principal axes of an identified backbone and/or principal axes of an identified breastbone. In certain embodiments, it is not necessary that a target landmark be generated for every rib bone artificial landmark in the image. In particular, in certain embodiments, for a given artificial landmark, it may not be possible to identify a matching opposite rib bone partner landmark. In certain embodiments, when, for a given artificial landmark, a matching opposite rib bone partner landmark is not identified, the given artificial landmark is discarded from the set of artificial landmarks, and not used in registration.

In certain embodiments, a target landmark is also determined for each (or at least a portion) of artificial landmarks along the breastbone. In particular, it is desired that breastbone landmarks remain constant upon mirroring of the image. Accordingly, for each breastbone artificial landmark, a corresponding target landmark is calculated as the arithmetic average of the landmark coordinates and its mirrored coordinates. In certain embodiments wherein a preliminary translation and rotation operation is determined and applied as described above with regard to rib bone artificial landmarks, the preliminary transformation is also applied to breastbone artificial landmarks (e.g., not only to artificial landmarks on rib bones).

A.ii Determining Image Registration Transformations

Once a set of target landmarks is obtained for use in registration of one or more images, an image registration transformation is determined for each of the one or more images using (i) the set of target landmarks and (ii) landmarks (e.g. artificial landmarks) of each of the one or more images. For a given image, the image registration transformation is determined to substantially optimize alignment of the set of artificial landmarks of the image with the set of target landmarks.

In certain embodiments, in order to determine a transformation that aligns a set of landmarks (e.g. artificial landmarks) of a given image with a set of target landmarks, there is a task to identify the specific target landmark to which the given landmark should be aligned. As will be described in the following, matching an artificial landmark to its adequate target landmark may be accomplished based on a comparison of index values associated with (e.g. assigned to) artificial landmarks and target landmarks, and/or coordinates of the artificial and target landmarks.

Once landmarks (e.g. artificial landmarks) are matched to target landmarks, a transformation that optimizes alignment of the landmarks with the target landmarks is determined.

Figure 6:
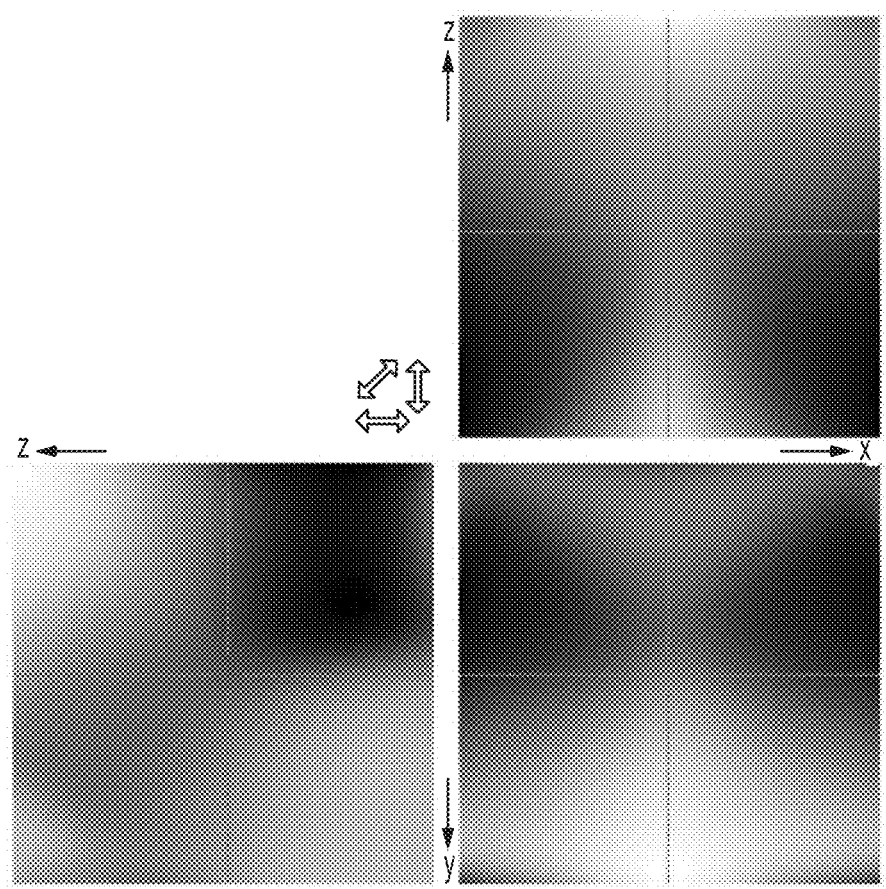
FIG. 6 is an intensity map showing a determined distortion correction function representing an x-component of the distortion field, as a function of image coordinates, according to an illustrative embodiment.

For example, in certain embodiments, the transformation is determined by determining, for each artificial landmark in the image, a measured dislocation. The measured dislocation for a given artificial landmark is determined as the difference between the coordinates that represent the original location of the given landmark and the coordinates of a corresponding target landmark. The transformation determined in this manner thus takes the form of a distortion field of three components (x-, y-, and z-components) each being a smooth function of image coordinates (x, y, and z). In certain embodiments, the distortion field is determined from measured dislocations between the artificial landmarks and their partner target landmarks, via extrapolation and a smoothing operation. FIG. 6 shows an example x-component of the distortion field as a function of image coordinates.

Figure 7:
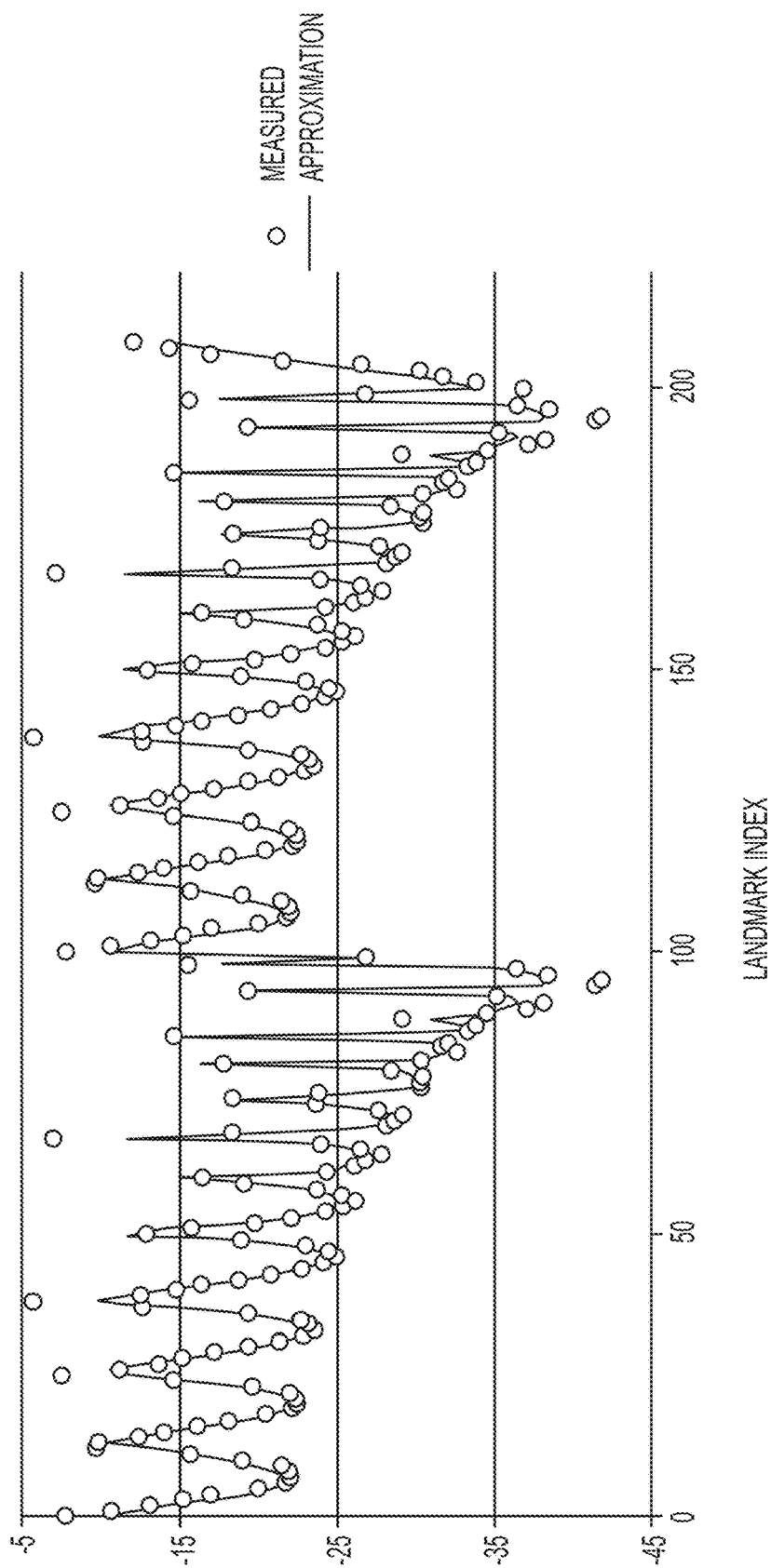
FIG. 7 is a graph showing measured and extrapolated values of a distortion correction function representing an x-component of the distortion field at locations of a plurality of artificial landmarks, according to an illustrative embodiment.

In certain embodiments, due to use of the smoothing operation, the value of the distortion field at locations of one or more particular artificial landmarks differ from the measured dislocations determined for each of the particular landmarks. FIG. 7 is a graph that shows, for each artificial landmark of an image, both the measured dislocation in the x coordinate as well as x-component of the determined distortion field at the location of the landmark. In certain embodiments, differences between the extrapolated and measured dislocations are used to estimate (lower limit of) accuracy of co-registration.

In certain embodiments, once determined, an image registration transformation can then be applied to points in a region of the image (e.g. not just points corresponding to the artificial landmarks) thereby producing a transformed image that is corrected for distortion (e.g. a symmetrized image) and/or co-registered with other images. Accordingly, while the transformation is determined via bone landmarks, it provides for distortion correction and/or co-registration over regions of the image comprising representations of soft tissue, thereby providing for the creation of distortion-free, symmetrized images of e.g. lungs and other soft tissue of a subject. Correcting distortion and/or co-registering images in this manner provides for symmetrical, standardized images that can readily be analyzed, interpreted, and/or compared with other images (e.g. previously recorded images, e.g. previously recorded images that were corrected for distortion similarly, e.g. co-registered images) in a direct fashion, without having to account for variations in pose and/or position of the subject.

In certain embodiments, a transformation determined via artificial bone landmarks in a first image recorded via a first imaging modality (e.g. microCT) is used for distortion correction in a second image recorded using a different modality (e.g. an optical imaging modality (e.g. FMT), e.g. PET). In certain embodiments, the first and second images are recorded at substantially the same time, with the subject in substantially the same pose and position, via a multimodal imaging system (e.g. a multimodal imaging system that combines microCT and PET imaging system, e.g. a multimodal imaging system that combines microCT with FMT imaging). In certain embodiments, the transformation that is determined from the artificial bone landmarks in the first image is applied to the second image. In certain embodiments, there is a known spatial relationship between the first and second image (e.g. due to a known different configuration of detectors and/or sources used to record the first and second images), and a modified, second transformation is determined from the transformation determined via the artificial landmarks in the first image. The second transformation is then applied to the second image in order to register the second image (e.g. correct distortion in the second image and/or co-register the second image with another image recorded via the second imaging modality).

B. Automated Generation of Artificial Landmarks

B.i Artificial Landmarks Along Rib Bones and the Breastbone

In certain embodiments, the systems and methods described herein provide for automated generation of artificial landmarks used for distortion correction and/or co-registration in the manner described above. Artificial landmarks generated via the approaches described herein are robust to errors in automated segmentation for identification of specific bones within an image, and can be refined via outlier filtering approaches.

In certain embodiments, a set of artificial landmarks within a given image is determined based on a set of artificial objects generated within the image. In certain embodiments, the image of the subject comprises a plurality of rib bones of the subject, and artificial objects are generated along each rib bone of the plurality of rib bones.

Figure 9:
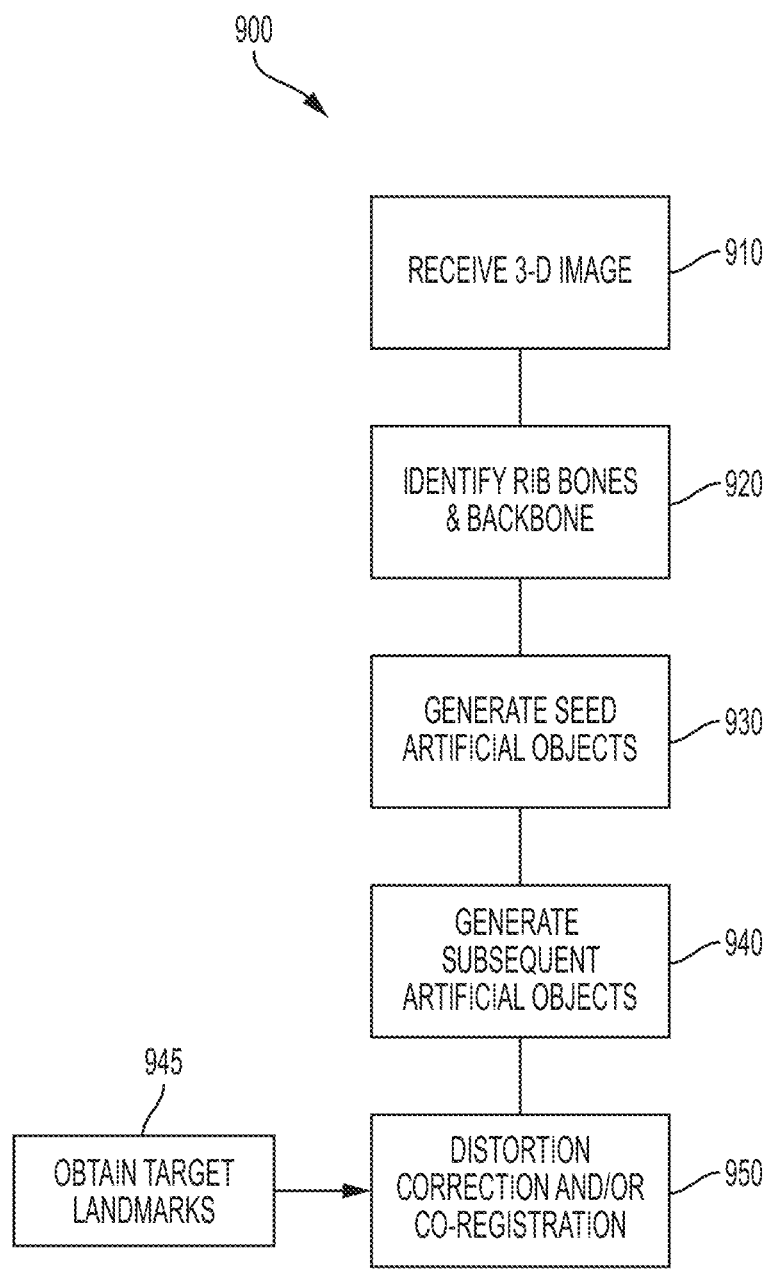
FIG. 9 is a block flow diagram of a process for correcting distortion in a single image or distortion correction and/or co-registration of multiple images using artificial landmarks along rib bones of a subject, according to an illustrative embodiment.

FIG. 9 is a block flow diagram that shows an example process 900 for generating artificial landmarks along rib bones in a 3-D image of a region of a subject for distortion correction and/or co-registration of multiple images. In certain embodiments, the process 900 begins with receiving a 3-D image of a region of the subject (910), wherein the received 3-D image comprises graphical representation of a plurality of rib bones (e.g. each rib bone of the subject's ribcage, e.g. a portion of the rib bones of the subject) as well as at least a portion of a backbone of the subject. Following receipt of the 3-D image, in a next step 920, rib bones and a backbone within the image are identified (920). Bones may be identified in a fully automated fashion (e.g. via segmentation), or, in certain embodiments, identification of bones may include a user interaction. For example, in certain embodiments bones within the image are automatically identified via a local threshold approach, after which the ribcage is automatically identified (see, e.g., Ollikainen and Kask, "Method and system for automated detection of tissue interior to mammalian ribcage from an in vivo image," U.S. Pat. No. 9,192,348), followed by the backbone. In certain embodiments, the 3-D image also comprises a breastbone, which is also identified.

After the rib bones and backbone of the subject are identified within the 3-D image, in another step 930 in the process 900 a plurality of seed rib bone artificial object are generated, each seed rib bone artificial object being within a first distance interval from the backbone in the graphical representation and corresponding to a region of a rib bone in the graphical representation.

In certain embodiments, seed rib bone artificial objects are generated by determining a backbone distance map comprising intensity (e.g. numeric) values at each of a plurality of points in three dimensions, each of the intensity values of the backbone distance map corresponding to a distance from a given point in 3-D space to the nearest point of the detected backbone in the image. A backbone distance interval mask is generated from the backbone distance map to identify points within the image whose distance to the backbone is within the first distance interval (e.g. the distance interval mask is a binary mask, wherein points having a distance to the backbone within the first distance interval are assigned a first value (e.g. a numeric 1, e.g. a Boolean true), and other points are assigned a second value (e.g. a numeric 0, e.g. a Boolean false)). Following generation of the backbone distance interval mask, a logical AND operation is applied between the backbone distance interval mask and a mask corresponding to the identified rib bones, resulting in the identification of a plurality of regions of the identified rib bones that are within the first distance interval from the backbone.

Figure 8:
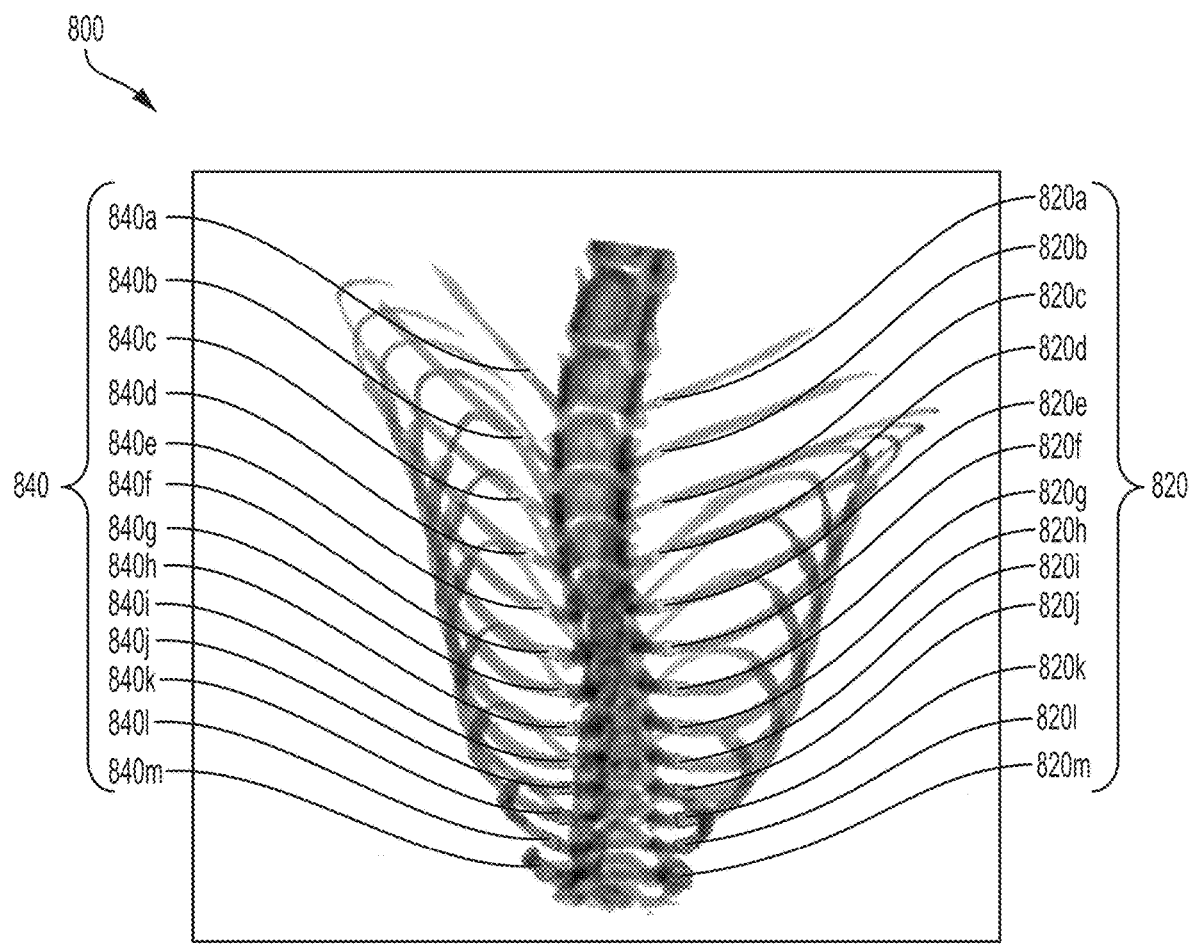
FIG. 8 is an image showing artificial objects generated along left and right rib bones, according to an illustrative embodiment.

FIG. 8 is an image showing artificial objects generated along left and right rib bones in the manner described above, according to an illustrative embodiment. The image shows thirteen seed rib bone artificial objects (840a, 840b, 840c, 840d, 840e, 840f, 840g, 840h, 840i, 840j, 840k, 8401, 840m; collectively 840) generated along left rib bones of the subject, and thirteen seed rib bone artificial objects (820a, 820b, 820c, 820d, 820e, 820f, 820g, 820h, 820i, 820j, 820k, 8201, 820m; collectively 820) generated along right rib bones of the subject.

In certain embodiments, separately identifying individual rib bones is not necessary in order to generate seed rib bone artificial objects. Instead, in certain embodiments, a bone mask, corresponding to a plurality of bones in the vicinity of the rib cage, is determined, from which a backbone and, optionally, a breastbone are identified and separated (e.g. resulting in determination of a breastbone mask and a backbone mask). The remaining bones of the identified correspond primarily to rib bones, but each individual rib bone need not be distinguished. Surprisingly, generation of seed rib bone objects is easier than separation and identification of individual rib bones.

In certain embodiments, following generation of the seed rib bone artificial objects (930), the process 900 continues with generation of subsequent rib bone artificial objects along rib bones in the image (940). In particular, for each automatically generated seed rib bone artificial object, a plurality of associated subsequent rib bone artificial objects are generated. In certain embodiments, each seed rib bone artificial object and the plurality of subsequent rib bone artificial objects forms a chain of rib bone artificial objects along each rib bone (e.g. the chain of rib bone artificial objects comprising the seed rib bone artificial objects and the subsequently generated rib bone artificial objects).

In certain embodiments for a given seed rib bone artificial object, the chain of rib bone artificial objects is generated in a stepwise fashion. In particular, beginning with the seed rib bone artificial object, a first subsequent rib bone artificial object is generated, a predefined distance (e.g. a Euclidean distance, e.g. a geodesic distance, along a mask corresponding to the identified rib bones) away from the seed rib bone artificial object, in a direction proceeding away from the identified backbone. A second subsequent rib bone artificial object is then generated, a predefined distance (e.g. a Euclidean distance, e.g. a geodesic distance, along a mask corresponding to the identified rib bones) away from the first subsequent rib bone artificial object, in a direction proceeding away from the identified backbone. In this manner, new rib bone artificial objects are generated in a stepwise fashion, each newly generated rib bone artificial object proceeding outwards away from the identified backbone. Morphological and logical operations similar to those used for generation of seed rib bone artificial object (e.g. determination of distance maps, thresholding operations, dilation operations, logical operations (e.g. AND, NOT), and combinations thereof) can be used for generation of subsequent rib bone artificial objects from each seed rib bone artificial object.

In certain embodiments, the distances separating each rib bone artificial object associated with a given seed rib bone artificial object (e.g. along a given rib bone) are all the same, such that an equidistant chain of artificial objects associated with the given seed rib bone artificial object is formed (e.g. along the given rib bone).

In certain embodiments, the process of generating new subsequent rib bone artificial objects in this manner proceeds until a newly generated rib bone artificial object is determined to be within a predefined threshold distance from an identified breastbone in the image.

Figure 11:
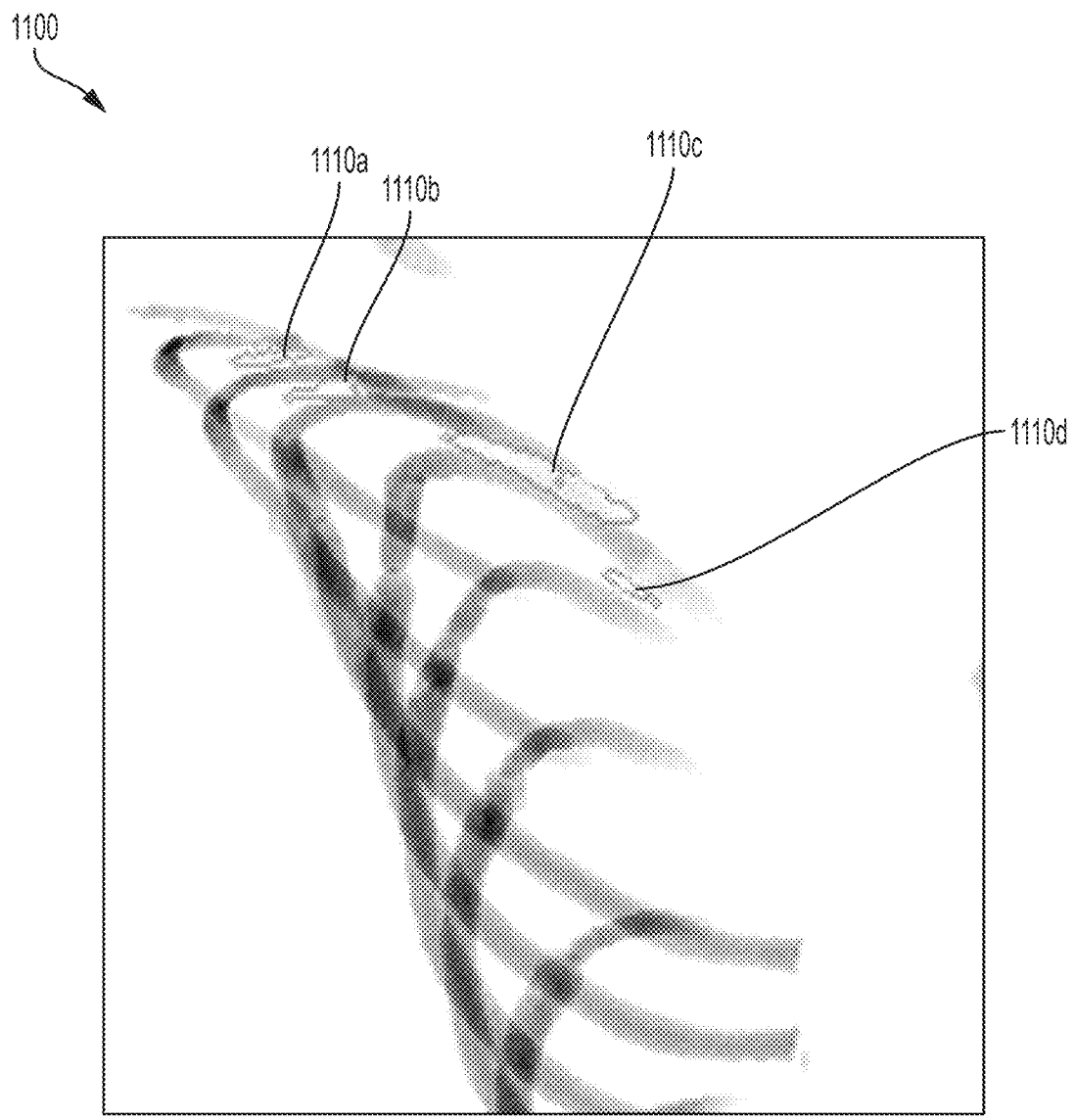
FIG. 11 is an image showing automatically detected dangerous regions of the image, wherein neighboring rib bones are close to each other, according to an illustrative embodiment.

In certain embodiments, additional steps in the process 900 are employed to ensure that, when subsequent rib bone artificial objects associated with a given seed rib bone artificial object are generated, rib bone artificial objects are not accidentally generated along a different rib bones (e.g. a rib bone corresponding to the seed rib bone artificial object and on a nearby rib bone). This may occur if, for example, in certain regions of the image one or more different rib bones are in close proximity to each other. In order to address this issue, in certain embodiments, the process 900 includes a step of automatically identifying with the image, one or more dangerous regions corresponding to regions in which a distance between a first and second rib bone in the graphical representation is below a predefined threshold distance. In certain embodiments, such dangerous regions can be identified without the need to separately identify individual rib bones (e.g. distinguish between different rib bones), for example, via the use of a morphological closing operation applied to a bone mask that identifies a plurality of rib bones in the graphical representation. An example image 1100 showing several identified dangerous regions 1110a, 1110b, 1110c, and 1110d is shown in FIG. 11.

Each time a new subsequent rib bone artificial object associated with a given seed rib bone artificial object is generated along a rib bone, the process determines whether the newly generated artificial object is within a predefined threshold distance from one or more previously identified dangerous regions. If the process determines that the newly generated rib bone artificial object is within the predefined threshold distance from a previously identified dangerous region, generation of subsequent rib bone artificial objects associated with the given seed rib bone artificial object is terminated.

In certain embodiments, addition to generation of artificial objects along rib bones within the image, artificial objects are automatically generated along an identified breastbone of the subject within the graphical representation in the image.

In particular, in certain embodiments, the graphical representation comprises at least a portion of the breastbone of the subject, the portion including the lower (e.g. tail-sided) end of the breastbone. In order to generate breastbone artificial objects the breastbone is identified within the graphical representation. The lower end of the breastbone is also identified within the graphical representation. Next, a seed breastbone artificial object is automatically generated, the seed breastbone artificial object corresponding to a region of the identified breastbone that is within a second distance interval from the identified lower end of the breastbone.

In certain embodiments, the seed breastbone artificial object is generated via a set of morphological and logical operations, in a manner similar to the approach for generation of the rib bone seed artificial objects. In particular, in certain embodiments, the lower end of the breastbone in the graphical representation is identified as point corresponding to a minimal z-coordinate of the identified breastbone in the graphical representation. The breastbone seed artificial object is then generated via morphological and logical operations (e.g. determination of a breastbone distance interval mask, followed by an AND operation) that identify a region of the identified breastbone that is within a predefined maximal distance from the point corresponding to the identified lower end of the breast bone (e.g. for each point of the seed breastbone artificial object, a distance (e.g. a Euclidean distance, e.g. a distance along a particular coordinate (e.g. a z-coordinate)) from the point to a point corresponding to the identified lower end of the breastbone is within the second distance interval).

In certain embodiments, a chain of subsequent breastbone artificial objects associated with the seed breastbone artificial object are generated by beginning with the seed breastbone artificial object and, in a stepwise fashion, generating new subsequent breastbone artificial objects, each newly generated breastbone artificial object proceeding upwards (e.g. a predefined distance from the previously generated breastbone artificial object), away from the lower end of the breastbone.

In certain embodiments, subsequent breastbone artificial objects are generated until a newly generated breastbone artificial object crosses an image border or reaches the other end of the identified breastbone, at which point generation of subsequent breastbone artificial objects is terminated. In certain embodiments, a predefined number of breastbone artificial objects is specified, and generation of subsequent breastbone artificial objects is terminated once the predefined number of breastbone artificial objects have been generated.

Accordingly, in certain embodiments, a set of artificial objects within an image can be generated in an automated fashion. In certain embodiments, the set of artificial objects within a given image comprises a plurality of artificial objects generated along graphical representations of rib bones within the image. In certain embodiments the set also comprises a plurality of artificial objects generated along an identified breastbone within the image. In certain embodiments, in order to provide for distortion correction and/or co-registration of multiple images in the manner described above, an artificial landmark is determined from each artificial object of the set. In certain embodiments, each artificial landmark is determined as the mass center of a corresponding artificial object.

In certain embodiments, once a set of artificial objects is determined for a given image, target landmarks are obtained (945) and the set of artificial objects can be used for distortion registration of the image (e.g., distortion correction and/or co-registration) as described previously (950).

In certain embodiments, additional information is associated with artificial objects and/or artificial landmarks that are determined therefrom. For example, a given seed rib bone artificial object can be associated with (e.g. assigned) a series of indices indicating whether it corresponds to a left or right side rib (e.g. a left-right index), as well as a number of a given rib bone to which it corresponds (e.g. a rib number index).

For example, in certain embodiments, a left-right index is associated with a seed rib bone artificial object based on an x-coordinate determined from the seed rib bone artificial object. The x-coordinate may be an average x-coordinate of points of the seed rib bone artificial object. In certain embodiments, prior to determining an x-coordinate from seed rib bone artificial objects for purposes of associating left-right index values to the artificial objects, a rotation and translation transformation is applied as a preliminary step. In certain embodiments, the preliminary rotation and translation transformation is applied to ensure that all left rib bones are located on a left side of the image, and all right rib bones are located on the right side of the image. In certain embodiments, the preliminary rotation and translation transformation is determined using principal axes of an identified backbone in the graphical representation and/or principal axes of an identified breastbone in the graphical representation.

Subsequent rib bone artificial objects may also be associated with indices, including a left-right index, a seed index, and a sequence index. As with seed rib bone artificial objects, a left-right index associated with a given subsequent rib bone artificial object identifies whether the given subsequent rib bone artificial object corresponds to a left or right side rib. A seed index associated with a given subsequent rib bone artificial object indicates the seed rib bone artificial object from which it was generated. In certain embodiments, wherein subsequent rib bone artificial objects are generated from a seed rib bone artificial as an ordered chain in a stepwise fashion as described above, the sequence index indicates the order in which the subsequent rib bone artificial object was generated.

Indexing of seed rib bone artificial objects and subsequent rib bone artificial objects may be applied during the generation process. In certain embodiments, indices of artificial objects are updated following one or more outlier filtering steps as described below, in order to reflect removal of artificial objects corresponding to outliers.

In certain embodiments, artificial landmarks determined from artificial objects are associated with indices in a similar fashion. A given artificial landmark determined from a corresponding artificial object may be associated (e.g. assigned) the same indices as those of the artificial object from which it is determined. In certain embodiments, an artificial landmark determined from an artificial object is associated with additional information characterizing the artificial object from which the artificial landmark was determined. For example, a given artificial landmark determined from a corresponding artificial object is associated with a value corresponding to a determined volume of the artificial object from which the artificial landmark was determined.

In certain embodiments, indices and additional information associated with artificial landmarks are used to facilitate matching of landmarks, e.g., to identify opposite rib bone partners or target landmarks, as described above.

In particular, in certain embodiments, rib bone artificial landmarks are matched to opposite rib bone partner landmarks to produce a symmetric set of target landmarks. Matching of artificial landmarks with their corresponding opposite rib bone partner landmarks may be accomplished by first matching seed rib bone artificial landmarks with corresponding opposite rib bone partner seed landmarks. A given seed landmark may be matched with a partner seed landmark on an opposite rib bone using index values, such as a left-right index and a rib number index, that are assigned to seed rib bone artificial landmarks. For example, in order to match a first seed artificial landmark to an opposite rib bone partner, a seed rib bone artificial landmark that has a different left-right index but a same rib number index is identified.

In certain embodiments, once seed rib bone artificial landmarks are matched with corresponding opposite rib bone partner seed landmarks on opposite side rib bones, subsequent rib bone artificial objects are matched with corresponding opposite rib bone partner landmarks based on their association with a particular seed rib bone artificial object from which they were generated (e.g. based on an associated seed index, e.g. based on an associated seed index and an associated left-right index), and their order in the sequence in which they were generated (e.g. based on an associated sequence index).

In another example, in order to determine an image registration transformation that aligns a set of artificial landmarks of a given image with a set of target landmarks, each artificial landmark of the given image is matched to a partner target landmark.

In particular, in certain embodiments, a set of target landmarks is determined using artificial landmarks of a first image, and used to for registration of a different, second image. In order to register the second image, each of at least a portion of the artificial landmarks in the second image is matched to its target landmark. In certain embodiments, like artificial landmarks, target landmarks are associated with index values, which can be used to facilitate matching between artificial landmarks and their partner target landmarks. A given target landmark may be assigned index values of an artificial landmark from which it is determined. For example, when each target landmark is determined from a particular artificial landmark of the first image, it is assigned the index values of the particular artificial landmark from which it was generated. Similarly, in certain embodiments, a target landmark determined from a particular artificial landmark may also be associated with additional information that is associated with the particular artificial landmark from which it was determined. Such additional information may include a volume of the artificial object from which the particular artificial landmark was determined. Accordingly, artificial landmarks of the second image can be matched to partner target landmarks using, alone or in combination: (i) index values, (ii) additional information, as well as (iii) coordinates of the artificial landmarks of the second image and the target landmarks.

In certain embodiments, artificial landmarks of the second image are matched to target landmarks by first matching seed rib bone artificial landmarks to target landmarks that were determined from seed rib bone artificial landmarks of the first image. Seed rib bone artificial landmarks in the second image may be matched to target landmarks using (i) z-coordinates of the artificial landmarks in the second image and the target landmarks and/or (ii) the indices (e.g. left-right indices, e.g. rib number indices) of the artificial landmarks in the second image and the indices of the target landmarks. Following matching of seed artificial landmarks with their target landmarks, subsequent rib bone artificial landmarks are matched with corresponding target landmarks based on their association with a particular seed rib bone artificial landmark from which they were generated (e.g.

based on an associated seed index, e.g. based on an associated seed index and an associated left-right index), and their order in the sequence in which they were generated (e.g. based on an associated sequence index).

B.ii Outlier Filtering for Rib Bone and Breastbone Artificial Objects

In certain embodiments, generation of artificial objects (e.g. rib bone artificial objects, e.g. breastbone artificial objects) comprises additional processing steps corresponding to filtering steps in order to ensure that the automatically generated artificial objects satisfy different sets of criteria.

For example, in certain embodiments, a volume filter is applied to eliminate one or more artificial objects corresponding to regions determined to represent a volume below a predefined threshold volume. This approach can be applied to eliminate artifacts during the generation of artificial objects, as shown, for example, in FIG. 12.

Figure 12:
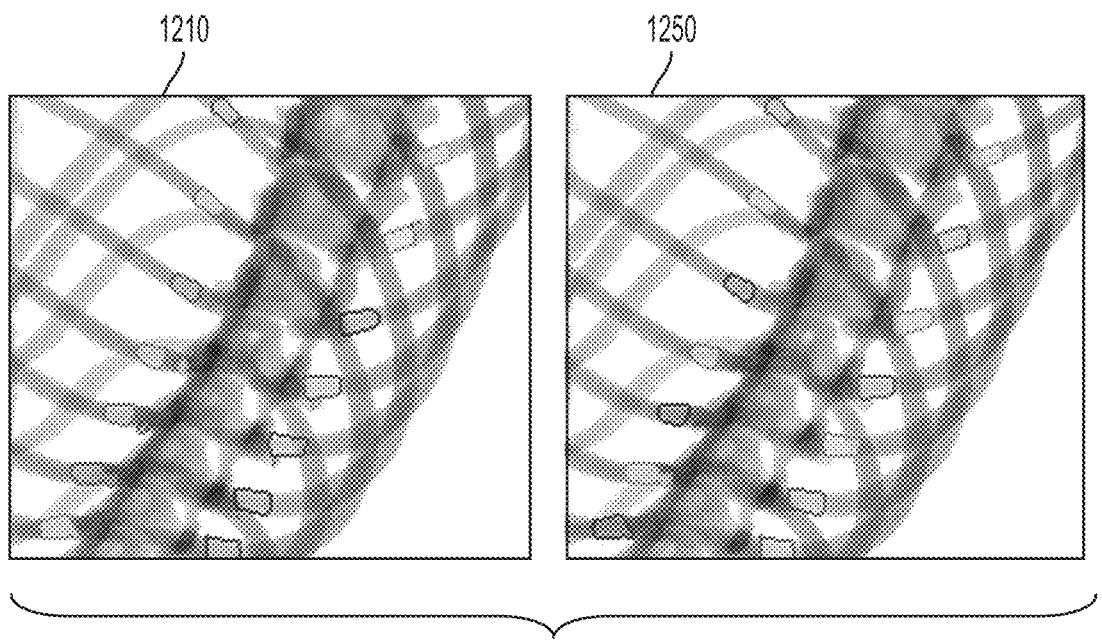
FIG. 12 is a set of two images showing artificial objects generated along a plurality of rib bones within the image before and after application of a volume filter, according to an illustrative embodiment.

A first image 1210 of FIG. 12 displays a graphical representation of a plurality of rib bones and a backbone, along with a prospective set of seed rib bone artificial objects generated by, for example, the process 900 described with respect to FIG. 9. As is evident in the image, in certain embodiments, a series of artificial objects with similar volumes is generated, along with several artificial objects having noticeably smaller volumes. These small volume artificial objects correspond to artifacts (e.g. resulting from noise in the image, e.g. resulting from errors in segmentation, e.g. resulting from the presence of physical, non-bone objects, such as grains of sand).

Accordingly, in order to eliminate such artifacts, and ensure that appropriate seed rib bone artificial objects are generated, following generation of the set of prospective seed rib bone artificial objects a volume filter is applied to the set of prospective seed rib bone artificial object. Application of the volume filter eliminates, from the set, those artificial objects determined to represent a volume below a predefined threshold volume. Following application of the volume filter, seed rib bone artificial objects are selected from the set of prospective seed rib bone artificial objects. A second image 1250 of FIG. 12 shows the results of applying a volume filter to the set of prospective seed rib bone artificial objects shown in the first image 1210. The set of artificial objects in the second image 1250 no longer includes the artificial objects corresponding to artifacts from the first image 1210.

In certain embodiments, a volume filter is applied to eliminate artifacts created during the generation of other artificial objects (e.g. any artificial objects, not just the seed rib bone artificial objects).

In certain embodiments, additional filtering criteria is applied to artificial objects generated along rib bones.

For example, in certain embodiments, a number of rib bones an imaged subject has is known. Accordingly, in certain embodiments, a number of seed rib bone artificial objects that has been generated is determined, and compared with a known (expected) number of rib bones that the imaged subject has. For example, mice have 13 rib bones on each side—13 left rib bones and 13 right rib bones—accordingly, 26 total rib bones. Accordingly, for an image of a mouse, it is expected that 13 left seed rib bone artificial objects and 13 right seed rib bone artificial objects will be generated. Therefore, by comparing the number of generated seed rib bone artificial objects with a known (expected) number of ribs that the subject has, erroneously generated artificial objects corresponding to artifacts can be identified and eliminated.

In certain embodiments, criteria for filtering out artifacts are established based on the symmetry of a physical ribcage, and applied to the set of rib bone artificial objects. In particular, in certain embodiments, in order to apply filtering approaches that leverage the symmetry of a physical ribcage, rib bone artificial objects are divided into left and right rib bone artificial objects, and grouped as pairs of corresponding left and right rib bone artificial objects. Pairs of artificial objects can be determined via a matching process similar to the process described above for matching artificial landmarks with opposite rib bone partner landmarks for purposes of distortion correction. In particular, pairs of corresponding artificial objects on opposite rib bones can be determined using indices associated with the artificial objects (e.g. a left-right index, e.g. a rib number index, e.g. a sequence index). In certain embodiments, coordinates associated with the artificial objects (e.g. an average x-coordinate of points of each artificial object; e.g. an average z-coordinate of points of each artificial object) as well as additional information, such as volumes of artificial objects is used to facilitate determining pairs of artificial objects on opposite rib bones.

Each pair of rib bone artificial objects thus comprises a first rib bone artificial object associated with a first rib bone (e.g. a right rib bone) of a pair of opposite rib bones and a second rib bone artificial object associated with a second rib bone (e.g. a left rib bone) of the pair of opposite rib bones. For each pair of rib bone artificial objects, the first and second rib bone artificial objects of a given pair should represent a similar volume and have similar heights. Height of an artificial object may be determined as a thickness in the z-direction of the artificial object, or as a distance along the backbone (e.g. determined as an average (mean) value of z-coordinates of points of the artificial object). Accordingly, in certain embodiments, a pair-wise comparison filter is applied that ensures, for each pair of rib bone artificial objects, (i) a difference between a volume represented by the first object of the pair and a volume represented by the second object of the pair is below a predefined threshold volume difference, and/or (ii) a difference between a height of the first object of the pair and a height of the second object of the pair is below a predefined threshold height difference.

In certain embodiments, the pair comparison filter is applied to remove artifacts during generation of seed rib bone artificial objects. For example, following generation of a set of prospective seed rib bone artificial objects (e.g. via the process 900 described above with respect to FIG. 9), one or more pairs of prospective seed rib bone artificial objects are automatically identified. Each pair comprises a first seed rib bone artificial object of a first rib bone of the pair of rib bones and corresponding second seed rib bone artificial object of the opposite rib bone (e.g. the first seed rib bone artificial object is along a right rib and the second seed rib bone artificial object is along the corresponding left rib).

A pair comparison filter is then applied to the set of prospective seed rib bone artificial objects, wherein application of the pair comparison filter eliminates, from the set, pairs of artificial objects for which (i) a difference between a volume represented by the first object of the pair and a volume represented by the second object of the pair is above a predefined threshold volume difference, and/or (ii) a difference between in a height of the first object of the pair and a height of the second object of the pair is above a predefined threshold height difference. Following application of the pair comparison filter, seed rib bone artificial objects are selected from the set of prospective seed rib bone artificial objects.

In certain embodiments, a pair comparison filter is applied to eliminate artifacts created during the generation of other artificial objects along rib bones (e.g. subsequent rib bone artificial objects, not just the seed rib bone artificial objects).

In certain embodiments, another filtering step is applied, comprising verifying whether the distance between consecutive seed rib bone artificial objects is consistent (along each rib/breastbone). For example, the distance (e.g. in the z-direction) between a given seed rib bone artificial object a next seed rib bone artificial object (e g immediately below and/or above, on the same side of the rib cage) is approximately constant (e.g. varies slowly) if seed rib bone artificial objects are correctly generated. Variations in the distance between adjacent seed rib bone artificial objects that are above a predefined threshold can be identified and used to filter outliers, for example if a seed rib bone artificial object is generated in a region outside of an actual rib bone.

In certain embodiments, a filtering approach based on comparison of artificial objects between multiple images is applied. In particular, in certain embodiments artificial objects of a first set of artificial objects within a first image are compared with artificial objects of a second set of artificial objects within a second image.

In certain embodiments, filtering based on comparison of artificial objects between multiple images comprises identifying a plurality of cross-image pairs of artificial objects, wherein each cross-image pair comprises a first artificial object of a first set of artificial objects of the first image and a corresponding second artificial object of a second set of artificial objects of the second image.

In certain embodiments cross image pairs of artificial objects are identified, automatically, using indices (e.g. left-right indices, e.g. rib number indices, e.g. seed indices, e.g. sequence indices) similar to the manner described above with respect to matching of artificial landmarks in a second image with target landmarks determined from artificial landmarks in a different, first image. In certain embodiments, identification of cross-image pairs of rib bone artificial objects comprises first identifying, for a given seed rib bone artificial object of the first image, a corresponding seed rib bone artificial object of the second image. In certain embodiments, indices (e.g. left-right indices, e.g. rib number indices) associated with seed rib bone artificial objects are used. In certain embodiments corresponding seed rib bone artificial objects can be determined by matching (e.g. searching for a closest match in) z-coordinates. In certain embodiments, there is an unknown shift in coordinates between the first and second image that is determined and corrected for before matching z-coordinates. The coordinate shift may be determined via a correlation technique. For example, a cross-correlation between a (i) a first set of points identifying positions of the artificial objects of the first image and (ii) a second set of points identifying artificial objects of the second image can be used to determine a shift in z-coordinates between the first and second images. The determined shift can then be used to correct for the shift when matching z-coordinates.

Once a given cross-image pair of seed rib bone artificial objects is identified, subsequent rib bone artificial objects associated with each seed rib bone artificial object of the cross-image pair of seed rib bone artificial objects are matched (e.g. using an order in which the subsequent rib bone artificial objects were generated, e.g. using a sequence index associate with each associated subsequent rib bone artificial object).

In certain embodiments, the corresponding first and second artificial objects of a given cross-image pair are compared to determine whether or not they represent similar volumes. Cross-image pairs for which the first and second artificial objects represent significantly different volumes are presumed to correspond to artifacts, and, accordingly eliminated. For example, in certain embodiments, for each cross-image pair of artificial objects, a difference between a volume of the first artificial object and a volume of the second artificial object is determined. For each cross-image pair, the determined volume difference is compared to a threshold difference (e.g. a predefined threshold difference), and, artificial objects of cross-image pairs for which the determined volume difference is above the threshold difference are eliminated from the respective set of artificial objects of each respective image.

In certain embodiments, for each of a first and second artificial object of a given cross image pair, information (e.g. values) about locations of the artificial objects with respect to neighboring artificial objects is determined, and compared. For example, for the first artificial object of the cross-image pair, values such as (i) a distance to a nearest neighboring artificial object, (ii) an average number of artificial objects within a predetermined threshold distance from the first artificial object, and the like, may be determined. The same values may be determined for the second artificial object, and compared with the corresponding values determined for the first artificial object. If differences between values (e.g. a distance to a certain other artificial object) is above a set threshold value, the artificial objects of the cross image pair are eliminated.

In certain embodiments, any of the above described filtering approaches (e.g. volume filter, pair comparison filter, consecutive object separation filter, cross-image pair comparison) are applied in combination, and in various orders. For example, for generation of the seed rib bone artificial objects shown in image 800 of FIG. 8, a volume filter, pair comparison filter, and consecutive object separation filter were applied. In certain embodiments, any of the above described filtering approaches (e.g. volume filter, pair comparison filter, consecutive object separation filter, cross-image pair comparison) are applied in combination with each other, as well as other filtering approaches, and in various orders.

In certain embodiments, any of the operations described herein as being performed on an identified volume is the same as an operation performed on a landmark (e.g. a coordinate) associated with the volume. Accordingly, operations such as the above described outlier filtering operations performed on artificial objects can also be performed on artificial landmarks associated with the artificial objects.

Performing particular operations, such as outlier filtering, on artificial landmarks can be advantageous from the standpoint of computational speed. In particular, while an object is represented by a mask in three dimensions, landmarks correspond points represented by coordinates. In certain embodiments, each landmark is associated with the artificial object from which it was determined. In certain embodiments, additional information is associated with a given landmark. The additional information associated with a given landmark includes information such as a volume of the object from which it is derived, indices such as a left-right index, a rib number index, a sequence index and the like. Accordingly, each artificial landmark is associated with information that can be used to perform the same outlier filtering steps described above on landmarks, as opposed to artificial object.

In certain embodiments, each artificial landmark is represented as a row in a table. Columns of the table correspond to properties of each landmark, such as an x-coordinate, a y-coordinate, a z-coordinate, as well as additional information such as a volume of an artificial object from which the landmark was determined, and various indices associated with the landmark. Operations on landmarks (each represented by a row in a table) are thus very fast compared to any operation applied to images because the number of voxels in an image may be many orders of magnitude bigger than the number of entries in a table of landmarks.

B.iii Artificial Landmarks Along Arbitrary Bones

In certain embodiments, artificial objects are generated along various different bones (e.g. not just rib bones and/or a breastbone of a subject) for distortion correction and/or co-registration.

Figure 10:
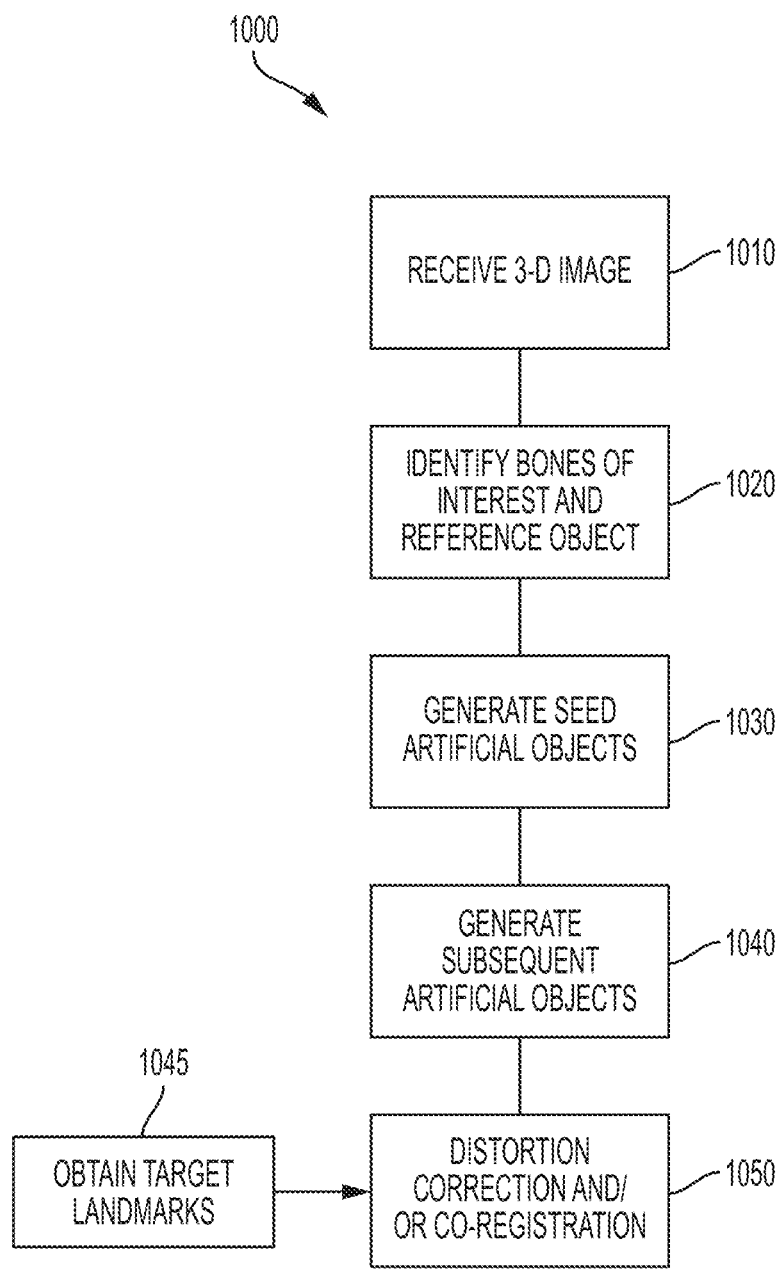
FIG. 10 is a block flow diagram of a process for correcting distortion in a single image or distortion correction and/or co-registration of multiple images using artificial landmarks along bones of a subject, according to an illustrative embodiment.

FIG. 10 shows a series of steps in an example process 1000 for generation of artificial objects along one or more bones of interest represented in a 3-D image of a region of a subject. In certain embodiments, the process 1000 begins with receiving a 3-D image of a region of the subject (1010), wherein the 3-D image comprises a graphical representation of one or more bones of interest. The bones of interest in the image can include bones of the subject's axial skeleton, such as rib bones, the breastbone, backbone, as well as other types of bones, from other portions of the skeleton of the subject.

Following receipt of the 3-D image, in a next step 1020, one or more bones of interest are identified (e.g. automatically (e.g. via segmentation, e.g. via a local threshold approach), e.g. via a user interaction) within the image. In addition, a reference object within the image is also identified (1020). The reference object may be a single point of the image, a 1-D line, a 2-D surface, or a 3-D region of the image. For example, in certain embodiments, a centerline of a particular bone or portion of a bone is identified within the image and used as a reference object. In certain embodiments, a 2-D surface of a bone identified within the image is used as a reference object.

The reference object identified within the image is used as a basis for generating seed artificial objects along each of the bones of interest. In particular, in certain embodiments, at step 1030 the process 1000 automatically generates, one or more seed artificial objects corresponding to a regions of the identified bones of interest that are within a specific distance interval from the reference object.

In certain embodiments, seed artificial objects are generated by first determining a distance map comprising intensity values (e.g. numeric values) at each of a plurality of points in three dimensions. Each of the intensity values at each point corresponds to a distance from the given point to the reference object. The distance map is then used to generate a distance interval mask that identifies those points in 3-D space that are within a specific distance interval from the reference object (e.g. the distance interval mask is a binary mask, wherein points having a distance to the reference object within a predefined distance interval are assigned a first value (e.g. a numeric 1, e.g. a Boolean true), and other points are assigned a second value (e.g. a numeric 0, e.g. a Boolean false)).

The distance interval mask can then be used to identify regions of the one or more bones of interest that are within a specific distance from the reference object. In certain embodiments, the distance interval mask is used in combination with a mask that identifies the one or more bones of interest. A logical AND operation is applied (e.g. in a pointwise fashion) between the distance interval mask and the mask corresponding to the identified one or more bones of interest, thereby automatically identifying regions of the bones of interest that are within the distance interval from the reference object.

In certain embodiments, following generation of the seed artificial objects (1030), the process 1000 continues with generation of subsequent artificial objects associated with each seed artificial object (1040). In particular, beginning with a given seed artificial object corresponding to a region of a bone of interest, a plurality of associated subsequent rib bone artificial objects are automatically generated along the bone of interest. In certain embodiments, the artificial objects generated along a bone of interest (e.g. the seed artificial object and the subsequent artificial objects) form a chain of artificial objects along the bone of interest.

In certain embodiments, for a given seed artificial object, the associated subsequent artificial objects are generated in a stepwise fashion. For example, beginning with the seed artificial object, a first subsequent artificial object is generated along a bone of interest, a predefined distance away from the seed artificial object, in a direction proceeding away from the identified reference object. A second subsequent artificial object is then generated along the bone of interest, a predefined distance away from the first subsequent artificial object, in a direction proceeding away from the identified reference object. In this manner, new artificial objects are generated in a stepwise fashion, each newly generated artificial object proceeding outwards away from the identified reference object and along the bone of interest.

In certain embodiments, the distances separating each artificial object along a given bone of interest are all the same, such that an equidistant chain of artificial objects is formed along the bone of interest.

In certain embodiments, a set of morphological and logical operations are used for generation of subsequent artificial object along each bone of interest.

In certain embodiments, the process 1000 includes steps to ensure that subsequent artificial objects generated from a specific seed artificial object corresponding to a region of a bone of interest are accurately generated along that bone of interest, and not generated along other bones identified in the image (e.g. the automated processing does not cause subsequent artificial objects to jump to other bones). Accordingly, the process of generating new subsequent artificial objects may proceed until a newly generated artificial object is determined to be within a predefined threshold distance from an identified additional bone (e.g. not corresponding to one of the one or more identified bones of interest) within the image. When a newly generated artificial object is determined to be within a threshold distance of the additional bone, generation of artificial objects along the particular bone of interest is terminated.

In certain embodiments, additional steps in the process 1000 are employed to ensure that, when subsequent artificial objects associated with a given seed artificial object are generated, artificial objects are not accidentally generated along a multiple different bones of interest (e.g. a bone of interest on which the seed artificial object is generated and then on a nearby bone of interest). This may occur if, for example, in certain regions of the image one or more different bones of interest are in close proximity to each other. In order to address this issue, in certain embodiments, the process 1000 includes a step of automatically identifying, with the image, one or more dangerous regions corresponding to regions in which a distance between a first and second bone of interest is below a predefined threshold distance.

Each time a new subsequent artificial object associated with a given seed artificial object is generated, the process determines whether the newly generated artificial object is within a predefined threshold distance from one or more previously identified dangerous regions. If the process determines that the newly generated artificial object is within the predefined threshold distance from a previously identified dangerous region, generation of subsequent artificial objects associated with the given seed artificial object is terminated.

Accordingly, in certain embodiments, a set of artificial objects within an image can be generated in an automated fashion. In certain embodiments, the set of artificial objects within a given image comprises a plurality of artificial objects generated along each identified bone of interest within the image.

In certain embodiments, in order to provide for distortion correction and/or co-registration of multiple images in the manner described above, an artificial landmark is determined from each artificial object of the set. In certain embodiments, each artificial landmarks is determined as the mass center of a corresponding artificial object.

In certain embodiments, once a set of artificial objects is determined for a given image, target landmarks are obtained (1045) and the set of artificial objects can be used for distortion registration of the image (e.g., distortion correction and/or co-registration) as described previously (1050).

B.iv Outlier Filtering for Artificial Objects Generated Along Arbitrary Bones of Interest In certain embodiments, similar to the approach described for generation of artificial objects along rib bones and/or a breastbone of a subject, generation of artificial objects along various bones of interest comprises additional processing steps corresponding to filtering steps in order to ensure that the automatically generated artificial objects satisfy different sets of criteria.

For example, a volume filter can be applied in a general manner, each time one or more artificial objects (seed artificial objects, as well as subsequent artificial objects) are generated, in order to eliminate one or more artificial objects corresponding to regions determined to represent a volume below a predefined threshold volume. Excessively small artificial objects, which are identified and eliminated via application of the volume filter, often correspond to artifacts as a result of errors in image segmentation and/or noise.

In certain embodiments, generation of one or more artificial objects includes a first step of generation of a set of prospective artificial objects. Such prospective artificial objects may be generated via any of the approaches described herein (e.g. via a logical AND operation between determined masks). In certain cases, this set of prospective artificial objects includes extremely small artificial objects, that correspond to artifacts that result from noise and/or image segmentation errors. In order to eliminate such artifacts, a volume filter is applied to eliminate, from the set, those artificial objects determined, by the processor, to represent a volume below a predefined threshold volume. Following application of the volume filter, each of the desired artificial object(s) (e.g. each seed artificial object, e.g. a newly generated subsequent artificial object associated with a given seed artificial object) is(are) selected from the set (from which the volume filter has eliminated excessively small artificial objects).

In certain embodiments, other filters that leverage physical intuition, such as a symmetry of particular skeletal regions, may also be applied. In certain embodiments, another filtering step is applied, comprising verifying whether the distance between consecutive artificial objects is consistent.

In certain embodiments, a filtering approach based on comparison of artificial objects between multiple images, based on comparing cross-image pairs is applied as described above.

In certain embodiments, filtering approaches, including, but not limited to those described above (e.g. volume filter, pair comparison filter, consecutive object separation filter, cross-image pair comparison, filtering approaches based on symmetry of particular skeletal regions) are applied in combination, and in various orders.

C. Examples

Figure 15:
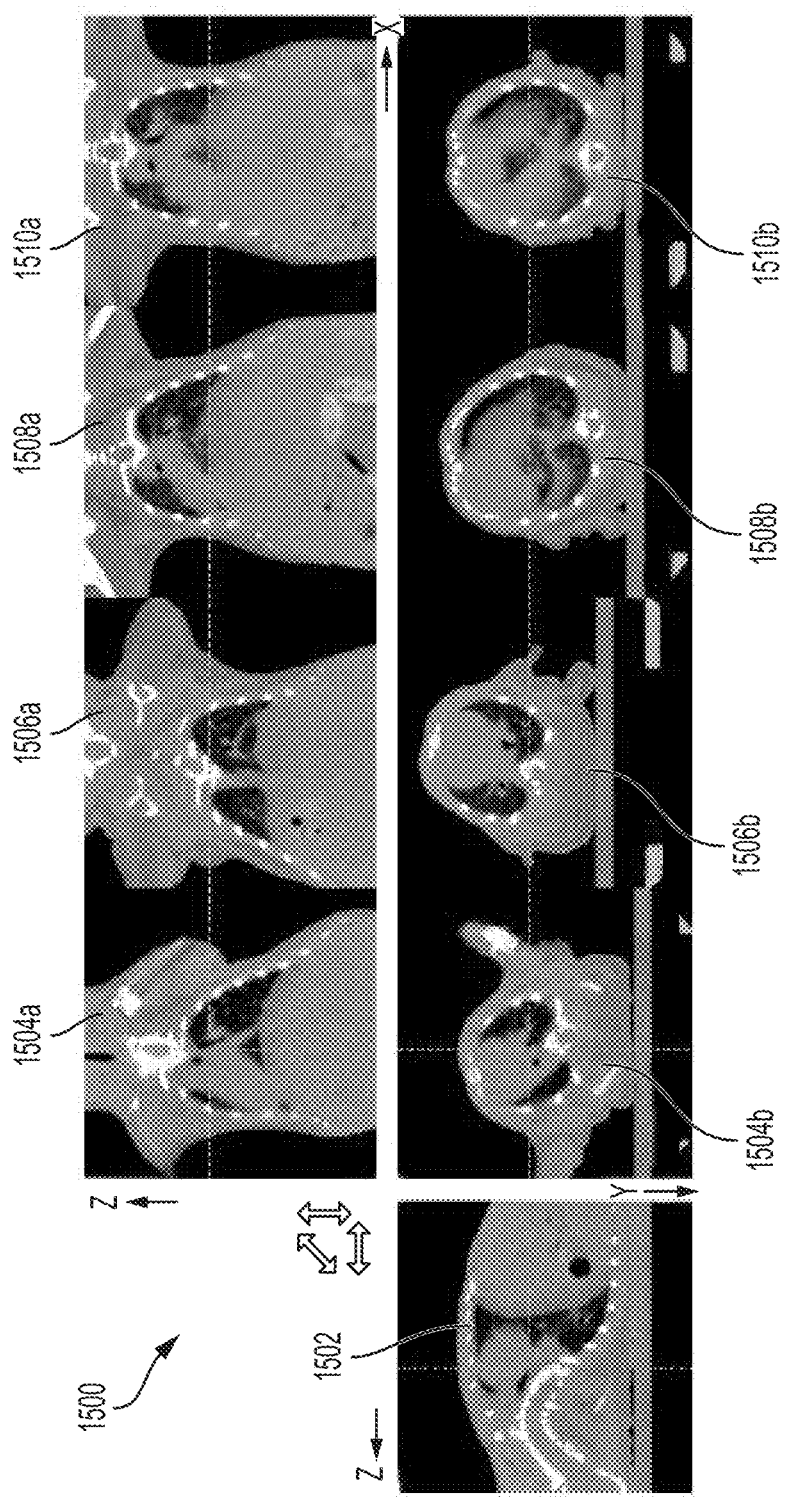
FIG. 15 is a series of images recorded at different times, wherein no registration (e.g. no distortion correction, no co-registration) has been applied to the recorded images, according to an illustrative embodiment.

FIGS. 15-18 show examples of image registration using the artificial landmark generation approach described herein. FIG. 15 shows cross sections 1500 of a series of 3-D images of a mouse collected at different time points, without registration. Cross-sections (planes) of four different images are shown, wherein for each image the position and pose of the mouse (subject) are different. Four cross-sections in an xz plane (e.g. slices in the xz plane) 1504a, 1506a, 1508a, and 1510a are shown along with cross-sections in an xy plane 1504b, 1506b, 1508b, and 1510b. A cross-section in the zy plane 1502 is shown for reference. Cross-sections 1504a and 1504b correspond to slices through xz and xy planes, respectively, of a first image recorded at a first time point. Cross-sections 1506a and 1506b slices through xz and xy planes, respectively, of an second image recorded at a second time point. Cross-sections 1508a and 1508b correspond to xz and xy planes, respectively, of a third image recorded at a third time point. Cross-sections 1510a and 1510b correspond xz and xy planes, respectively, of a fourth image recorded at a fourth time point. The images in FIG. 15 correspond to raw images, without any distortion correction or co-registration applied. Differences in the pose and position of the mouse in the different measurements are reflected in the images, as shown in the 2-D cross sections of the figure.

Figure 16:
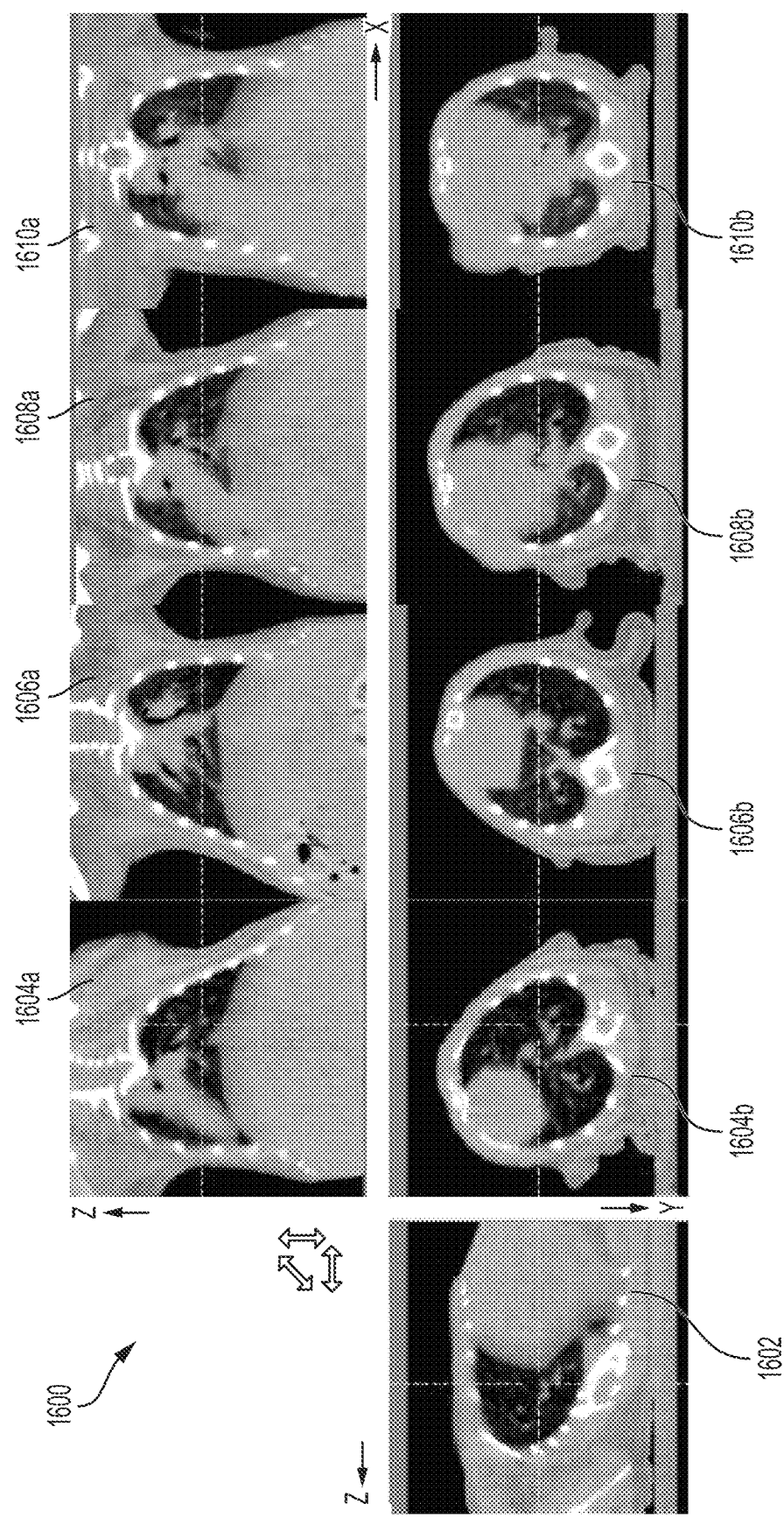
FIG. 16 is a series of images recorded at different times, wherein a transformation corresponding to a translation operation has been applied to each image, according to an illustrative embodiment.

FIG. 16 shows an example of determining transformations corresponding to translation operations and applying the transformations to the 3-D images. In order to determine the transformations, artificial landmarks were generated for each image in a series of images using the approach described herein. A set of target landmarks was determined using the artificial landmarks in one of the images. The target landmarks were determined to be symmetrical under a mirror operation about a yz-plane. For each image in the series, a corresponding transformation corresponding to a translation operation was determined to align the set of artificial landmarks in the respective image with the set of target landmarks.

The determined translation operation was applied to each corresponding image, and the results are shown in the cross-sections 1600 shown in FIG. 16. Analogous to FIG. 15, cross-sections 1604a and 1604b correspond to xz and xy planes, respectively, of a first image corresponding to a first measurement recorded at a first time point. Cross-sections 1606a and 1606b correspond to xz and xy planes, respectively, of a second image recorded at a second time point. Cross-sections 1608a and 1608b correspond to xz and xy planes, respectively, of a third image recorded at a third time point. 1610a and 1610b correspond to xz and xy planes, respectively, of a fourth image corresponding to a fourth measurement. A cross-section in the yz plane 1602 is also shown. As a result of application of a determined translation operation to each image in the series, a mean coordinate of artificial landmarks of each image is the same for all four images. Where correction is needed for rotation of the subject with respect to the axes of the image acquisition instrument, the transformation approach of either FIG. 17 or FIG. 18 may be superior.

Figure 17:
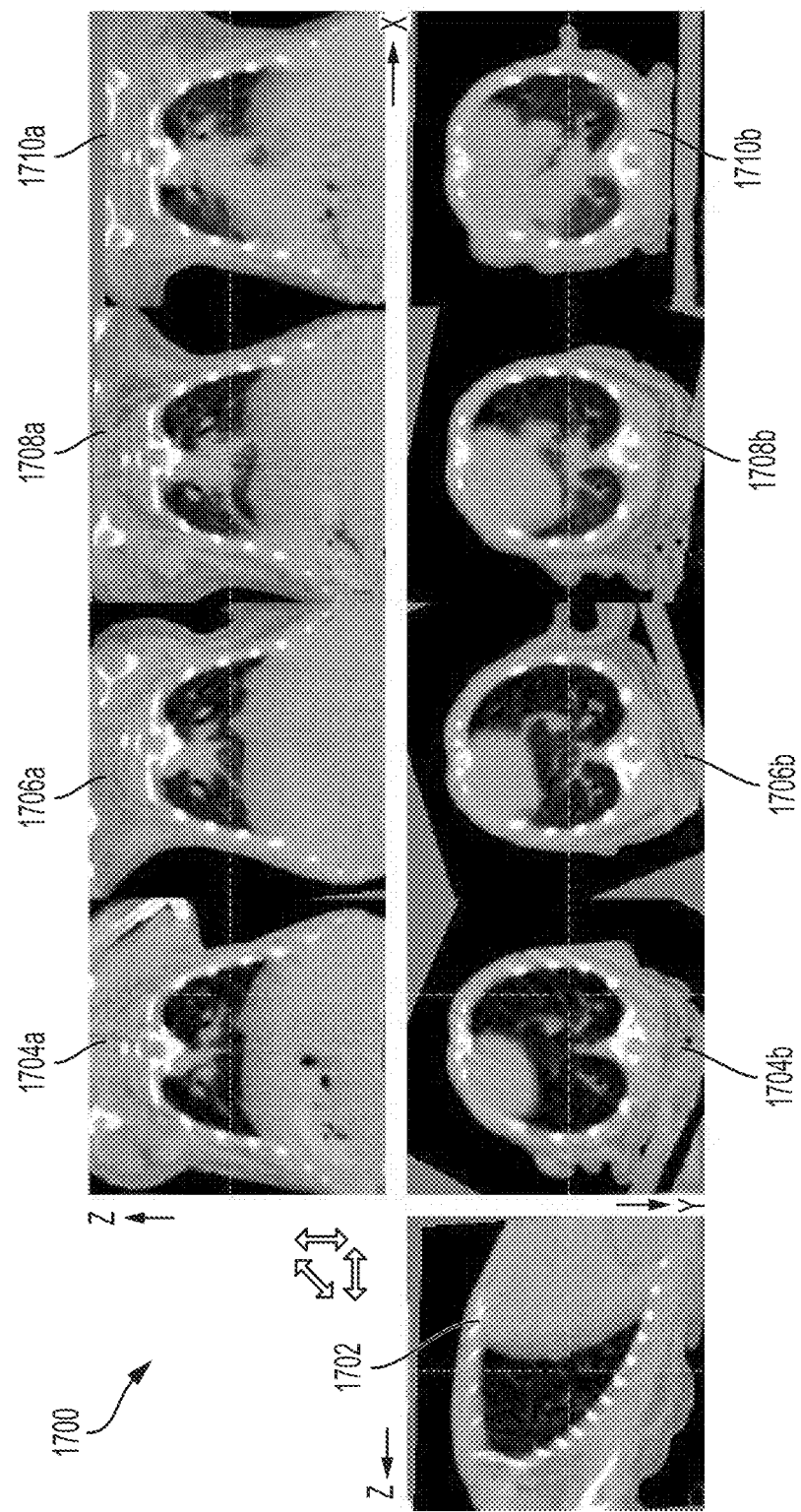
FIG. 17 is a series of images recorded at different times, wherein a linear transformation has been applied to each image, according to an illustrative embodiment.

FIG. 17 shows an example wherein for each image in the series of four images, a transformation corresponding to a linear transformation was determined using artificial landmarks in the image, and applied to the image. Artificial landmarks were generated for each image in the series, and symmetrical target landmarks were determined using one of the images in the series as previously described. For each image, a corresponding linear transformation was determined using the artificial landmarks in the respective image and the target landmarks (e.g. the linear transformation was determined to substantially optimize alignment of the set of artificial landmarks of a given image with the set of target landmarks).

The results of application of, for each image, the corresponding determined linear transformation to the image, are shown in the series of cross-sections 1700 shown in FIG. 17. Analogous to FIGS. 15 and 16, cross-sections 1704a and 1704b correspond to xz and xy planes, respectively, of a first image recorded at a first time point. Cross-sections 1706a and 1706b correspond to xz and xy planes, respectively, of an second image recorded at a second time point. Cross-sections 1708a and 1708b correspond to xz and xy planes, respectively, of a third image recorded at third time point. Cross-sections 1710a and 1710b correspond to xz and xy planes, respectively, of a fourth image corresponding to a fourth measurement. A cross-section in the yz plane 1702 is also shown.

Figure 18:
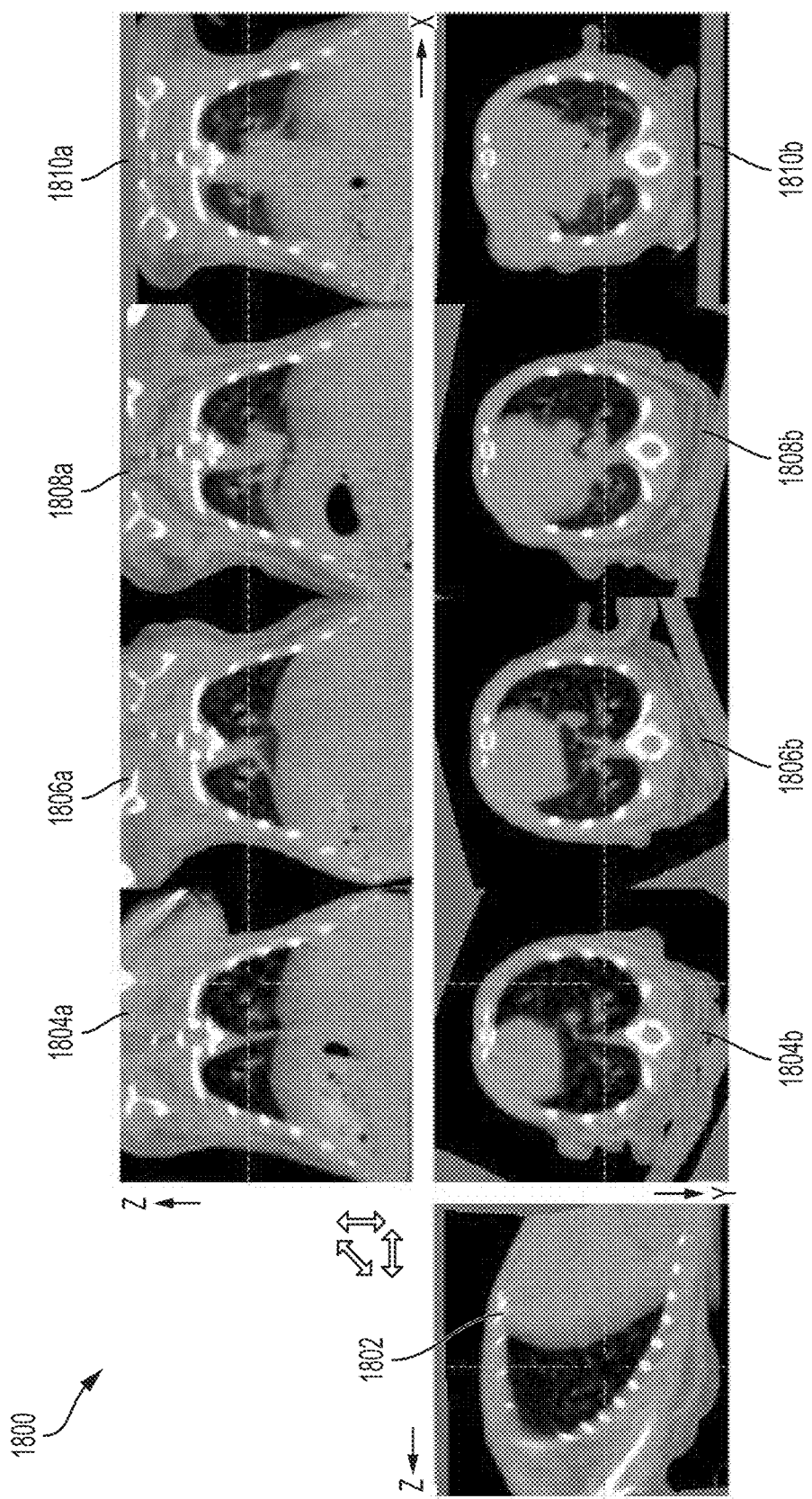
FIG. 18 is a series of images recorded at different times, wherein a transformation comprising a linear operation followed by a non-linear operation has been applied to each image, according to an illustrative embodiment.

FIG. 18 shows an example wherein for each image in the series of four images, a transformation comprising a linear transformation followed by a non-linear transformation was determined using artificial landmarks in the image, and applied to the image. Artificial landmarks were generated for each image in the series, and symmetrical target landmarks were determined using one of the images in the series as previously described. For each image, a combined transformation (corresponding to a linear transformation followed by a non-linear transformation) was determined using the artificial landmarks in the respective image and the target landmarks (e.g. transformation was determined to substantially optimize alignment of the set of artificial landmarks of a given image with the set of target landmarks).

The results of application of, for each image, the corresponding determined transformation (linear transformation followed by a non-linear transformation) to the image, are shown in the series of cross sections 1800 shown in FIG. 18. Analogous to FIGS. 15-17, cross-sections 1804a and 1804b correspond to xz and xy planes, respectively, of a first image recorded at a first time point. Cross-sections 1806a and 1806b correspond to xz and xy planes, respectively, of an second image recorded at a second time point. Cross-sections 1808a and 1808b correspond to xz and xy planes, respectively, of a third image recorded at a third time-point. Cross-sections 1810a and 1810b correspond to xz and xy planes, respectively, of a fourth image recorded at a fourth time point. A cross-section in the yz plane 1802 is also shown.

Figure 19:
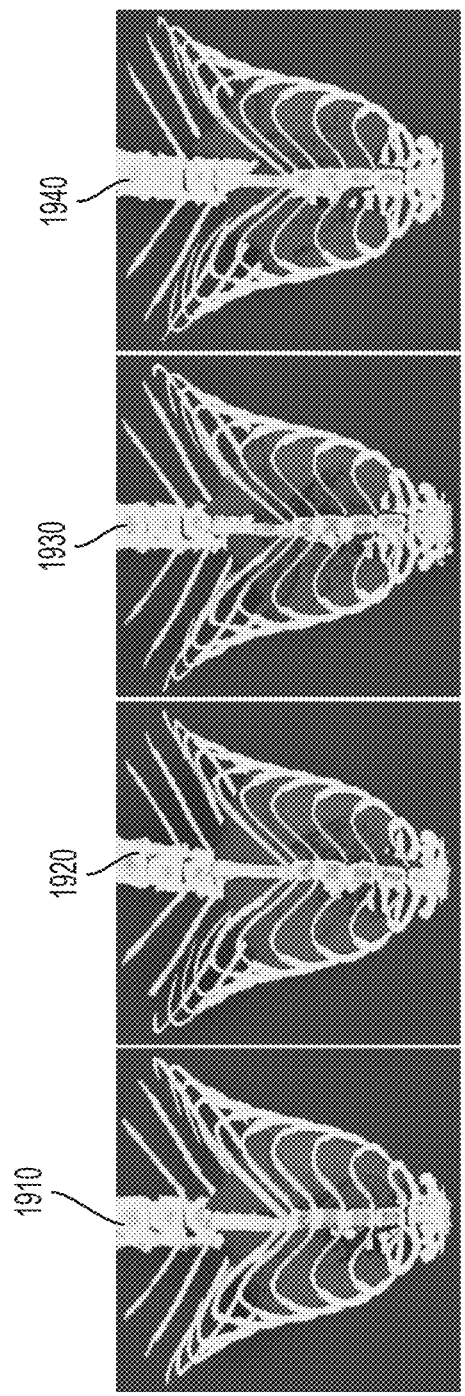
FIG. 19 is a series of images showing graphical representations of bones and aerated regions of lungs of a subject following non-linear registration of images, according to an illustrative embodiment.

FIG. 19 shows a series of projections 1910, 1920, 1930, 1940 of identified ribcage bones (e.g. a bone mask) and identified aerated lungs, each projection representing ribcage bones and aerated lungs identified within a different 3-D image of a mouse, recorded at a different time. The different 3-D images have been co-registered, and, accordingly, can readily be compared to observe variations in the subject's lungs.

D. Network Environment and Computing System

Figure 13:
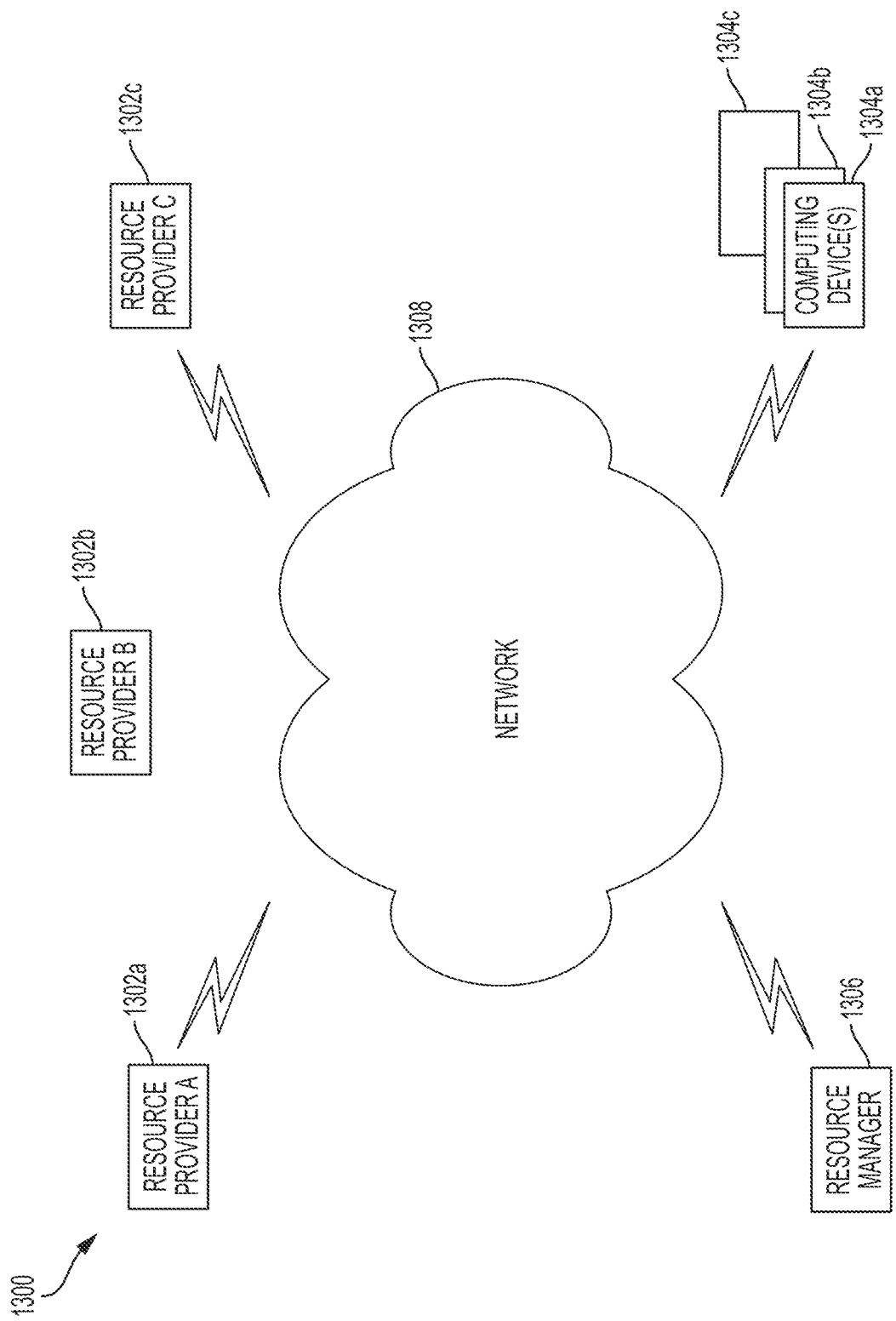
FIG. 13 is a block diagram of an example network environment for use in the methods and systems described herein, according to an illustrative embodiment.

As shown in FIG. 13, an implementation of a network environment 1300 for use in providing systems, methods, and architectures for generation of artificial landmarks for distortion correction and/or co-registration of images as described herein. In brief overview, referring now to FIG. 13, a block diagram of an exemplary cloud computing environment 1300 is shown and described. The cloud computing environment 1300 may include one or more resource providers 1302a, 1302b, 1302c (collectively, 1302). Each resource provider 1302 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 1302 may be connected to any other resource provider 1302 in the cloud computing environment 1300. In some implementations, the resource providers 1302 may be connected over a computer network 1308. Each resource provider 1302 may be connected to one or more computing device 1304a, 1304b, 1304c (collectively, 1304), over the computer network 1308.

The cloud computing environment 1300 may include a resource manager 1306. The resource manager 1306 may be connected to the resource providers 1302 and the computing devices 1304 over the computer network 1308. In some implementations, the resource manager 1306 may facilitate the provision of computing resources by one or more resource providers 1302 to one or more computing devices 1304. The resource manager 1306 may receive a request for a computing resource from a particular computing device 1304. The resource manager 1306 may identify one or more resource providers 1302 capable of providing the computing resource requested by the computing device 1304. The resource manager 1306 may select a resource provider 1302 to provide the computing resource. The resource manager 1306 may facilitate a connection between the resource provider 1302 and a particular computing device 1304. In some implementations, the resource manager 1306 may establish a connection between a particular resource provider 1302 and a particular computing device 1304. In some implementations, the resource manager 1306 may redirect a particular computing device 1304 to a particular resource provider 1302 with the requested computing resource.

Figure 14:
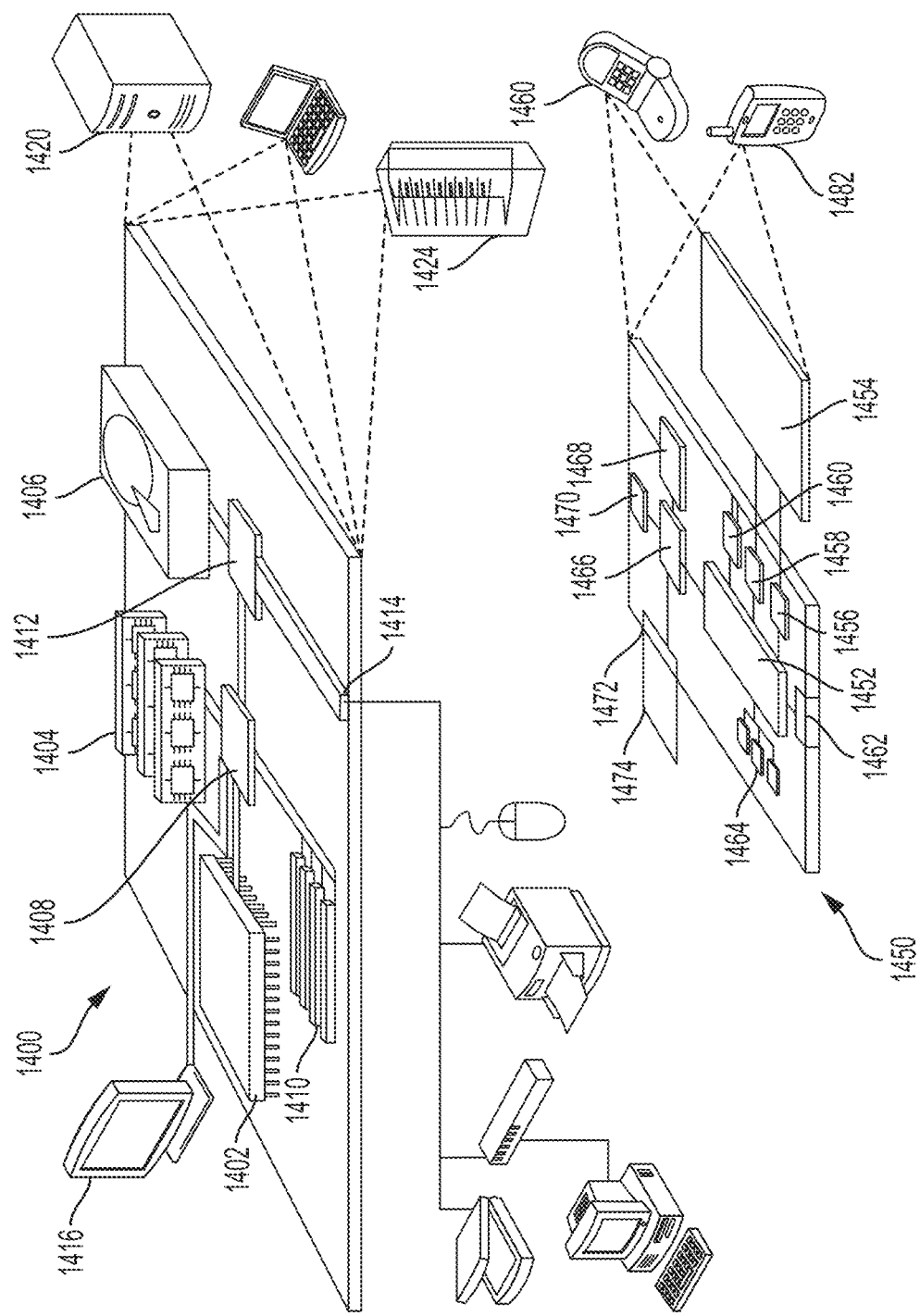
FIG. 14 is a block diagram of an example computing device and an example mobile computing device, for use in illustrative embodiments of the invention.

FIG. 14 shows an example of a computing device 1400 and a mobile computing device 1450 that can be used to implement the techniques described in this disclosure. The computing device 1400 is intended to represent various forms of digital computers, such as laptops, desktops, workstations, personal digital assistants, servers, blade servers, mainframes, and other appropriate computers. The mobile computing device 1450 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 1400 includes a processor 1402, a memory 1404, a storage device 1406, a high-speed interface 1408 connecting to the memory 1404 and multiple high-speed expansion ports 1410, and a low-speed interface 1412 connecting to a low-speed expansion port 1414 and the storage device 1406. Each of the processor 1402, the memory 1404, the storage device 1406, the high-speed interface 1408, the high-speed expansion ports 1410, and the low-speed interface 1412, are interconnected using various busses, and may be mounted on a common motherboard or in other manners as appropriate. The processor 1402 can process instructions for execution within the computing device 1400, including instructions stored in the memory 1404 or on the storage device 1406 to display graphical information for a GUI on an external input/output device, such as a display 1416 coupled to the high-speed interface 1408. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system). Thus, as the term is used herein, where a plurality of functions are described as being performed by "a processor", this encompasses embodiments wherein the plurality of functions are performed by any number of processors (one or more) of any number of computing devices (one or more). Furthermore, where a function is described as being performed by "a processor", this encompasses embodiments wherein the function is performed by any number of processors (one or more) of any number of computing devices (one or more) (e.g., in a distributed computing system).

The memory 1404 stores information within the computing device 1400. In some implementations, the memory 1404 is a volatile memory unit or units. In some implementations, the memory 1404 is a non-volatile memory unit or units. The memory 1404 may also be another form of computer-readable medium, such as a magnetic or optical disk.

The storage device 1406 is capable of providing mass storage for the computing device 1400. In some implementations, the storage device 1406 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 1402), perform one or more methods, such as those described above. The instructions can also be stored by one or more storage devices such as computer- or machine-readable mediums (for example, the memory 1404, the storage device 1406, or memory on the processor 1402).

The high-speed interface 1408 manages bandwidth-intensive operations for the computing device 1400, while the low-speed interface 1412 manages lower bandwidth-intensive operations. Such allocation of functions is an example only. In some implementations, the high-speed interface 1408 is coupled to the memory 1404, the display 1416 (e.g., through a graphics processor or accelerator), and to the high-speed expansion ports 1410, which may accept various expansion cards (not shown). In the implementation, the low-speed interface 1412 is coupled to the storage device 1406 and the low-speed expansion port 1414. The low-speed expansion port 1414, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 1400 may be implemented in a number of different forms, as shown in the figure. For example, it may be implemented as a standard server 1420, or multiple times in a group of such servers. In addition, it may be implemented in a personal computer such as a laptop computer 1422. It may also be implemented as part of a rack server system 1424. Alternatively, components from the computing device 1400 may be combined with other components in a mobile device (not shown), such as a mobile computing device 1450. Each of such devices may contain one or more of the computing device 1400 and the mobile computing device 1450, and an entire system may be made up of multiple computing devices communicating with each other.

The mobile computing device 1450 includes a processor 1452, a memory 1464, an input/output device such as a display 1454, a communication interface 1466, and a transceiver 1468, among other components. The mobile computing device 1450 may also be provided with a storage device, such as a micro-drive or other device, to provide additional storage. Each of the processor 1452, the memory 1464, the display 1454, the communication interface 1466, and the transceiver 1468, are interconnected using various buses, and several of the components may be mounted on a common motherboard or in other manners as appropriate.

The processor 1452 can execute instructions within the mobile computing device 1450, including instructions stored in the memory 1464. The processor 1452 may be implemented as a chipset of chips that include separate and multiple analog and digital processors. The processor 1452 may provide, for example, for coordination of the other components of the mobile computing device 1450, such as control of user interfaces, applications run by the mobile computing device 1450, and wireless communication by the mobile computing device 1450.

The processor 1452 may communicate with a user through a control interface 1458 and a display interface 1456 coupled to the display 1454. The display 1454 may be, for example, a TFT (Thin-Film-Transistor Liquid Crystal Display) display or an OLED (Organic Light Emitting Diode) display, or other appropriate display technology. The display interface 1456 may comprise appropriate circuitry for driving the display 1454 to present graphical and other information to a user. The control interface 1458 may receive commands from a user and convert them for submission to the processor 1452. In addition, an external interface 1462 may provide communication with the processor 1452, so as to enable near area communication of the mobile computing device 1450 with other devices. The external interface 1462 may provide, for example, for wired communication in some implementations, or for wireless communication in other implementations, and multiple interfaces may also be used.

The memory 1464 stores information within the mobile computing device 1450. The memory 1464 can be implemented as one or more of a computer-readable medium or media, a volatile memory unit or units, or a non-volatile memory unit or units. An expansion memory 1474 may also be provided and connected to the mobile computing device 1450 through an expansion interface 1472, which may include, for example, a SIMM (Single In Line Memory Module) card interface. The expansion memory 1474 may provide extra storage space for the mobile computing device 1450, or may also store applications or other information for the mobile computing device 1450. Specifically, the expansion memory 1474 may include instructions to carry out or supplement the processes described above, and may include secure information also. Thus, for example, the expansion memory 1474 may be provide as a security module for the mobile computing device 1450, and may be programmed with instructions that permit secure use of the mobile computing device 1450. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier. The instructions, when executed by one or more processing devices (for example, processor 1452), perform one or more methods, such as those described above. The instructions can also be stored by one or more storage devices, such as one or more computer- or machine-readable mediums (for example, the memory 1464, the expansion memory 1474, or memory on the processor 1452). In some implementations, the instructions can be received in a propagated signal, for example, over the transceiver 1468 or the external interface 1462.

The mobile computing device 1450 may communicate wirelessly through the communication interface 1466, which may include digital signal processing circuitry where necessary. The communication interface 1466 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 1468 using a radio-frequency. In addition, short-range communication may occur, such as using a Bluetooth®, Wi-Fi™, or other such transceiver (not shown). In addition, a GPS (Global Positioning System) receiver module 1470 may provide additional navigation- and location-related wireless data to the mobile computing device 1450, which may be used as appropriate by applications running on the mobile computing device 1450.

The mobile computing device 1450 may also communicate audibly using an audio codec 1460, which may receive spoken information from a user and convert it to usable digital information. The audio codec 1460 may likewise generate audible sound for a user, such as through a speaker, e.g., in a handset of the mobile computing device 1450. Such sound may include sound from voice telephone calls, may include recorded sound (e.g., voice messages, music files, etc.) and may also include sound generated by applications operating on the mobile computing device 1450.

The mobile computing device 1450 may be implemented in a number of different forms, as shown in the figure. For example, it may be implemented as a cellular telephone 1480. It may also be implemented as part of a smart-phone 1482, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

Elements of different implementations described herein may be combined to form other implementations not specifically set forth above. Elements may be left out of the processes, computer programs, databases, etc. described herein without adversely affecting their operation. In addition, the logic flows depicted in the figures do not require the particular order shown, or sequential order, to achieve desirable results. Various separate elements may be combined into one or more individual elements to perform the functions described herein. In view of the structure, functions and apparatus of the systems and methods described here, in some implementations.

Throughout the description, where apparatus and systems are described as having, including, or comprising specific components, or where processes and methods are described as having, including, or comprising specific steps, it is contemplated that, additionally, there are apparatus, and systems of the present invention that consist essentially of, or consist of, the recited components, and that there are processes and methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

While apparatus, systems, and methods have been particularly shown and described with reference to specific preferred embodiments, it should be understood by those skilled in the art that various changes in form and detail may be made therein without departing from the spirit and scope of the invention as defined by the appended claims.

What is claimed is:

1. A system for registration of one or more 3-D images of a subject, the system comprising:
   a processor; and
   a memory with instructions stored thereon, wherein the instructions, when executed by the processor, cause the processor to:
   (a) receive a 3-D image of the subject, wherein the 3-D image comprises a graphical representation of one or more bones of interest;
   (b) identify in the graphical representation one or more bones of interest and a reference object;
   (c) automatically generate one or more seed artificial objects, each seed artificial object being within a first distance interval from the reference object and corresponding to a region of a bone of interest in the graphical representation;
   (d) for each automatically generated seed artificial object, automatically generate a plurality of associated subsequent artificial objects, thereby creating a set of artificial objects within the image;
   (e) automatically perform registration of one or more images of the subject using the set of artificial objects within the image;
   (f) identify one or more dangerous regions of the image corresponding to regions in which a distance between a first and second bone of interest in the graphical representation is below a predefined threshold distance; and
   (g) automatically generate each artificial object such that it is sufficiently far from any identified dangerous region within the image.

2. The system of claim 1, wherein the instructions cause the processor to automatically generating the one or more seed artificial objects by:
   determining a distance map comprising intensity values at each of a plurality of points in three dimensions, each of the intensity values of the distance map corresponding to a distance from a given point in 3-D space to the reference object;
   generating a distance interval mask from the distance map; and
   applying an AND operation between the distance interval mask and a mask corresponding to the identified one or more bones of interest, thereby identifying a plurality of regions of the identified bones of interest that are within the first distance interval from the reference object.

3. The system of claim 1, wherein for each automatically generated seed artificial object, the plurality of associated subsequent artificial objects comprises an equidistant chain of artificial objects.

4. The system of claim 1, wherein each artificial object is a predefined threshold distance from an identified additional bone within the graphical representation.

5. The system of claim 1, wherein the instructions cause the processor to automatically generate the plurality of subsequent artificial objects associated with a respective seed artificial object by generating a chain of artificial objects along a bone of interest by beginning with the seed artificial object and, in a stepwise fashion, generating new subsequent artificial objects, each newly generated artificial object proceeding outwards, away from the identified reference object, along the bone of interest.

6. The system of claim 5, wherein the instructions cause the processor to generate the chain of artificial objects associated with the respective seed artificial object by, for at least one newly generated artificial object of the chain of artificial objects:
   determining whether the newly generated artificial object is within a predetermined threshold distance from an identified additional bone in the graphical representation; and
   responsive to determining that the newly generated artificial object is within the predetermined threshold distance from the identified additional bone of the image, terminating generation of subsequent artificial objects associated with the respective seed artificial object.

7. The system of claim 1, wherein each artificial object of the set of artificial objects within the image is confirmed to have at least a predefined threshold volume.

8. The system of claim 1, wherein the instructions cause the processor to:
   determine, based on the set of artificial objects within the image, an image registration transformation; and
   apply the image registration transformation to a region of the 3-D image, thereby registering the 3-D image.

9. The system of claim 8, wherein the image registration transformation yields symmetrization of the 3-D image, thereby correcting distortions in the image.

10. The system of claim 8, wherein the received image corresponds to a first image, and the image registration transformation aligns the first image with a second image of the subject, thereby co-registering the first image with the second image.

11. The system of claim 8, wherein the instructions cause the processor to determine the image registration transformation by:
    determining, from the set of artificial objects within the image, a set of artificial landmarks within the image, each landmark corresponding to a point determined from a corresponding artificial object; and
    determining the image registration transformation using the set of artificial landmarks within the image and a set of target landmarks, wherein the image registration transformation is determined to, when applied to points corresponding to the artificial landmarks within the image, substantially optimize alignment of the set of artificial landmarks with the set of target landmarks.

12. The system of claim 11, wherein the set of target landmarks is symmetric.

13. The system of claim 11, wherein the instructions cause the processor to determine the set of target landmarks using the set of artificial landmarks within the image.

14. The system of claim 11, wherein the set of target landmarks is a set of predetermined target landmarks.

15. The system of claim 8, wherein the received 3-D image comprises one or more regions corresponding to graphical representations of soft tissue, and the instructions cause the processor to apply the image registration transformation to the one or more regions of the image corresponding to graphical representations of soft tissue, thereby registering the soft tissue regions.

16. The system of claim 8, wherein the received 3-D image of the subject corresponds to a first image recorded via a first modality, and, wherein the instructions cause the processor to:
   receive a second image recorded via a second modality;
   determine, based on the set of artificial objects within the image, a first image registration transformation;
   determine, based on the first image registration transform, a second image registration transformation; and
   apply the second image registration transformation to a region of the second image.

17. The system of claim 16, wherein the second image is recorded at substantially the same time as the first image, with the subject in a substantially similar pose and/or position.

18. The system of claim 16, wherein the second image registration transformation is the same as the first image registration transformation.

19. The system of claim 16, wherein coordinates of a plurality of points of the first image are related to coordinates of a plurality of points of the second image via a known functional relationship.

20. The system of claim 1, wherein:
   the 3-D image comprises a graphical representation of rib bones and a backbone,
   the identified one or more bones of interest comprise rib bones, and
   the identified reference object is a backbone of the subject.

21. The system of claim 20, wherein:
   the graphical representation of rib bones includes a plurality of pairs of opposite rib bones,
   each rib bone artificial object of a portion of the plurality of rib bone artificial objects belongs to one of a plurality of pairs of rib bone artificial objects, each pair comprising a first rib bone artificial object associated with a first rib bone of a pair of opposite rib bones and a second rib bone artificial object associated with a second rib bone of the pair of opposite rib bones, and
   for each pair of rib bone artificial objects, (i) a difference between a volume represented by the first object of the pair and a volume represented by the second object of the pair is below a predefined threshold volume difference, and/or (ii) a difference between a height of the first object of the pair and a height of the second object of the pair is below a predefined threshold height difference.

22. The system of claim 20, wherein the rib bones in the graphical representation includes one or more pairs of opposite rib bones, and wherein the instruction cause the processor to automatically generate a plurality of seed rib bone artificial objects by:
   identifying a set of prospective seed rib bone artificial objects corresponding to a plurality of regions of the rib bones that are within a distance interval from the backbone;
   automatically identifying one or more pairs of prospective seed rib bone artificial objects, each pair comprising a first seed rib bone artificial object of a first rib bone of the pair of rib bones and corresponding second seed rib bone artificial object of the opposite rib bone;
   applying a pair comparison filter to the set of prospective seed rib bone artificial objects, wherein application of the pair comparison filter eliminates, from the set, pairs of artificial objects for which (i) a difference between a volume represented by the first object of the pair and a volume represented by the second object of the pair is above a predefined threshold volume difference, and/or (ii) a difference between a height of the first object of the pair and a height of the second object of the pair is above a predefined threshold height difference; and
   following application of the pair comparison filter, selecting each seed rib bone artificial object from the set of prospective seed rib bone artificial objects.

23. The system of claim 1, wherein the 3-D image comprises a graphical representation of a breastbone of the subject and a lower end of the breastbone.

24. The system of claim 23, wherein the one or more bones of interest comprise(s) the breastbone in the graphical representation and the reference object comprises a lower end of the breastbone.

25. A system for registration of one or more 3-D images of a subject, the system comprising:
   a processor; and
   a memory with instructions stored thereon, wherein the instructions, when executed by the processor, cause the processor to:
   (a) receive a 3-D image of the subject, wherein the 3-D image comprises a graphical representation of one or more bones of interest;
   (b) identify in the graphical representation one or more bones of interest and a reference object;
   (c) automatically generate one or more seed artificial objects, each seed artificial object being within a first distance interval from the reference object and corresponding to a region of a bone of interest in the graphical representation;
   (d) for each automatically generated seed artificial object, automatically generate a plurality of associated subsequent artificial objects, thereby creating a set of artificial objects within the image;
   (e) automatically perform registration of one or more images of the subject using the set of artificial objects within the image;
   (f) determine, based on the set of artificial objects within the image, an image registration transformation by:
      determining, from the set of artificial objects within the image, a set of artificial landmarks within the image, each landmark corresponding to a point determined from a corresponding artificial object; and
      determining the image registration transformation using the set of artificial landmarks within the image and a set of symmetric target landmarks, wherein the image registration transformation is determined to, when applied to points corresponding to the artificial landmarks within the image, substantially optimize alignment of the set of artificial landmarks with the set of symmetric target landmarks;

(g) apply the image registration transformation to a region of the 3-D image, thereby registering the 3-D image;
(h) identify one or more dangerous regions of the image corresponding to regions in which a distance between a first and second bone of interest in the graphical representation is below a predefined threshold distance; and
(i) automatically generate each artificial object such that it is sufficiently far from any identified dangerous region within the image.

26. A system for registration of one or more 3-D images of a subject, the system comprising:
a processor; and
a memory with instructions stored thereon, wherein the instructions, when executed by the processor, cause the processor to:
(a) receive a 3-D image of the subject, wherein the 3-D image comprises a graphical representation of one or more bones of interest;
(b) identify in the graphical representation one or more bones of interest and a reference object;
(c) automatically generate one or more seed artificial objects, each seed artificial object being within a first distance interval from the reference object and corresponding to a region of a bone of interest in the graphical representation;
(d) for each automatically generated seed artificial object, automatically generate a plurality of associated subsequent artificial objects, thereby creating a set of artificial objects within the image;
(e) automatically perform registration of one or more images of the subject using the set of artificial objects within the image;
(f) determine, based on the set of artificial objects within the image, an image registration transformation;
(g) apply the image registration transformation to a region of the 3-D image, thereby registering the 3-D image that corresponds to a first image recorded via a first modality;
(h) receive a second image recorded via a second modality;
(i) determine, based on the set of artificial objects within the image, a first image registration transformation;
(j) determine, based on the first image registration transform, a second image registration transformation;
(k) apply the second image registration transformation to a region of the second image;
(l) identify one or more dangerous regions of the image corresponding to regions in which a distance between a first and second bone of interest in the graphical representation is below a predefined threshold distance; and
(m) automatically generate each artificial object such that it is sufficiently far from any identified dangerous region within the image,
wherein the second image is recorded at substantially the same time as the first image, with the subject in a substantially similar pose and/or position.

* * * * *